United States Patent
Liotta et al.

(10) Patent No.: US 12,331,096 B2
(45) Date of Patent: Jun. 17, 2025

(54) BINDING DOMAIN MAPPING AND COMPOUNDS, COMPOSITIONS, COMPLEXES, METHODS, AND KITS RELATED THERETO

(71) Applicant: GEORGE MASON RESEARCH FOUNDATION, INC., Fairfax, VA (US)

(72) Inventors: Lance Liotta, Fairfax, VA (US); Alessandra Luchini Kunkel, Fairfax, VA (US); Amanda Still, Fairfax, VA (US); Mikell Paige, Fairfax, VA (US)

(73) Assignee: George Mason Research Foundation, Inc., Fairfax, VA (US)

( * ) Notice: Subject to any disclaimer, the term of this patent is extended or adjusted under 35 U.S.C. 154(b) by 739 days.

(21) Appl. No.: 17/415,190

(22) PCT Filed: Jan. 3, 2020

(86) PCT No.: PCT/US2020/012196
§ 371 (c)(1),
(2) Date: Jun. 17, 2021

(87) PCT Pub. No.: WO2020/142700
PCT Pub. Date: Jul. 9, 2020

(65) Prior Publication Data
US 2022/0064259 A1    Mar. 3, 2022

Related U.S. Application Data

(60) Provisional application No. 62/788,214, filed on Jan. 4, 2019.

(51) Int. Cl.
| | | |
|---|---|---|
| *C07K 14/705* | (2006.01) |
| *A61K 38/00* | (2006.01) |
| *A61P 35/00* | (2006.01) |
| *C07C 303/22* | (2006.01) |
| *C07C 309/50* | (2006.01) |
| *C07K 7/06* | (2006.01) |
| *C07K 7/08* | (2006.01) |
| *G01N 33/68* | (2006.01) |

(52) U.S. Cl.
CPC ........ *C07K 14/70532* (2013.01); *A61P 35/00* (2018.01); *C07C 303/22* (2013.01); *C07C 309/50* (2013.01); *C07K 7/06* (2013.01); *C07K 7/08* (2013.01); *C07K 14/70521* (2013.01); *G01N 33/6845* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2,612,494 A | 9/1952 | Von et al. | |
| 3,086,833 A | 4/1963 | Clemens | |
| 4,163,675 A | 8/1979 | Hirano et al. | |
| 4,325,908 A | 4/1982 | Scheinthal et al. | |
| 4,395,264 A | 7/1983 | Fenwick | |
| 10,126,304 B2 | 11/2018 | Luchini et al. | |
| 2013/0137112 A1 | 5/2013 | Patton et al. | |
| 2014/0286952 A1 | 9/2014 | Shah | |
| 2015/0017194 A1* | 1/2015 | Akahata ........... C07K 14/70503 |
| | | | 435/320.1 |
| 2017/0205669 A1 | 7/2017 | Ono et al. | |
| 2021/0371496 A1* | 12/2021 | Desallais .......... C07K 16/2827 |

FOREIGN PATENT DOCUMENTS

| | | | |
|---|---|---|---|
| CN | 110478472 A | * | 11/2019 |
| WO | 2014113433 A1 | | 7/2014 |

OTHER PUBLICATIONS

English translation of CN-110478472-A. [retrieved on Mar. 21, 2024] Retrieved from Google Patents using <URL: https://patents.google.com/patent/CN110478472A/en?oq=CN110478472> (Year: 2024).*
HPD-1 [*Homo sapiens*] GenBank: AAC51773.1 (Year: 2025).*
Programmed cell death 1 ligand 1 isoform a precursor [*Homo sapiens*] NCBI Reference Sequence: NP_054862.1 (Year: 2025).*
MAG: DNA (cytosine-5-)-methyltransferase [Candidatus Omnitrophica bacterium] GenBank: MBU4311201.1 (Year: 2025).*
International Search Report and Written Opinion mailed Jun. 4, 2020, PCT/US2020/012196.
Ali-Shtayeh , et al., "In-vitro screening of acetylcholinesterase inhibitory activity of extracts from Palestinian indigenous flora in relation to the treatment of Alzheimer's disease.", Functional Foods in Health and Disease 2014; 4 (9):381-400.

* cited by examiner

*Primary Examiner* — Christina Bradley
(74) *Attorney, Agent, or Firm* — Saul Ewing LLP; Alireza Behrooz

(57) ABSTRACT

The present disclosure relates to compounds, complexes, compositions, kits and methods for determining interacting and/or binding sites between e.g., proteins, proteins and nucleic acids, proteins and small molecules, or intrachain protein domains. The disclosure provides rapid and direct positive identification of the contact interface region between such molecules, and can be applied to individual interacting pairs, as well as large-scale or global interactions.

5 Claims, 6 Drawing Sheets

Specification includes a Sequence Listing.

SEQUENCE LISTING

<160> NUMBER OF SEQ ID NOS: 14

<210> SEQ ID NO 1
<211> LENGTH: 17
<212> TYPE: PRT
<213> ORGANISM: Artificial Sequence
<220> FEATURE:
<223> OTHER INFORMATION: Synthetic peptide

<400> SEQUENCE: 1

Tyr Arg Cys Met Ile Ser Tyr Gly Gly Ala Asp Tyr Lys Arg Ile Thr
1               5                   10                  15

Val

<210> SEQ ID NO 2
<211> LENGTH: 18
<212> TYPE: PRT
<213> ORGANISM: Artificial Sequence

```
<220> FEATURE:
<223> OTHER INFORMATION: Synthetic peptide

<400> SEQUENCE: 2

Cys Tyr Arg Ala Met Ile Ser Tyr Gly Gly Ala Asp Tyr Lys Arg Ile
1               5                   10                  15
Thr Cys

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide

<400> SEQUENCE: 3

Leu Lys Tyr Asp Ala Pro Ala Phe Thr Val Thr
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic peptide

<400> SEQUENCE: 4

Cys Leu Lys Tyr Asp Ala Pro Ala Phe Thr Val Thr Cys
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Synthetic peptide

<400> SEQUENCE: 5

Leu Asn Trp Tyr Arg Met Ser Pro Ser Asn Gln Thr Asp Lys Leu Ala
1               5                   10                  15
Ala

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Leu Asn Trp Tyr Arg Met Ser Pro Ser Asn Gln Thr Asp Lys Leu Ala
1               5                   10                  15
Ala

<210> SEQ ID NO 7
<211> LENGTH: 19
<212> TYPE: PRT
<213> ORGANISM: Artificial Sequence
<220> FEATURE:
<223> OTHER INFORMATION: Synthetic peptide

<400> SEQUENCE: 7

Cys Leu Asn Trp Tyr Arg Met Ser Pro Ser Asn Gln Thr Asp Lys Leu
1               5                   10                  15
```

```
Ala Ala Cys

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

Ala Ile Ser Leu Ala Pro Lys Ala Gln Ile Lys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic peptide

<400> SEQUENCE: 9

Cys Ala Ile Ser Leu Ala Pro Lys Ala Gln Ile Lys Cys
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide

<400> SEQUENCE: 10

Lys Val Thr Leu Val
1               5

<210> SEQ ID NO 11
<211> LENGTH: 17
<212> TYPE: PRT
<213> ORGANISM: Artificial Sequence
<220> FEATURE:
<223> OTHER INFORMATION: Synthetic peptide

<400> SEQUENCE: 11

Arg Asp Asp Ile Ser Glu Ile Gln Ser Leu Ala Ser Asp His Ser Gly
1               5                   10                  15

Arg

<210> SEQ ID NO 12
<211> LENGTH: 13
<212> TYPE: PRT
<213> ORGANISM: Artificial Sequence
<220> FEATURE:
<223> OTHER INFORMATION: Synthetic peptide

<400> SEQUENCE: 12

Lys Glu Gly Leu Glu Glu Gly Asp Gln Ile Leu Arg Val
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13
```

```
Lys Phe Pro Ala Tyr Glu Arg
1               5

<210> SEQ ID NO 14
<211> LENGTH: 14
<212> TYPE: PRT
<213> ORGANISM: Artificial Sequence
<220> FEATURE:
<223> OTHER INFORMATION: Synthetic peptide

<400> SEQUENCE: 14

Lys His Ala Leu Leu Asp Val Thr Pro Asn Ala Val Asp Arg
1               5                   10
```

BINDING DOMAIN MAPPING AND COMPOUNDS, COMPOSITIONS, COMPLEXES, METHODS, AND KITS RELATED THERETO

CROSS-REFERENCE TO RELATED APPLICATIONS

The present application is a 35 U.S.C. 371 national phase application from, and claims priority to, International Patent Application No. PCT/US2020/012196, filed Jan. 3, 2020, which is entitled to priority under 35 USC 119 (e) to U.S. Provisional Patent Application No. 62/788,214, filed Jan. 4, 2019, which is herein incorporated by reference in its entirety.

STATEMENT REGARDING FEDERALLY SPONSORED RESEARCH OR DEVELOPMENT

This invention was made with government support under grant number R33CA206937 awarded by the National Institutes of Health. The government has certain rights in the invention.

REFERENCE TO SEQUENCE LISTING

The Sequence Listing concurrently submitted herewith as a text file named "381789_7003US1_ST25.txt," created on Jun. 9, 2020 and having a size of 3,710 bytes is herein incorporated by reference pursuant to 37 C.F.R. § 1.52 (e) (5).

FIELD OF THE INVENTION

The present invention relates to compounds, compositions, and methodologies including, but not limited to, for determining binding sites between proteins, proteins and nucleic acids, or proteins and small molecules.

BACKGROUND

Defects in protein folding, improper protein-protein interactions (PPIs), or dysfunctional cellular machinery, is the functional cause of disease. For example, PPIs lie at the heart of protein signaling pathways, and thus are crucial interactions that influence a number of disease states. However, despite their relevance to disease pathology, PPIs have historically rarely been the target of drug discovery efforts due to several difficulties in targeting the interaction interface. For example, protein-protein interfaces can be large, flat, and featureless, leading to challenges in the design of small molecules with sufficient potency and specificity. Further, lack of crystal structures of protein-protein complexes can make identifying precise interface regions and interface topology difficult, notwithstanding that crystal structures of protein-protein complexes may not accurately depict the biological assembly due to nonphysiological crystallization conditions. Also, non-crystallographic techniques for identification of protein-protein interfaces, such as hydroxy radical labelling, hydrogen deuterium exchange, or chemical crosslinking, can also be laborious and prone to false positives due to nonphysiological solution conditions.

Characterization of binding domain interfaces, e.g. between interacting proteins, is the starting point for the next generation of therapies that block such interactions. Traditional experimental approaches to interactomics, including Two-hybrid screening, Tandem Affinity Purification, X-ray tomography, Optical fluorescence microscopy, are error prone, time consuming, or require large amounts of protein and/or genetic tagging of the proteins. Moreover, nearly thirty percent (30%) of the identified interactions by these existing methods are artifacts.

There is a need for new and effective compounds, compositions, and methods for determining interaction interface(s) of a protein.

SUMMARY OF THE INVENTION

In some aspects, the present invention provides organic molecule masking pigments that bind to proteins, for example, and can be used to bind to or "paint" the exposed regions of a protein in solution.

In one aspect, the present invention provides a compound having Formula (I):

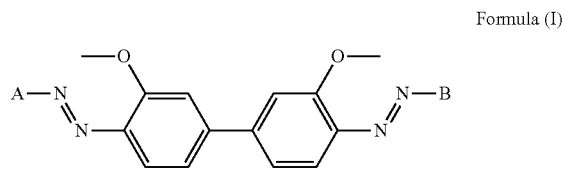

Formula (I)

wherein A and B each independently have Formula (a),

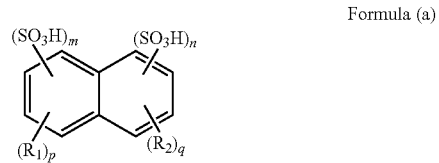

Formula (a)

wherein $R_1$ and $R_2$ each independently is —OH or —NH$_2$; m, n, p and q each independently is 0, 1, 2, 3, or 4 and the sum of m+n is not zero.

In another aspect, the present invention provides a method for preparing a compound. The method comprises performing an azo coupling reaction between an aryl diazonium compound and a naphthalene derivative having a sulfonic acid group, thereby coupling the aryl diazonium compound to the naphthalene derivative to form the compound.

In some aspects, the present invention provides a compound prepared by a method comprising performing an azo coupling reaction between an aryl diazonium compound and a naphthalene derivative having a sulfonic acid group, whereby the aryl diazonium compound is coupled to the naphthalene derivative to form the compound.

In other aspects, the present invention provides a complex comprising a compound bound to a protein. The compound has Formula (I) and/or is prepared by the method comprising performing the azo coupling reaction disclosed herein.

In one aspect, the present invention provides a kit comprising a compound having Formula (I) and/or is prepared by the method comprising performing the azo coupling reaction disclosed herein.

In another aspect, the present invention provides a composition comprising a compound having Formula (I) and/or is prepared by the method comprising performing the azo coupling reaction disclosed herein.

In some aspects, the present invention provides a method for determining an interaction site of a protein. The method comprises contacting the protein with a compound to form a complex with the compound at an accessible region of the protein that is accessible by the compound; and determining an inaccessible region of the protein that is not accessible by the compound, thereby determining the interaction site. The compound has Formula (I) and/or is prepared by the method comprising performing the azo coupling reaction disclosed herein.

In other aspects, the present invention provides a method for determining an inhibitor for an interaction site of a protein. The method comprises contacting the protein with a compound to form a complex with the compound at an accessible region of the protein that is accessible by the compound; and determining an amino acid sequence of an inaccessible region of the protein that is not accessible by the compound, thereby determining the inhibitor. The compound has Formula (I) and/or is prepared by the method comprising performing the azo coupling reaction disclosed herein.

In one aspect, the present invention provides a peptide comprising the amino acid sequence, or variant thereof, set forth as:
  YRCMISYGGADYKRITV (SEQ ID NO:1) or variant thereof;
  CYRAMISYGGADYKRITC (SEQ ID NO:2) or variant thereof;
  LKYDAPAFTVT (SEQ ID NO:3) or variant thereof;
  CLKYDAPAFTVTC (SEQ ID NO:4) or variant thereof;
  LNWYRMSPSNQTDKLAA (SEQ ID NO:5) or variant thereof;
  LNWYRMSPSNQTDKLAA (SEQ ID NO:6) or variant thereof;
  CLNWYRMSPSNQTDKLAAC (SEQ ID NO:7) or variant thereof;
  AISLAPKAQIK (SEQ ID NO:8) or variant thereof; or
  CAISLAPKAQIKC (SEQ ID NO:9) or variant thereof.

In another aspect, the present invention provides a peptide comprising the amino acid sequence, or variant thereof, set forth as:
  KVTLV (SEQ ID NO:10) or variant thereof;
  RDDISEIQSLASDHSGR (SEQ ID NO:11) or variant thereof;
  KEGLEEGDQILRV (SEQ ID NO:12) or variant thereof;
  KFPAYER (SEQ ID NO:13) or variant thereof; or
  KHALLDVTPNAVDR (SEQ ID NO:14) or variant thereof.

In some aspects, the present invention provides a method for preventing or disrupting an interaction between programmed death 1 (PD-1) and programmed death ligand 1 (PD-L1), the method comprising contacting PD-1 or PD-L1 with a peptide before, concomitant with, or after the interaction between PD-1 and PD-L1. The peptide comprises the amino acid sequence, or variant thereof, set forth as SEQ ID NO:1, 2, 3, 4, 5, 6, 7, 8, or 9.

In another aspect, the present invention provides a method for treating or preventing a disease, disorder, or condition associated with PD-1/PD-L1 interaction in a subject in need thereof, the method comprising administering to the subject a therapeutically or prophylactically effective amount of a peptide or a polynucleotide encoding the peptide. The peptide comprises the amino acid sequence, or variant thereof, set forth as SEQ ID NO:1, 2, 3, 4, 5, 6, 7, 8, or 9.

In other aspects, the present invention provides a method for preventing or disrupting an interaction between yes-associated protein (YAP) and zona occludens (ZO), the method comprising contacting YAP or ZO with a peptide before, concomitant with, or after the interaction between YAP and ZO. The peptide comprises the amino acid sequence, or variant thereof, set forth as SEQ ID NO:10, 11, 12, 13, or 14.

In another aspect, the present invention provides a method for treating or preventing a disease, disorder, or condition associated with YAP/ZO interaction in a subject in need thereof, the method comprising administering to the subject a therapeutically or prophylactically effective amount of a peptide or of a polynucleotide encoding the peptide. The peptide comprises the amino acid sequence, or variant thereof, set forth as SEQ ID NO:10, 11, 12, 13, or 14.

DETAILED DESCRIPTION OF THE INVENTION

Figure 1:
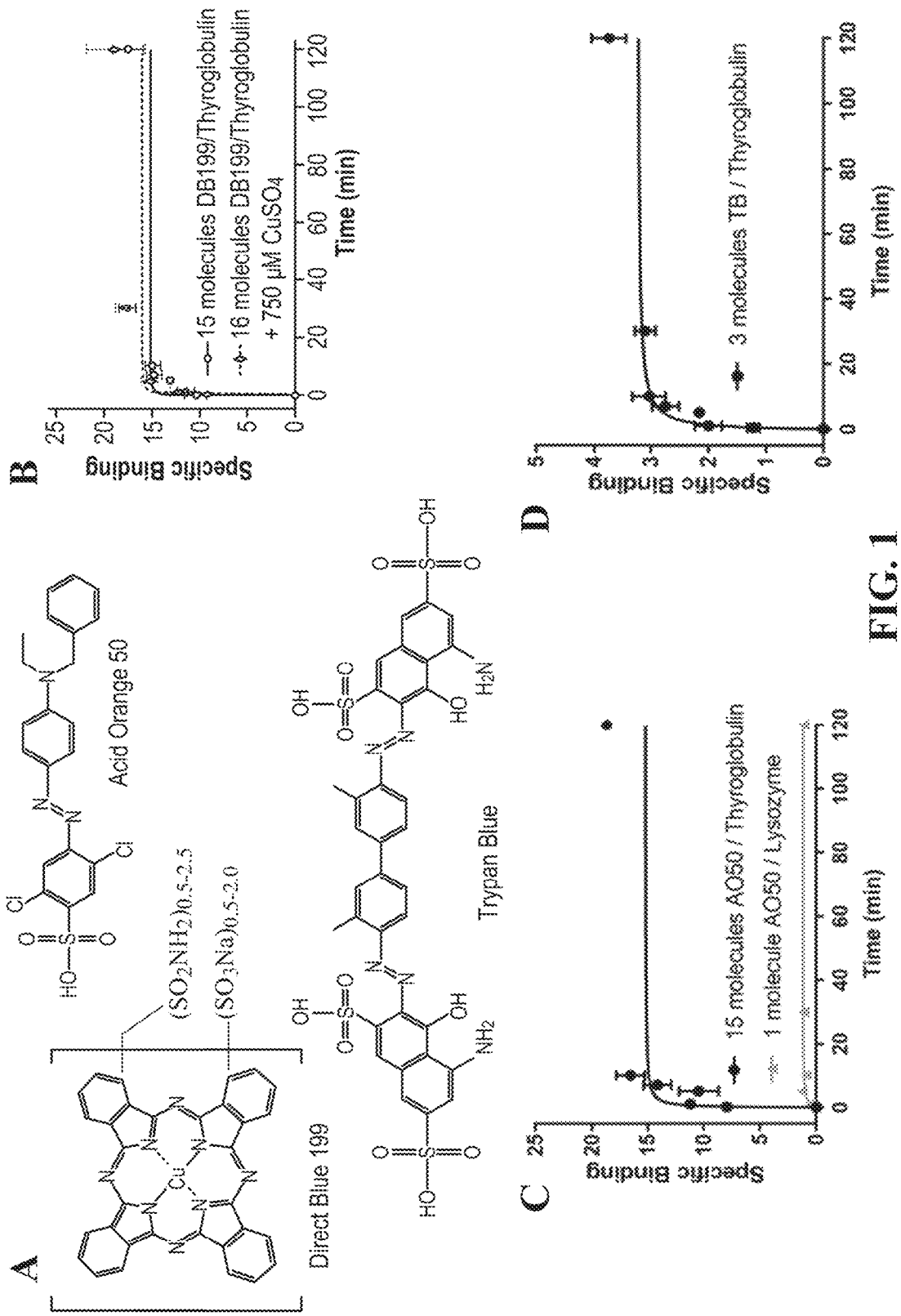
FIGS. 1A-1D are structures and graphs showing specific binding of commercially available molecular dyes. A) Structure of commercially available dyes Direct Blue 199 (DB199), Acid Orange 50 (AO50), and Trypan Blue (TB). B) DB199 binds to thyroglobulin, but not to lysozyme. Binding to thyroglobulin in the absence of CuSO4 (15 molecules at equilibrium) is not significantly greater than binding in the presence of CuSO4 (16 molecules at equilibrium), indicating the copper ion of DB199 is not primarily responsible for binding affinity. C) Acid Orange 50 binds to both thyroglobulin (15 molecules at equilibrium) and lysozyme (1 molecule at equilibrium). D) Trypan Blue binds to thyroglobulin, but not to lysozyme. Binding of trypan blue (3 molecules at equilibrium) is reduced compared to either DB199 or AO50. All data points were collected in duplicate, and final data was fit to the Michaelis Menton equation where Vmax represents specific binding at saturation.

As used herein, the term "protein" (singular or plural) includes a fragment of a protein. Further, the term "protein" includes a fusion protein. The term "fusion protein" includes a protein in which fragments or whole of two or more hetero-proteins are fused.

In some aspects, the present invention provides compounds that bind to proteins, for example, and can be used to bind to or "paint"/"mask" the exposed regions of a protein in solution. In one embodiment, the compounds bind with high affinity and slow off-rates, and span a small region comprising approximately 3 amino acids. Once bound to the protein, they block the trypsin (or other protease) cleavage site at the domain that is masked by the compound. In one embodiment, the compounds bind to a portion of a protein polypeptide chain of at least 3 amino acids where the amino acid in position 1 (P1) from the amino terminus is any amino acid, position 2 (P2) is K or R and the amino acid in position 3 (P3) is not P. In other embodiments, the compounds are organic molecule masking pigments.

In one embodiment, the cleavage site corresponds to a protease, wherein the protease is trypsin, Arg-C proteinase, Asp-N endopeptidase, Caspase1, Caspase2, Caspase3, Caspase4, Caspase5, Caspase6, Caspase7, Caspase8, Caspase9, Caspase10, Chymotrypsin, Clostripain (Clostridiopeptidase B), Enterokinase, Factor Xa, Glutamyl endopeptidase, GranzymeB, LysC, LysN, Pepsin, Proline-endopeptidase, Proteinase K, Staphylococcal peptidase I, Tobacco etch virus protease, Thermolysin, or Thrombin.

The technology, in some embodiments, can be applied to identifying an interaction site of a protein of any size, preferably, in other embodiments, a protein having sufficient length to fold into at least a three-dimensional structure. In one embodiment, proteins include, but are not limited to, members of signaling pathways, hormones, immunoglobulins, repressors/activators, targets of inhibitors/activators, enzymes, cytokines, chemokines, myokines, lipokines, growth factors, receptors, receptor domains, neurotransmitters, neurotrophins, interleukins, and interferons among others.

In other embodiments, the interaction site is a site of interaction within a single protein e.g., between two domains within a single protein (e.g., an intrachain interaction). In other embodiments, the interaction site is a site of interaction between a protein and another molecule (e.g., an interchain interaction between a protein and a binding partner).

In one aspect, the present invention provides a compound having Formula (I):

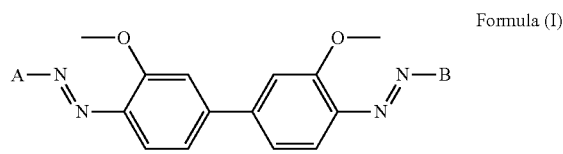

Formula (I)

wherein A and B each independently have Formula (a),

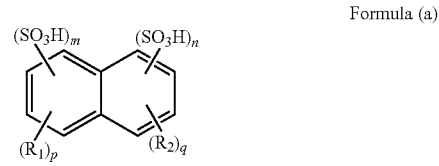

Formula (a)

wherein $R_1$ and $R_2$ each independently is —OH or —NH$_2$; m, n, p and q each independently is 0, 1, 2, 3, or 4 and the sum of m+n is not zero.

The term "compound" as used herein refers to a compound encompassed by a generic formula disclosed herein, any subgenus of the generic formula, and any specific compounds within the generic and subgeneric formula and is intended to include salts, solvates, hydrates, oxides, etc. of such compounds. In addition, the compounds of this invention include the tautomers, individual stereochemical isomers (arising from the selection of substituent groups) and mixtures of tautomers and/or isomers.

The carbon ring numbering system (i.e., C1-C10) for Formula (a) used herein is as follows:

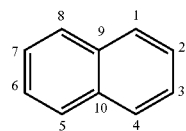

In one embodiment, the point of attachment of A and B each independently to the azo group in Formula (I) is at C1, C2, C3, C4, C5, C6, C7, or C8 of the carbon ring of Formula (a).

In another embodiment, the sum of p+q is not zero.

In some embodiments, the sum of p+q is 1 or 2.

In another embodiment, $R_1$ or $R_2$ is —$NH_2$.

In some embodiments, $R_1$ or $R_2$ is —OH.

In other embodiments, $R_1$ or $R_2$ is —$NH_2$ and the sum of p+q is 1 or 2.

In one embodiment, the point of attachment of A and B each independently to the azo group in Formula (I) is para, ortho, or meta to $R_1$ or $R_2$.

In another embodiment, $R_1$ or $R_2$ is —$NH_2$, the sum of p+q is 1 or 2, and the point of attachment of A and B each independently to the azo group in Formula (I) is para or ortho to $R_1$ or $R_2$.

In some embodiments, $R_1$ or $R_2$ is —$NH_2$, the sum of p+q is 1 or 2, and the point of attachment of A and B each independently to the azo group in Formula (I) is meta to $R_1$ or $R_2$.

In one embodiment, the compound has Formula (II), (III), or (IV):

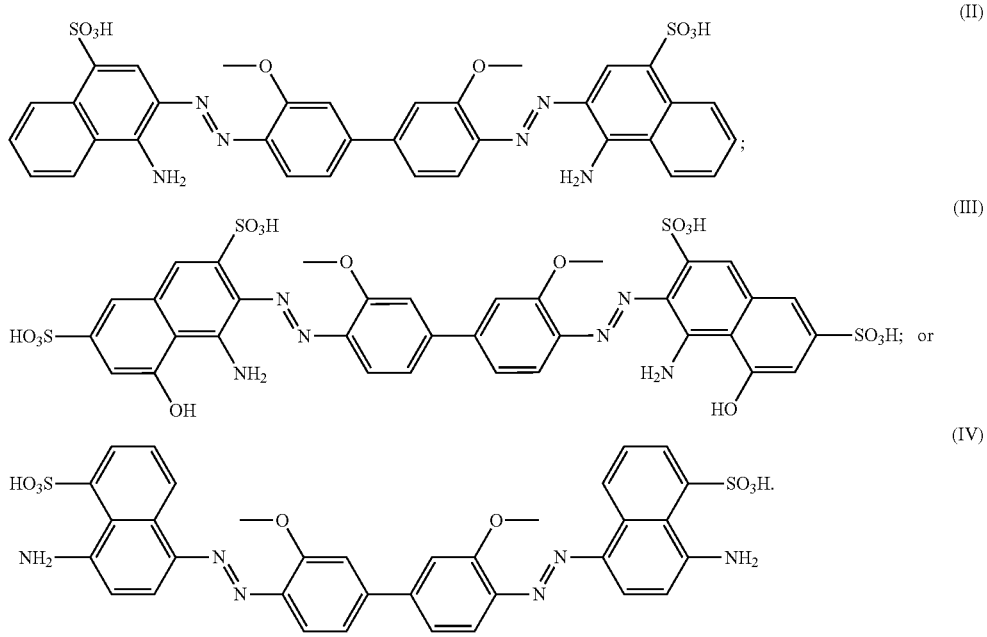

In some embodiment, the compound having Formula (I), (II), (III), or (IV) is water-soluble.

In other embodiments, the compound having Formula (I), (II), (III), or (IV) is stable at room temperature, preferably stable at room temperature for at least about 1 month. In one embodiment, the compound having Formula (I), (II), (III), or (IV) is stable at room temperature for greater than about 6 months.

In another embodiment, the compound having Formula (I), (II), (III), or (IV) can bind to a protein having a size of less than about 30 kDa. In one embodiment, the compound having Formula (I), (II), (III), or (IV) can bind to a protein having a size of greater than about 500 kDa. In other embodiments, the compound having Formula (I), (II), (III), or (IV) can bind to proteins ranging from less than 30 kDa to greater than 500 kDa.

In another aspect, the present invention provides a method for preparing a compound disclosed herein. The method comprises performing an azo coupling reaction between an aryl diazonium compound and a naphthalene derivative having a sulfonic acid group, thereby coupling the aryl diazonium compound to the naphthalene derivative to form the compound.

In one embodiment, the aryl diazonium compound is an electrophilic aryl diazonium compound.

Without wishing to be bound by any particular theory, various azo coupling reactions are known in art, for example where aryl diazonium salts couple to activated amino- or hydroxy-containing aromatic compounds, which contain strong electron donating groups (e.g., —OH or —$NH_2$) favoring the para position if available, and the ortho position if not, of the ortho-, para-director (o,p director).

Various techniques and methods for azo coupling are known to one of ordinary skill in the art and are within the scope of the invention.

In some embodiments, the reaction can be carried out in an aqueous solution. In one embodiment, the solution is a buffered solution. In another embodiment, the solution comprises water, phosphate buffered saline (PBS), or Tris-buffered saline.

In one embodiment, the azo coupling is performed at room temperature in an aqueous environment. In another embodiment, solvent can be ultrapure water or phosphate buffered saline.

In some embodiments, components are mixed at a ratio of about 1 mole aryl diazonium compound to about 0.1, about 0.5, about 1, about 2, about 3, about 4, about 5, about 6, about 7, about 8, about 9 moles, or about 10 moles naphthalene derivative.

In other embodiments, components are mixed at a ratio of about 1 mole aryl diazonium compound (e.g., about 1 mole Fast Blue B) to about 3 moles naphthalene derivative (e.g., about 3 moles Naphthionic acid) (molar excess).

In some embodiment, after azo coupling, pH of the final solution can be brought to about neutral with the addition of appropriate amount of a base sufficient to bring to about neutral e.g., added dropwise e.g., NaOH e.g., 1M NaOH.

In some embodiments, the aryl diazonium compound (e.g., a diazonium salt), as an aqueous solution or suspension, can be run or added into a solution or suspension of the naphthalene derivative component. The pH can be controlled within certain limits e.g., either by having a buffering agent present or by continuously measuring the pH with a pH meter and adding acid or alkali to maintain the pH within the prescribed limits.

In other embodiments, the naphthalene derivative component solution can be run or added into a solution or suspension of the aryl diazonium compound. The pH in this case can be controlled e.g., by a buffering agent added to the diazonium compound.

In another embodiment, the diazonium compound solution or suspension and the naphthalene derivative component solution are added together to the reaction apparatus or vessel controlling the rates normally so that the two components are always present together in the correct ratio to give complete reaction. The pH can be monitored with a pH meter and controlled by the addition of acid or alkali as required.

In one embodiment, the aryl diazonium compound is coupled to the naphthalene derivative favoring the para position if available, and the ortho position if not.

In some embodiments, the aryl diazonium compound used in this invention for the azo coupling reaction includes a diazonium salt.

Diazonium salts are commercially available from various suppliers such as, for example, Sigma-Aldrich (St. Louis, MO, USA). For example, in some embodiments, the diazonium salt known in the art as Fast Blue B (o-dianisidine bis(diazotized) zinc double salt) can be used for the azo coupling reaction. Fast Blue B has the chemical structure:

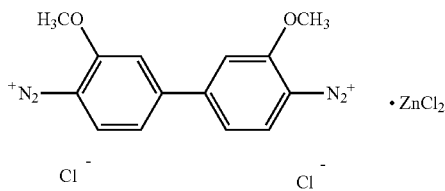

In one embodiment, the diazonium compound comprises Formula (V):

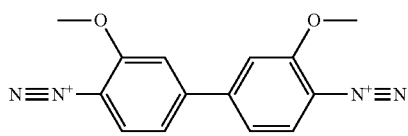

Formula (V)

In another embodiment, the azo coupling reaction comprises coupling o-dianisidine bis(diazotized) zinc double salt to the naphthalene derivative.

In other embodiments, the naphthalene derivative used in the coupling reaction has the Formula (a):

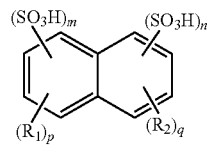

Formula (a)

wherein $R_1$ and $R_2$ each independently is —OH or —$NH_2$; m, n, p and q each independently is 0, 1, 2, 3, or 4 and the sum of m+n is not zero.

In one embodiment, the point of attachment of A and B each independently to the azo group in Formula (V) is at C1, C2, C3, C4, C5, C6, C7, or C8 of the carbon ring of Formula (a).

In another embodiment, $R_1$ or $R_2$ is an ortho-, para-director (o, p director).

In one embodiment, the sum of p+q is not zero.

In some embodiments, the sum of p+q is 1 or 2.

In another embodiment, $R_1$ or $R_2$ is —$NH_2$.

In some embodiments, $R_1$ or $R_2$ is —OH.

In other embodiments, $R_1$ or $R_2$ is —$NH_2$ and the sum of p+q is 1 or 2.

In one embodiment, the point of attachment of A and B each independently to the azo group in Formula (V) is para, ortho, or meta to $R_1$ or $R_2$.

In another embodiment, $R_1$ or $R_2$ is —$NH_2$, the sum of p+q is 1 or 2, and the point of attachment of A and B each independently to the azo group in Formula (V) is para or ortho to $R_1$ or $R_2$.

In some embodiments, $R_1$ or $R_2$ is —$NH_2$, the sum of p+q is 1 or 2, and the point of attachment of A and B each independently to the azo group in Formula (V) is meta to $R_1$ or $R_2$.

In one embodiment, the naphthalene derivative is X-amino-(Y-hydroxy)-Z-napthalenesulfonic acid. The X represents a numbered position, the Y represents one or more numbered positions, and the Z represents one or more numbered positions.

Examples of naphthalene derivatives of the general formula (a) that can be used in the azo coupling reactions of this invention include, but are not limited to, the following compounds and the salts thereof (e.g., alkali metal salts or ammonium salts thereof):

(1) Naphthalenemonosulfonic Acids: e.g., 1-Naphthalenesulfonic acid and 2-Naphthalenesulfonic acid;

(2) Naphthalenedisulfonic Acids: e.g., Naphthalene-1,5-disulfonic acid (Y-naphthalenedisulfonic acid); Naphthalene-2,6-disulfonic acid (β-naphthalenedisulfonic acid); and Naphthalene-2,7-disulfonic acid (α-naphthalenedisulfonic acid);

(3) Naphthalenetrisulfonic Acids: e.g., Naphthalene-1,3,6-trisulfonic acid;

(4) Naphtholsulfonic Acids: e.g., 1-Naphthol-2-sulfonic acid; 1-Naphthol-3-sulfonic acid; 1-Naphthol-4-sulfonic acid (NW acid); 1-Naphthol-5-sulfonic acid (L acid); 1-Naphthol-6-sulfonic acid; 1-Naphthol-7-sulfonic acid; 1-Naphthol-8-sulfonic acid; 2-Naphthol-1-sulfonic acid (oxy Tobias acid); 2-Naphthol-3-sulfonic acid; 2-Naphthol-4-sulfonic acid; 2-Naphthol-5-sulfonic acid; 2-Naphthol-6-sulfonic acid (Schäffer's acid); 2-Naphthol-7-sulfonic acid (F acid); and 2-Naphthol-8-sulfonic acid (Crocein acid);

(5) Naphtholdisulfonic Acids: e.g., 1-Naphthol-2,4-disulfonic acid; 1-Naphthol-2,5-disulfonic acid; 1-Naphthol-2,7-disulfonic acid; 1-Naphthol-3,6-disulfonic acid (Violet acid); 1-Naphthol-3,7-disulfonic acid; 1-Naphthol-3,8-disulfonic acid (& acid); 1-Naphthol-4,7-disulfonic acid; 1-Naphthol-4,8-disulfonic acid; 1-Naphthol-6,8-disulfonic acid; 2-Naphthol-1,4-disulfonic acid; 2-Naphthol-1,5-disulfonic acid; 2-Naphthol-1,6-disulfonic acid; 2-Naphthol-1,7-disulfonic acid; 2-Naphthol-3,6-disulfonic acid (R acid); 2-Naphthol-3,7-disulfonic acid; 2-Naphthol-4,8-disulfonic acid; and 2-Naphthol-6,8-disulfonic acid (G acid);

(6) Naphthol-trisulfonic Acids: e.g., 1-naphthol-2,4,7-trisulfonic acid; 1-Naphthol-2,4,8-trisulfonic acid; and 1-Naphthol-3,6,8-trisulfonic acid (oxy Koch's acid);

(7) Naphthylaminesulfonic Acids: e.g., 1-Naphthylamine-2-sulfonic acid; 1-Naphthylamine-3-sulfonic acid (Cleve's γ-acid); 1-Naphthylamine-4-sulfonic acid (naphthionic acid); 1-Naphthylamine-5-sulfonic acid (Laurent's acid); 1-Naphthylamine-6-sulfonic acid (Cleve's acid); 1-Naphthylamine-7-sulfonic acid (7-Cleve's acid); 1-Naphthylamine-8-sulfonic acid (Peri acid); 2-Naphthylamine-1-sulfonic acid (Tobias acid); 2-Naphthylamine-4-sulfonic acid; 2-Naphthylamine-5-sulfonic acid (Dahl's acid); 2-Naphthylamine-6-sulfonic acid (Brönner acid); 2-Naphthylamine-7-sulfonic acid; and 2-Naphthylamine-8-sulfonic acid (Badische acid);

(8) Naphthylamine-disulfonic Acids: e.g., 1-Naphthylamine-2,4-disulfonic acid; 1-Naphthylamine-2,5-disulfonic acid; 1-Naphthylamine-2,7-disulfonic acid; 1-Naphthylamine-2,8-disulfonic acid; 1-Naphthylamine-3,5-disulfonic acid; 1-Naphthylamine-3,6-disulfonic acid (Freund's acid); 1-Naphthylamine-3,7-disulfonic acid; 1-Naphthylamine-3,8-disulfonic acid; 1-Naphthylamine-4,6-disulfonic acid (Dahl's acid II); 1-Naphthylamine-4,7-disulfonic acid (Dahl's acid III); 1-Naphthylamine-4,8-disulfonic acid; 1-Naphthylamine-5,7-disulfonic acid; 1-Naphthylamine-5,8-disulfonic acid; 2-Naphthylamine-1,5-disulfonic acid; 2-Naphthylamine-1,6-disulfonic acid; 2-Naphthylamine-1,7-disulfonic acid; 2-Naphthylamine-3,6-disulfonic acid (amino R-acid); 2-Naphthylamine-3,7-disulfonic acid; 2-Naphthylamine-4,7-disulfonic acid; 2-Naphthylamine-4,8-disulfonic acid; 2-Naphthylamine-5,7-disulfonic acid (amino J-acid); and 2-Naphthylamine-6,8-disulfonic acid (amino G-acid);

(9) Naphthylamine-trisulfonic Acids: e.g., 1-Naphthylamine-2,4,6-trisulfonic acid; 1-Naphthylamine-2,4,7-trisulfonic acid; 1-Naphthylamine-2,5,7-trisulfonic acid; 1-Naphthylamine-3,6,8-trisulfonic acid (Koch's acid); 1-Naphthylamine-4,6,8-trisulfonic acid; and 2-Naphthylamine-3,6,8-trisulfonic acid;

(10) Dihydroxynaphthalenesulfonic Acids: e.g., 1,8-Dihydroxynaphthalene-3-sulfonic acid; 1,6-Dihydroxynaphthalene-3-sulfonic acid; 1,7-Dihydroxynaphthalene-3-sulfonic acid; 1,8-Dihydroxynaphthalene-4-sulfonic acid; 2,3-Dihydroxynaphthalene-6-sulfonic acid (dioxy R acid); and 1,7-Dihydroxynaphthalene-3-sulfonic acid (dioxy G acid);

(11) Dihydroxynaphthalenedisulfonic Acids: e.g., 1,2-Dihydroxynaphthalene-3,6-disulfonic acid; 1,3-Dihydroxynaphthalene-5,7-disulfonic acid; 1,5-Dihydroxynaphthalene-2,4-disulfonic acid; 1,8-Dihydroxynaphthalene-3,5-disulfonic acid; 1,8-Dihydroxynaphthalene-3,6-disulfonic acid (chromotropic acid); and 2,7-Dihydroxynaphthalene-3,6-disulfonic acid;

(12) Aminonaphthol-sulfonic Acids: e.g., 1-Amino-2-naphthol-4-sulfonic acid (1,2,4-acid); 1-Amino-2-naphthol-6-sulfonic acid; 5-Amino-1-naphthol-2-sulfonic acid (M-acid); 1-Amino-7-naphthol-3-sulfonic acid; 1-Amino-8-naphthol-4-sulfonic acid (S-acid); 8-Amino-1-naphthol-4-sulfonic acid; 2-Amino-3-naphthol-6-sulfonic acid; 2-Amino-5-naphthol-7-sulfonic acid (J-acid); and 2-Amino-8-naphthol-6-sulfonic acid (γ-acid);

(13) Aminonaphthol-disulfonic Acids: e.g., 1-Amino-2-naphthol-3,6-disulfonic acid; 1-Amino-8-naphthol-2,4-disulfonic acid (SS-acid); 1-Amino-8-naphthol-3,5-disulfonic acid (B-acid); 1-Amino-8-naphthol-3,6-disulfonic acid (H-acid); 1-Amino-8-naphthol-4,6-disulfonic acid (K-acid); 1-Amino-8-naphthol-5,7-disulfonic acid; 2-Amino-1-naphthol-4,8-disulfonic acid; and 2-Amino-8-naphthol-3,6-disulfonic acid (RR-acid);

(14) Naphthylenediaminesulfonic Acids: e.g., 1,2-Naphthylenediamine-3-sulfonic acid; 1,2-Naphthylenediamine-4-sulfonic acid; 1,2-Naphthylenediamine-5-sulfonic acid; 1,2-Naphthylenediamine-6-sulfonic acid; 1,2-Naphthylenediamine-7-sulfonic acid; 1,3-Naphthylenediamine-5-sulfonic acid; 1,3-Naphthylenediamine-6-sulfonic acid; 1,4-Naphthylenediamine-2-sulfonic acid; 1,4-Naphthylenediamine-5-sulfonic acid; 1,4-Naphthylenediamine-6-sulfonic acid; 1,5-Naphthylenediamine-2-sulfonic acid; 1,5-Naphthylenediamine-4-sulfonic acid; and 1,6-Naphthylenediamine-4-sulfonic acid; 1,8-Naphthylenediamine-4-sulfonic acid; and

(15) Naphthylenediaminedisulfonic Acids: e.g., 1,8-Naphthylenediamine-3,6-disulfonic acid and 1,8-Naphthylenediamine-4,5-disulfonic acid.

In one embodiment, the naphthalene derivative is a Naphthalenemonosulfonic Acid, a Naphthalenedisulfonic Acid, a Naphthalenetrisulfonic Acid, a Naphtholsulfonic Acid, a Naphtholdisulfonic Acid, a Naphthol-trisulfonic Acid, a Naphthylaminesulfonic Acid, a Naphthylamine-disulfonic Acid, a Naphthylamine-trisulfonic Acid, a Hydroxynaphthalenesulfonic Acid, a Dihydroxynaphthalenesulfonic Acid, a Hydroxynaphthalenedisulfonic Acid, a Dihydroxynaphthalenedisulfonic Acid, an Aminonaphthol-sulfonic Acid, an Aminonaphthol-disulfonic Acid, a Naphthylenediaminesulfonic Acid, or a Naphthylenediaminedisulfonic Acid.

In another embodiment, the naphthalene derivative is 4-Amino-1-naphthalenesulfonic acid, 4-Amino-5-hydroxy-2,7-naphthalenedisulfonic acid, or 1-Amino-8-naphthalenesulfonic acid.

In some embodiments, the naphthalene derivative is Naphthionic Acid.

In other embodiments, the naphthalene derivative has Formula (VI), (VII), (VIII), (IX), or (X):

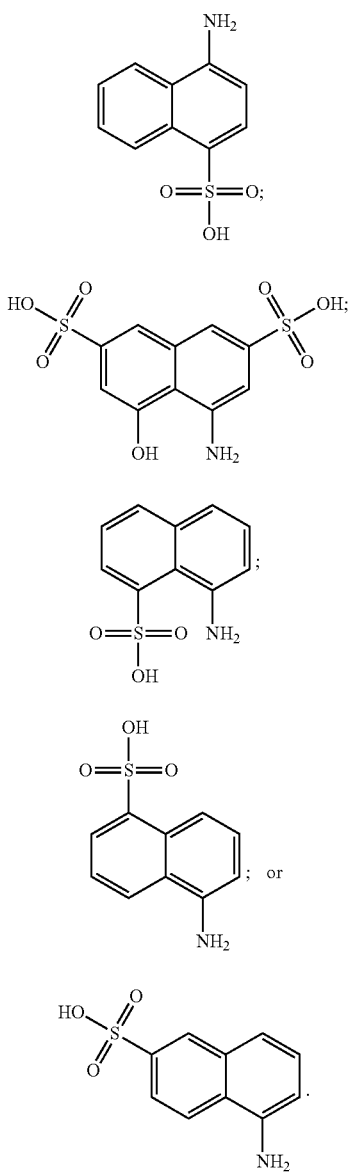

In another embodiment, the naphthalene derivative has Formula (VI), (VII), or (VIII):

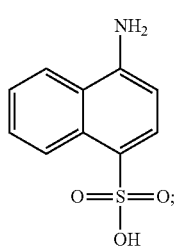

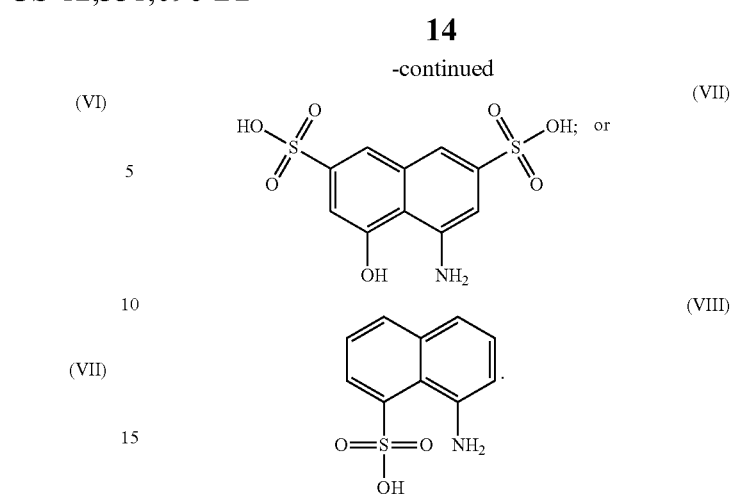

In some aspects, the present invention provides a compound prepared by a method disclosed herein. In one embodiment, the method comprises performing an azo coupling reaction between an aryl diazonium compound and a naphthalene derivative having a sulfonic acid group, whereby the aryl diazonium compound is coupled to the naphthalene derivative to form the compound. The azo coupling reaction, the diazonium compound, and the naphthalene derivative are as described herein.

In some embodiments, the compound prepared by the method has Formula (I):

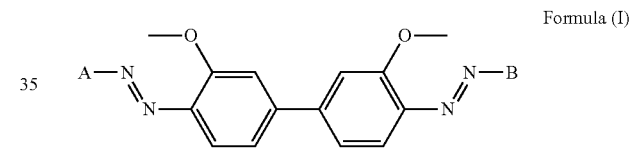

wherein A and B each independently have Formula (a),

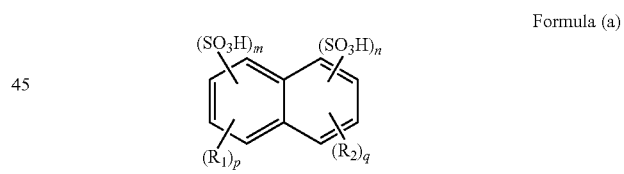

wherein $R_1$ and $R_2$ each independently is —OH or —$NH_2$; m, n, p and q each independently is 0, 1, 2, 3, or 4 and the sum of m+n is not zero.

In one embodiment, the point of attachment of A and B each independently to the azo group in Formula (I) is at C1, C2, C3, C4, C5, C6, C7, or C8 of the carbon ring of Formula (a).

In another embodiment, the sum of p+q is not zero.

In some embodiments, the sum of p+q is 1 or 2.

In another embodiment, $R_1$ or $R_2$ is —$NH_2$.

In some embodiments, $R_1$ or $R_2$ is —OH.

In other embodiments, $R_1$ or $R_2$ is —$NH_2$ and the sum of p+q is 1 or 2.

In one embodiment, the point of attachment of A and B each independently to the azo group in Formula (I) is para, ortho, or meta to $R_1$ or $R_2$.

In another embodiment, $R_1$ or $R_2$ is —$NH_2$, the sum of p+q is 1 or 2, and the point of attachment of A and B each independently to the azo group in Formula (I) is para or ortho to $R_1$ or $R_2$.

In some embodiments, $R_1$ or $R_2$ is —$NH_2$, the sum of p+q is 1 or 2, and the point of attachment of A and B each independently to the azo group in Formula (I) is meta to $R_1$ or $R_2$.

In one embodiment, the compound has Formula (II), (III), or (IV).

In some embodiment, the compound prepared by the azo coupling method described herein is water-soluble.

In other embodiments, the compound prepared by the azo coupling method described herein is stable at room temperature, preferably stable at room temperature for at least about 1 month. In one embodiment, the compound prepared by the azo coupling method described herein is stable at room temperature for greater than about 6 months.

In another embodiment, the compound prepared by the azo coupling method described herein can bind to a protein having a size of less than about 30 kDa. In one embodiment, the compound prepared by the azo coupling method described herein can bind to a protein having a size of greater than about 500 kDa. In other embodiments, the compound prepared by the azo coupling method described herein can bind to proteins ranging from less than 30 kDa to greater than 500 kDa.

In other aspects, the present invention provides a complex comprising a compound bound to a protein, wherein the compound has Formula (I) or is prepared by the azo coupling reaction method described herein.

In one embodiment, the complex comprises the compound bound to the protein, wherein the compound has Formula (I):

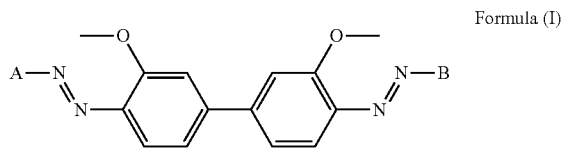

Formula (I)

wherein A and B each independently have Formula (a),

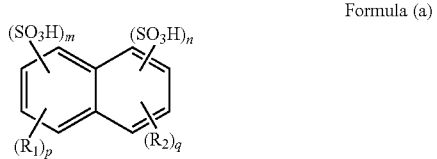

Formula (a)

wherein $R_1$ and $R_2$ each independently is —OH or —$NH_2$; m, n, p and q each independently is 0, 1, 2, 3, or 4 and the sum of m+n is not zero.

In some embodiments, the complex comprises the compound bound to the protein, wherein the point of attachment of A and B each independently to the azo group in Formula (I) is at C1, C2, C3, C4, C5, C6, C7, or C8 of the carbon ring of Formula (a).

In another embodiment, the sum of p+q is not zero.

In some embodiments, the sum of p+q is 1 or 2.

In another embodiment, $R_1$ or $R_2$ is —$NH_2$.

In some embodiments, $R_1$ or $R_2$ is —OH.

In other embodiments, $R_1$ or $R_2$ is —$NH_2$ and the sum of p+q is 1 or 2.

In one embodiment, the point of attachment of A and B each independently to the azo group in Formula (I) is para, ortho, or meta to $R_1$ or $R_2$.

In another embodiment, $R_1$ or $R_2$ is —$NH_2$, the sum of p+q is 1 or 2, and the point of attachment of A and B each independently to the azo group in Formula (I) is para or ortho to $R_1$ or $R_2$.

In some embodiments, $R_1$ or $R_2$ is —$NH_2$, the sum of p+q is 1 or 2, and the point of attachment of A and B each independently to the azo group in Formula (I) is meta to $R_1$ or $R_2$.

In one embodiment, the complex comprises the compound bound to the protein, wherein the compound has Formula (II), (III), or (IV).

In some embodiments, the protein of the complex is a folded protein e.g., in a folded or native state. The folded state of a protein refers to the native or undenatured form of the protein e.g., as it is present under physiological conditions, with secondary, tertiary and/or quaternary structures intact. Physiological conditions include conditions similar to the natural environment of the protein, or conditions under which it is stable after expression, isolation, and/or purification, i.e. before exposure to denaturing conditions.

In another embodiment, the protein is an unfolded protein e.g., in a partial or total unfolded state. The unfolded state of a protein refers to where the polypeptide has lost features of its secondary, tertiary and/or quaternary structure that are present in a folded state.

In one embodiment, the complex comprises the compound provided herein complexed with a polypeptide chain, wherein the polypeptide region complexed with the compound is on the surface of a single folded native protein, or two or more interacting proteins, and is excluded from an internal site within or between proteins where two protein polypeptide chains are in close proximity.

In another embodiment, the complex comprises a protein polypeptide chain in a native folded configuration in an aqueous environment in which two or more complexes with the compounds provided herein exist, such that the bound complexes remain following unfolding or denaturation of the protein polypeptide chain.

In one embodiment, the complex comprises the unfolded protein polypeptide chain that is bound to the complexes and is further bound to an antibody or other ligand which recognizes regions of polypeptide chain that do not contain the complexes.

In another embodiment, a protein polypeptide is provided in which the protease cleavage pattern reveals proteinase cleavage sites preferentially within the domains of the polypeptide chain that are close to protein-protein contact or binding domains within a single folded protein or between two different proteins.

In other embodiments, a protein polypeptide is provided in which the ligand binding pattern reveals domains of the polypeptide chain that are close to protein-protein contact or binding domains within a single folded protein or between two different proteins.

In other embodiments, the complex comprises a compound provided herein bound to the folded or unfolded protein, wherein the compound binds with high affinity to the majority (if not all) of the protease cleavage consensus sites on the protein, thus achieving the capability of "painting" the entire exposed surface of the folded or unfolded protein. In one embodiment, the protease is trypsin and the consensus cleavage site comprises a trypsin cleavage site.

In another embodiment, the complex comprises a compound provided herein bound to the folded or unfolded protein, wherein the compound binds to the protein with very high affinity with a high on-rate (e.g., $K_D<10^{-10}$ M) and a low off rate. This insures that the protein painting is stable and can remain adherent following partial or complete unfolding or linearization of the protein polypeptide chain.

In some embodiments, the complex comprises a compound provided herein bound to the protein, wherein the compound remains adherent to the protein molecule after exposure to levels of denaturant or detergent treatments that can dissociate binding partners e.g., protein-protein binding partners.

In one embodiment, the bound compounds prevent protease (e.g., trypsin) cleavage at a location at or near the compound binding site.

In other embodiments, the complex comprises a compound provided herein bound to the protein, wherein the compound binds to the protein surface in solution but is excluded from internal interaction domains that are hidden from the surface. In some embodiments, unpainted binding domains remain exposed and ready for any type of structural or functional analysis.

In some embodiments, each type of compound can bind to regions of the protein surface using similar or different mechanisms for each type of compound or "paint." For example, some compounds may prefer hydrophobic sites while others may prefer hydrophilic or anionic or cationic regions.

In one embodiment, the complex comprises full coverage of all the exposed regions of the protein or blocking of all the protease cleavage sites or all the ligand binding sites of the protein.

In some embodiments, the complex can comprise two or more structurally different compounds each bound to a protein.

In one embodiment, the two or more structurally different compounds each independently has Formula (I) or is prepared by the azo coupling reaction method described herein.

In some embodiments, the two or more structurally different compounds each independently has Formula (I):

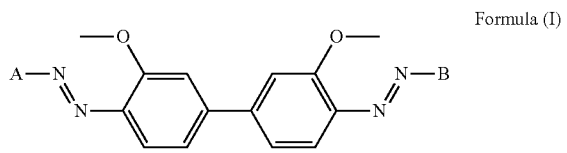

Formula (I)

wherein A and B each independently have Formula (a),

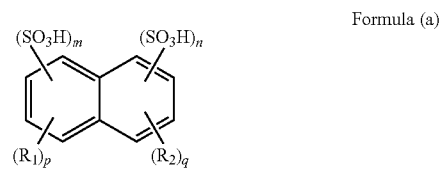

Formula (a)

wherein $R_1$ and $R_2$ each independently is —OH or —$NH_2$; m, n, p and q each independently is 0, 1, 2, 3, or 4 and the sum of m+n is not zero.

In other embodiments, the two or more structurally different compounds each independently has Formula (I), wherein the point of attachment of A and B each independently to the azo group in Formula (I) is at C1, C2, C3, C4, C5, C6, C7, or C8 of the carbon ring of Formula (a).

In another embodiment, the two or more structurally different compounds each independently has Formula (I), wherein the sum of p+q is not zero.

In some embodiments, the two or more structurally different compounds each independently has Formula (I), wherein the sum of p+q is 1 or 2.

In another embodiment, the two or more structurally different compounds each independently has Formula (I), wherein $R_1$ or $R_2$ is —$NH_2$.

In some embodiments, the two or more structurally different compounds each independently has Formula (I), wherein $R_1$ or $R_2$ is —OH.

In other embodiments, the two or more structurally different compounds each independently has Formula (I), wherein $R_1$ or $R_2$ is —$NH_2$ and the sum of p+q is 1 or 2.

In one embodiment, the two or more structurally different compounds each independently has Formula (I), wherein the point of attachment of A and B each independently to the azo group in Formula (I) is para, ortho, or meta to $R_1$ or $R_2$.

In another embodiment, the two or more structurally different compounds each independently has Formula (I), wherein $R_1$ or $R_2$ is —$NH_2$, the sum of p+q is 1 or 2, and the point of attachment of A and B each independently to the azo group in Formula (I) is para or ortho to $R_1$ or $R_2$.

In some embodiments, the two or more structurally different compounds each independently has Formula (I), wherein $R_1$ or $R_2$ is —$NH_2$, the sum of p+q is 1 or 2, and the point of attachment of A and B each independently to the azo group in Formula (I) is meta to $R_1$ or $R_2$.

In one embodiment, the two or more structurally different compounds each independently has Formula (II), (III), or (IV).

In another embodiment, the complex comprises a compound having Formula (I) and a compound having Formula (II) each bound to the protein.

In some embodiments, the complex comprises a compound having Formula (I) and a compound having Formula (III) each bound to the protein.

In other embodiments, the complex comprises a compound having Formula (II) and a compound having Formula (III) each bound to the protein.

In another embodiment, the complex comprises a compound having Formula (II), a compound having Formula (III), and a compound having Formula (IV) each bound to the protein.

In some embodiments, the complex can comprise two or more structurally different compounds each bound to a protein, wherein at least one compound has Formula (I) or is prepared by the azo coupling reaction method described herein.

In one embodiment, the complex comprises two or more structurally different compounds each bound to a protein, wherein at least one compound has Formula (I) or is prepared by the azo coupling reaction method described herein, wherein the complex further comprises one or more compounds, wherein the one or more compounds each does not have Formula (I). In some embodiments, the one or more compounds each is bound to the protein. In other embodiments, at least one of the one or more compounds is bound to the protein.

In other embodiments, the one or more compounds each is a dye capable of binding to a protein.

In some embodiments, the one or more compounds each is an aryl hydrocarbon containing organic compounds less than 30 Angstroms in total length. Examples of aryl hydrocarbon containing organic compounds less than 30 Angstroms in total length include, without limitation, polymethine compounds, triarylmethane compounds, naphthalene derivatives, aryl azo compounds, anthraquinones, xanthenes, and thiazines such as, for example, those disclosed in U.S. Pat. No. 10,126,304, which is herein incorporated by reference in its entirety.

In other embodiments, the aryl hydrocarbon containing organic compounds less than 30 Angstroms in total length has the following structure formula:

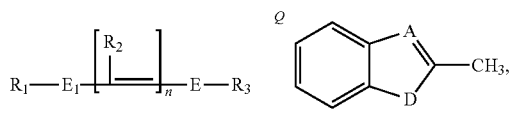
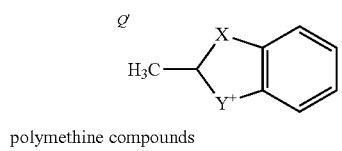

polymethine compounds wherein $R_1$ represents H, O, halo, CO2H, NO2, SH, NR5R6, C1-6 alkyl, C1-6 alkoxy, cyano, carbonyl, pyrrolidinyl, pyrrolyl, pyrazolyl, imidazolyl, triazolyl, etc.; R5, R6 represent H, C1-4 alkyl; E1 represents benzene ring or ring Q; A represents CH or N; D represents S, NH, N—C1-3 alkyl, O, or CH2; R2 represents H, C1-4 alkyl, halo-C1-4 alkyl, HO, cyano; n represents an integer of 1-4; E=benzene ring or ring Q'; X represents CH or N; Y represents S, NH, N—C1-3 alkyl, O, or CH2; R3═H, O, halo, CO2H, NO2, SH, NR5R6, C1-6 alkyl, C1-6 alkoxy, cyano, carbonyl, pyrrolidinyl, pyrrolyl, pyrazolyl, imidazolyl, triazolyl, etc.);

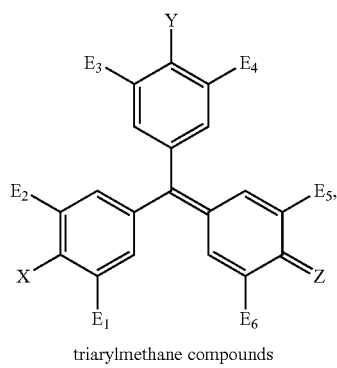

triarylmethane compounds wherein X, Y, Z represent H, NR1R2, sulfa, O, halo, CO2H, NO2, SH, C1-6 alkyl, C1-6 alkoxy, etc.; R1, R2 represent H, C1-6 alkyl, sulfophenyl; E1, E2, E3, E4, E5, E6 represent H, sulfa, C1-6 alkyl, halo, CO2H, NO2, SH;

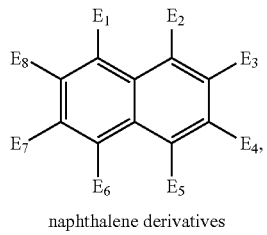

naphthalene derivatives wherein E1, E2, E3, E4, E5, E6 represent H, O, C1-6 alkyl, C1-6 alkoxy, carbonyl, sulfo, NO2, NR1R2, azetidinyl, thiazolidinyl; R1, R2 represent H, phenyl;

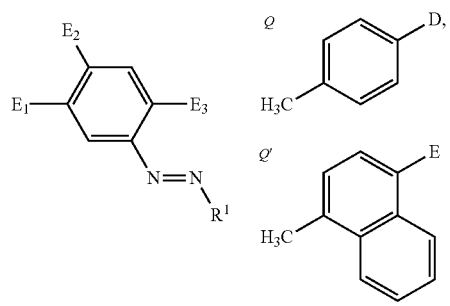

aryl azo compounds wherein E1, E2, E3 represent H, halo, sulfo, O, C1-6 alkyl, C1-6 alkyl aryl; R1 represents ring Q or ring Q'; D represents H, NR2R3; R2, R3 represent C1-6 alkyl, C1-6 alkyl aryl; E represents H, O, OH, C1-6 alkyloxy;

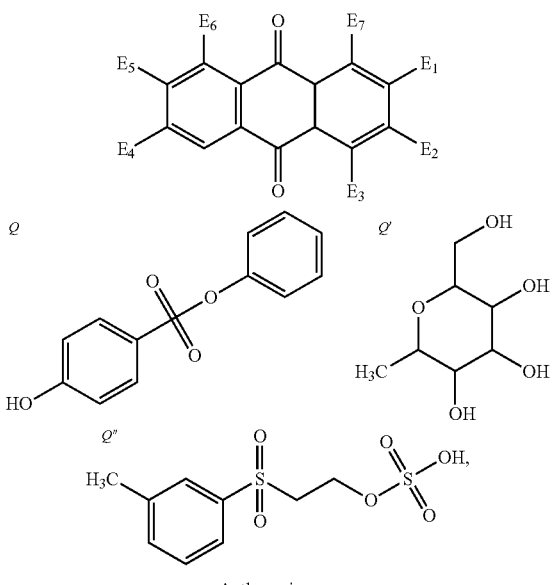

Anthraquinones wherein E1 represents H, NH, sulfo, Q, Q', C1-6 alkyl, OH, carboxy; E2 represents H, NH, OH, C1-6 alkyl, sulfo; E3 represents H, NH, OH, NR1R2, sulfo, C1-6 alkyl; R1, R2 represent H, Q"; E4, E5, E6, E7 represent H, OH, NH, sulfa, C1-6 alkyl, carboxy;

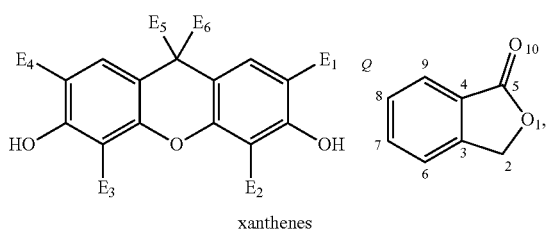

xanthenes wherein E1, E2, E3, E4 represent H, NO2, OH, Halo, C1-6 alkyl; E5, E6 represent H or Carbon in position 3 and oxygen in position 1 in group Q; or

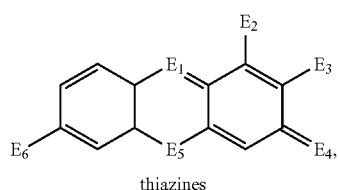

thiazines wherein E1 represents N, O, S; E2, E3 represent H, C in aryl; E4 represents O, N, NR1R2; R1, R2 represent C1-6 alkyl; E5 represents N, O, S; E6 represents H, NH, NC1-6 alkyl.

In one embodiment, the one or more compounds includes but is not limited to Acid Orange 50 (AO50, CAS 10214-07-0), Trypan Blue (TB, CAS 72-57-1), Direct Blue 199 (DB199, CAS 12222-04-7), Alcian Blue (6), Alizarin Blue Black B (ABB), Disperse Blue 3 (DB3), Remazol Brilliant Blue R (RBB), phenyl 4-[(1-amino-4-hydroxy-9,10-dioxo-9,10-dihydro-2-anthracenyl)oxy]benzenesulphonate (R49), 8-Anilino-1-naphthalenesulfonic acid (ANSA), Pigment Red 177 (PR1), Acid Black 48 (AB4), Disperse Yellow 3 (DB3), Acid Black 1 (AB1), Disperse Orange 3 (DO3), Disperse Yellow 9 (DY9), Rhodamine 123 (R12), Toluidine Blue O (TBO), Pararosaniline Base (PR), Brilliant Blue R-250 (BB), Acid Blue 22 (AB2), Cibacron Blue F3GA (CB), Acrylic Acid (AAc), and Vinyl Sulfonic Acid (VSA) as well as the organic compounds listed in Tables 1 and 2.

TABLE 1

Organic compounds

| Name | Formula |
|---|---|
| Pinacyanol chloride | |
| 1,1'-Diethyl-4,4'-cyanine iodide | |
| Fluorescein | |
| 3,3'-Diethylthiadicarbocyanine iodide | |

TABLE 1-continued
Organic compounds
| Name | Formula |
|---|---|
| Nile Red | 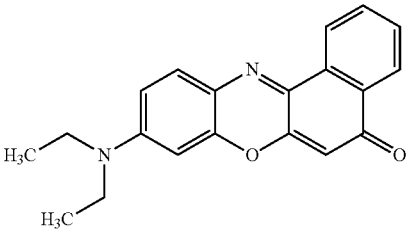 [SMILES: CCN(CC)c1ccc2nc3c4ccccc4c(=O)cc-3oc2c1] |
| Thioflavin T | 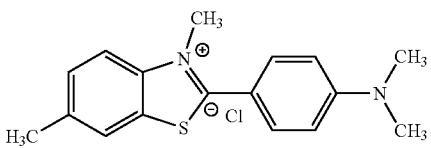 |
| 8-Anilino-1-naphthalenesulfonic acid | 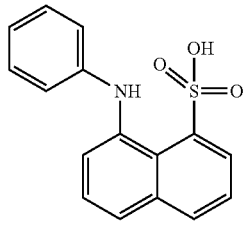 [SMILES: O=S(=O)(O)c1cccc2cccc(Nc3ccccc3)c12] |
| 4,4'-Dianilino-1,1'-binaphthyl-5,5'-disulfonic acid dipotassium salt | 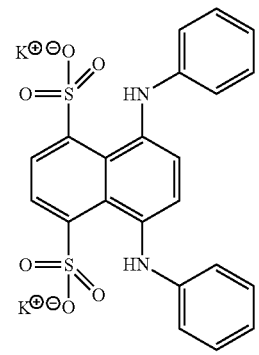 [SMILES: [K+] ; [K+] ; O=S(=O)([O-])c1ccc(S(=O)(=O)[O-])c2c(Nc3ccccc3)ccc(Nc3ccccc3)c12] |
| Orange G | 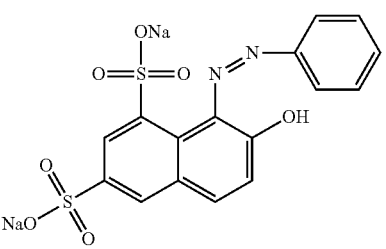 |
| sodium 4-[(4-methoxy-1-naphthyl)diazenyl]benzenesulfonate | 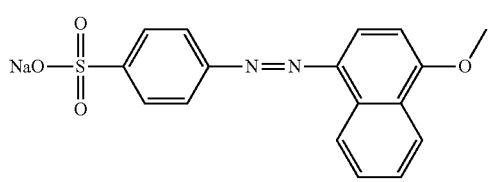 |

TABLE 1-continued

Organic compounds

| Name | Formula |
|---|---|
| Phenyl 4-[(1-amino-4-hydroxy-9,10-dioxo-9,10-dihydro-2-anthracenyl)oxy]benzenesulfonate | |
| Sodium 4-(4-(benzyl-et-amino)-ph-azo)-2,5-di-cl-benzenesulfonate | |
| Ethyl Orange sodium salt | |
| Orange II sodium salt | |
| Crocein MOO | |

TABLE 1-continued

| Organic compounds | |
|---|---|
| Name | Formula |
| Copper phthalocyanine tetrasulfonic acid tetrasodium salt | *structure of copper phthalocyanine tetrasulfonic acid tetrasodium salt* |
| Xanthene | *structure of xanthene* |
| Eosin B | *structure of Eosin B* |
| Eosin Y | *structure of Eosin Y* |
| Congo Red | *structure of Congo Red* |

TABLE 1-continued

Organic compounds

| Name | Formula |
|---|---|
| Methyl Blue | |
| Acid Fuchsin | |
| Methyl violet | |
| Aniline Blue diammonium salt | |

TABLE 1-continued

Organic compounds

| Name | Formula |
|---|---|
| Azure A chloride | [structure] |
| Carmine | [structure] |
| Remazol Brilliant Blue R | [structure] |

TABLE 2

Organic compounds

| Class | CAS no. | Name/Formula |
|---|---|---|
| Anthraquinone | 5517-38-4 | [structure]<br>phenyl 4-[(1-amino-4-hydroxy-9,10-dioxo-9,10-dihydro-2-anthracenyl)oxy]benzenesulfonate |
| Anthraquinone | 1390-65-4 | [structure]<br>3,5,6,8-tetrahydroxy-1-methyl-9,10-dioxo-7-[3,4,5-trihydroxy-6-(hydroxymethyl)oxan-2-yl]anthracene-2-carboxylic acid |

TABLE 2-continued

Organic compounds

| Class | CAS no. | Name/Formula |
|---|---|---|
| Anthraquinone | 2580-78-1 | 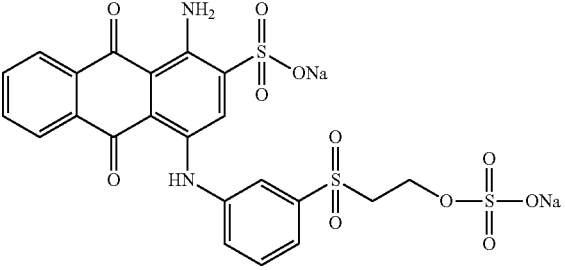<br>disodium; 1-amino-9, 10-dioxo-4-[3-(2-sulfonatooxyethylsulfonyl)anilino]anthracene-2-sulfonate |
| Aryl azo compound | 10214-07-0 | 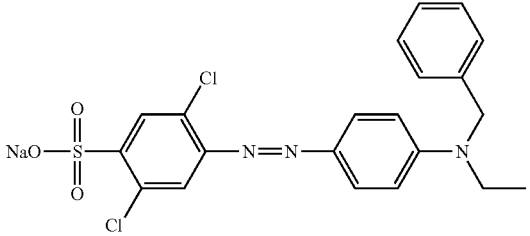<br>Sodium 4-(4-(benzyl-et-amino)-ph-azo)-2,5-di-cl-benzenesulfonate |
| Aryl azo compound | 68806-22-4 | 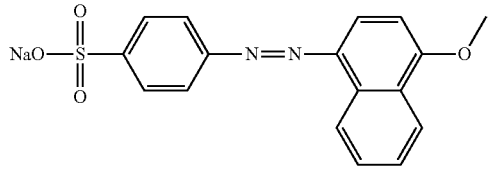<br>Sodium 4-[(4-methoxy-1-naphthyl)diazenyl]benzenesulfonate |
| Aryl azo compound | 573-58-0 | 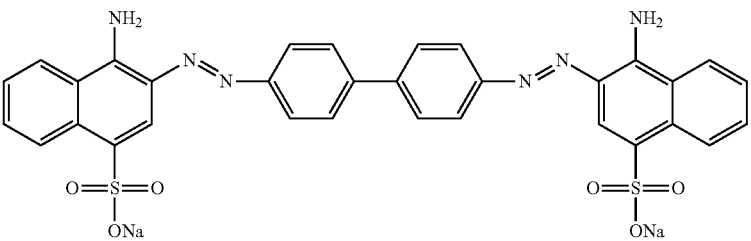<br>disodium;4-amino-3-[[4-[4-[(1-amino-4-sulfonatonaphthalen-2-yl)diazenyl] phenyl]phenyl]diazenyl]naphthalene-1-sulfonate |
| Aryl azo compound | 1936-15-8 | 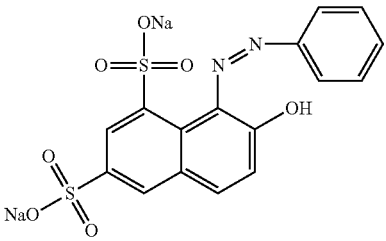<br>7-Hydroxy-8-phenylazo-1,3-naphthalenedisulfonic acid disodium salt |

TABLE 2-continued

| Class | CAS no. | Name/Formula |
|---|---|---|
| Xanthene | 2321-07-5 | 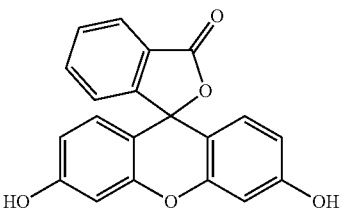 [SMILES: O=C1OC2(c3ccc(O)cc3Oc3cc(O)ccc32)c2ccccc21]<br>3',6'-dihydroxy-Spiro[isobenzofuran-1(3H),9'-[9H]xanthen]-3-one |
| Xanthene | 92-83-1 | 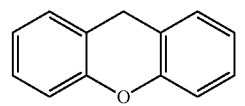 [SMILES: c1ccc2c(c1)Cc1ccccc1O2]<br>Xanthene |
| Xanthene | 548-24-3 | 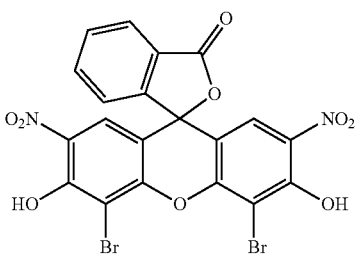 [SMILES: O=C1OC2(c3ccccc31)c1cc([N+](=O)[O-])c(O)c(Br)c1Oc1c2cc([N+](=O)[O-])c(O)c1Br]<br>4',5'-dibromo-3',6'-dihydroxy-2',7'-dinitro- spiro[isobenzofuran-1(3H),9'-[9H]xanthen]-3-one |
| Thiazine | 531-53-3 | 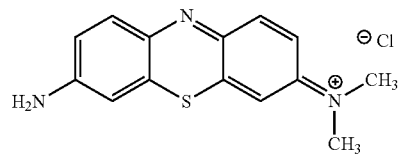 [SMILES: C[N+](C)=c1ccc2nc3ccc(N)cc3sc-2c1 ; [Cl-]]<br>3-amino-7-(dimethylamino)-Phenothiazin-5-ium, chloride |
| Triarylmethane compound | 8004-87-3 | 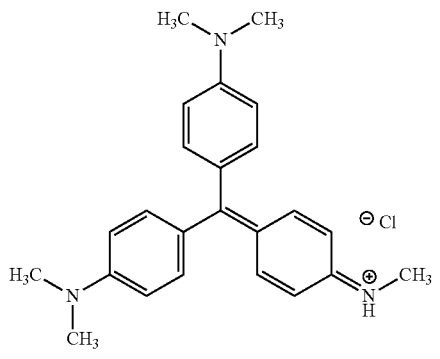<br>N-(4-{bis[4-(dimethylamino)phenyl]methylene}-2,5-cyclohexadien-1-ylidene)methanaminium chloride |

TABLE 2-continued

Organic compounds

| Class | CAS no. | Name/Formula |
|---|---|---|
| Triarylmethane compound | 28983-56-4 | [4-[bis[4-[(sulfophenyl)amino]phenyl]methylene]-2,5-cyclohexadien-1-ylidene]amino]-Benzenesulfonic acid, sodium salt (1:2) |
| Triarylmethane compound | 3244-88-0 | 2-amino-5-[(4-amino-3-sulfophenyl)(4-imino-3-sulfo-2,5-cyclohexadien-1-ylidene)methyl]-3-methyl-Benzenesulfonic acid, sodium salt |
| Polymethine compound | 905-97-5 | 3,3'-Diethylthiacarbocyanine iodide |
| Polymethine compound | 23302-83-2 | 4-[2-(1-methyl-4(1H)-pyridinylidene)ethylidene]-2,5-Cyclohexadien-1-one, |

TABLE 2-continued

| | Organic compounds | |
|---|---|---|
| Class | CAS no. | Name/Formula |
| Polymethine compound | 2768-90-3 | 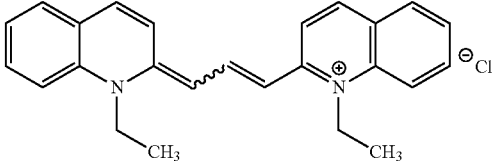 [SMILES: CCN1C(=CC=Cc2ccc3ccccc3[n+]2CC)C=Cc2ccccc21 ; [Cl-]]<br>(2E)-1-ethyl-2-[(E)-3-(1-ethylquinolin-1-ium-2-yl)prop-2-enylidene] quinoline; chloride |
| Polymethine compound | 4727-49-5 | 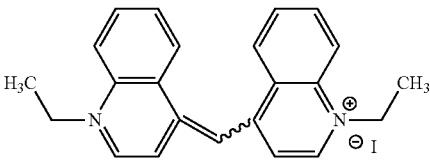<br>1,1'-Diethyl-4,4'-cyanine iodide |
| Polymethine compound | 514-73-8 | 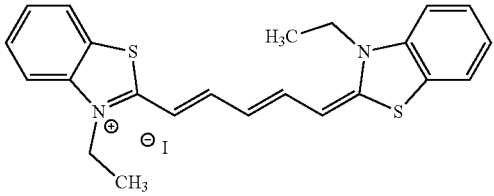 [SMILES: CCN1\C(=C/C=C/C=C/c2sc3ccccc3[n+]2CC)Sc2ccccc21 ; [I-]]<br>3-Ethyl-2-[5-(3-ethyl-2(3H)-benzothiazolylidene)-1,3-pentadienyl]benzothiazolium iodide |
| Naphthalene derivative | 82-76-8 | 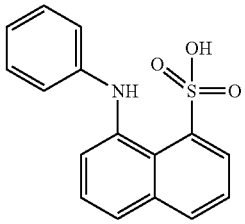 [SMILES: O=S(=O)(O)c1cccc2cccc(Nc3ccccc3)c12]<br>8-Anilino-1-naphthalenesulfonic acid |
| Naphthalene derivative | 65664-81-5 | 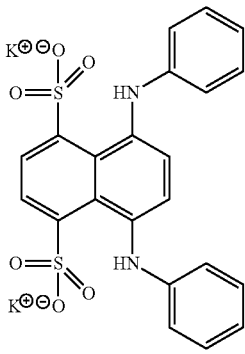 [SMILES: [K+] ; [K+] ; O=S(=O)([O-])c1ccc(S(=O)(=O)[O-])c2c(Nc3ccccc3)ccc(Nc3ccccc3)c12]<br>4,4'-Dianilino-1,1'-binaphthyl-5,5'-disulfonic acid dipotassium salt |

TABLE 2-continued

Organic compounds

| Class | CAS no. | Name/Formula |
|---|---|---|
| Heterocyclic compound | 2390-54-7 | 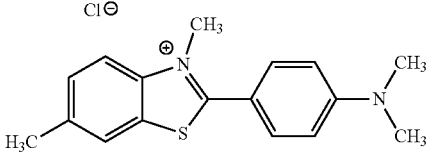<br>Thioflavine T |
| Heterocyclic compound | 2390-54-7 | 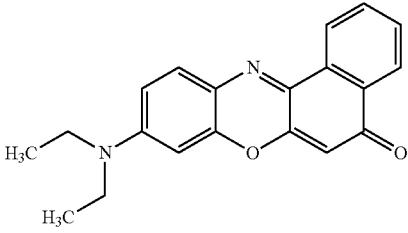 [SMILES: CCN(CC)c1ccc2nc3c4ccccc4c(=O)cc-3oc2c1]<br>2-[4-(dimethylamino)phenyl]-3,6-dimethyl-Benzothiazolium, chloride |

In one embodiment, the second compound is a dye.

In another embodiment, the one or more compounds is disodium 1-amino-9,10-dioxo-4-[3-(2-sulphonatooxyethyl-sulphonyl) anilino] anthracene-2-sulphonate (RBB); sodium 4-(4-(benzyl-et-amino)-ph-azo)-2,5-di-cl-benzenesulphonate (AO50); phenyl 4-[(1-amino-4-hydroxy-9,10-dioxo-9,10-dihydro-2-anthracenyl)oxy]benzenesulphonate (R49); or 8-Anilino-1-naphthalenesulfonic acid (ANSA).

In some embodiment, the one or more compounds is Acid Orange 50 (AO50, CAS 10214-07-0).

In other embodiments, the present invention provides a protein polypeptide chain in a native folded configuration in an aqueous environment in which two or more complexes with one or more compounds exist, such that the bound complexes remain following unfolding or denaturation of the protein polypeptide chain, where the one or more compounds comprises the compound having Formula (I) or prepared by the azo coupling method described herein.

In one embodiment, the present invention provides an unfolded protein in complex with a compound, wherein the unfolded protein has been cleaved by a protease such that the proteinase cleavage pattern is modified by bound complexes, wherein the compound comprises Formula (I) or is prepared by the azo coupling method described herein.

In some embodiments, the protease is trypsin, Arg-C proteinase, Asp-N endopeptidase, Caspase1, Caspase2, Caspase3, Caspase4, Caspase5, Caspase6, Caspase7, Caspase8, Caspase9, Caspase10, Chymotrypsin, Clostripain (Clostridiopeptidase B), Enterokinase, Factor Xa, Glutamyl endopeptidase, GranzymeB, LysC, LysN, Pepsin, Proline-endopeptidase, Proteinase K, Staphylococcal peptidase I, Tobacco etch virus protease, Thermolysin, or Thrombin.

In other embodiment, the unfolded protein polypeptide chain is further bound to an antibody or other ligand which recognizes regions of polypeptide chain that do not contain the complexes.

In another aspect, the present invention provides a composition comprising a compound, wherein the compound has Formula (I) or is prepared by the azo coupling reaction method described herein.

In one embodiment, the composition comprises the compound having Formula (I):

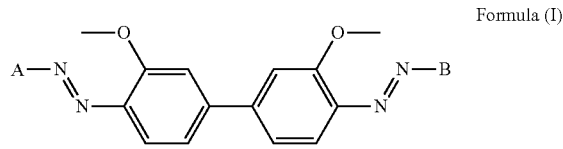

Formula (I)

wherein A and B each independently have Formula (a),

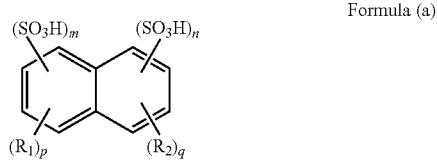

Formula (a)

wherein $R_1$ and $R_2$ each independently is —OH or —NH$_2$; m, n, p and q each independently is 0, 1, 2, 3, or 4 and the sum of m+n is not zero.

In some embodiments, the composition comprises the compound, wherein the point of attachment of A and B each independently to the azo group in Formula (I) is at C1, C2, C3, C4, C5, C6, C7, or C8 of the carbon ring of Formula (a).

In another embodiment, the sum of p+q is not zero.

In some embodiments, the sum of p+q is 1 or 2.

In another embodiment, $R_1$ or $R_2$ is —NH$_2$.

In some embodiments, $R_1$ or $R_2$ is —OH.

In other embodiments, $R_1$ or $R_2$ is —NH$_2$ and the sum of p+q is 1 or 2.

In one embodiment, the point of attachment of A and B each independently to the azo group in Formula (I) is para, ortho, or meta to $R_1$ or $R_2$.

In another embodiment, $R_1$ or $R_2$ is $-NH_2$, the sum of p+q is 1 or 2, and the point of attachment of A and B each independently to the azo group in Formula (I) is para or ortho to $R_1$ or $R_2$.

In some embodiments, $R_1$ or $R_2$ is $-NH_2$, the sum of p+q is 1 or 2, and the point of attachment of A and B each independently to the azo group in Formula (I) is meta to $R_1$ or $R_2$.

In one embodiment, the composition comprises the compound, wherein the compound has Formula (II), (III), or (IV).

In some embodiments, the composition can comprise the two or more structurally different compounds.

In one embodiment, the two or more structurally different compounds each independently has Formula (I) or is prepared by the azo coupling reaction method described herein.

In some embodiments, the two or more structurally different compounds each independently has Formula (I):

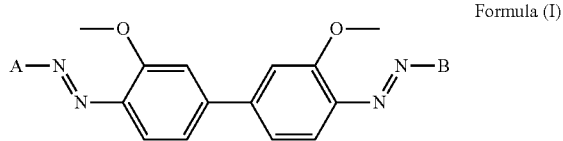

Formula (I)

wherein A and B each independently have Formula (a),

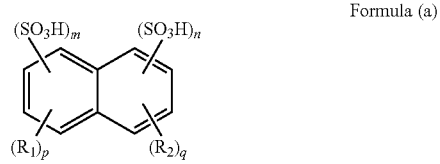

Formula (a)

wherein $R_1$ and $R_2$ each independently is $-OH$ or $-NH_2$; m, n, p and q each independently is 0, 1, 2, 3, or 4 and the sum of m+n is not zero.

In other embodiments, the two or more structurally different compounds each independently has Formula (I), wherein the point of attachment of A and B each independently to the azo group in Formula (I) is at C1, C2, C3, C4, C5, C6, C7, or C8 of the carbon ring of Formula (a).

In another embodiment, the two or more structurally different compounds each independently has Formula (I), wherein the sum of p+q is not zero.

In some embodiments, the two or more structurally different compounds each independently has Formula (I), wherein the sum of p+q is 1 or 2.

In another embodiment, the two or more structurally different compounds each independently has Formula (I), wherein $R_1$ or $R_2$ is $-NH_2$.

In some embodiments, the two or more structurally different compounds each independently has Formula (I), wherein $R_1$ or $R_2$ is $-OH$.

In other embodiments, the two or more structurally different compounds each independently has Formula (I), wherein $R_1$ or $R_2$ is $-NH_2$ and the sum of p+q is 1 or 2.

In one embodiment, the two or more structurally different compounds each independently has Formula (I), wherein the point of attachment of A and B each independently to the azo group in Formula (I) is para, ortho, or meta to $R_1$ or $R_2$.

In another embodiment, the two or more structurally different compounds each independently has Formula (I), wherein $R_1$ or $R_2$ is $-NH_2$, the sum of p+q is 1 or 2, and the point of attachment of A and B each independently to the azo group in Formula (I) is para or ortho to $R_1$ or $R_2$.

In some embodiments, the two or more structurally different compounds each independently has Formula (I), wherein $R_1$ or $R_2$ is $-NH_2$, the sum of p+q is 1 or 2, and the point of attachment of A and B each independently to the azo group in Formula (I) is meta to $R_1$ or $R_2$.

In one embodiment, the two or more structurally different compounds each independently has Formula (II), (III), or (IV).

In another embodiment, the composition comprises a compound having Formula (I) and a compound having Formula (II) each bound to the protein.

In some embodiments, the composition comprises a compound having Formula (I) and a compound having Formula (III) each bound to the protein.

In other embodiments, the composition comprises a compound having Formula (II) and a compound having Formula (III) each bound to the protein.

In another embodiment, the composition comprises a compound having Formula (II), a compound having Formula (III), and a compound having Formula (IV) each bound to the protein.

In some embodiments, the composition can comprise two or more structurally different compounds each bound to a protein, wherein at least one compound has Formula (I) or is prepared by the azo coupling reaction method described herein.

In one embodiment, the composition comprises two or more structurally different compounds each bound to a protein, wherein at least one compound has Formula (I) or is prepared by the azo coupling reaction method described herein, wherein the composition further comprises the one or more compounds, wherein the one or more compounds each does not have Formula (I).

In other embodiments, the one or more compounds each is capable of binding to a protein.

In some embodiments, the one or more compounds each is an aryl hydrocarbon containing organic compounds less than 30 Angstroms in total length. Examples of aryl hydrocarbon containing organic compounds less than 30 Angstroms in total length include, without limitation, polymethine compounds, triarylmethane compounds, naphthalene derivatives, aryl azo compounds, anthraquinones, xanthenes, and thiazines such as, for example, those disclosed in U.S. Pat. No. 10,126,304, which is herein incorporated by reference in its entirety.

In one embodiment, the one or more compounds includes but is not limited to Acid Orange 50 (AO50, CAS 10214-07-0), Trypan Blue (TB, CAS 72-57-1), Direct Blue 199 (DB199, CAS 12222-04-7), Alcian Blue (6), Alizarin Blue Black B (ABB), Disperse Blue 3 (DB3), Remazol Brilliant Blue R (RBB), phenyl 4-[(1-amino-4-hydroxy-9,10-dioxo-9,10-dihydro-2-anthracenyl)oxy]benzenesulphonate (R49), 8-Anilino-1-naphthalenesulfonic acid (ANSA), Pigment Red 177 (PR1), Acid Black 48 (AB4), Disperse Yellow 3 (DB3), Acid Black 1 (AB1), Disperse Orange 3 (DO3), Disperse Yellow 9 (DY9), Rhodamine 123 (R12), Toluidine Blue O (TBO), Pararosaniline Base (PR), Brilliant Blue R-250 (BB), Acid Blue 22 (AB2), Cibacron Blue F3GA (CB), Acrylic Acid (AAc), and Vinyl Sulfonic Acid (VSA) as well as the organic compounds listed in Tables 1 and 2.

In one aspect, the present invention provides a kit comprising a compound, wherein the compound has Formula (I)

or is prepared by the azo coupling reaction method described herein, wherein the kit further comprises an instruction for using the kit.

In another aspect, the present invention provides a kit comprising a first container comprising an aryl diazonium compound, a second container comprising a naphthalene derivative having a sulfonic acid group, and an instruction e.g., instruction for performing an azo coupling reaction between the diazonium compound and the naphthalene derivative.

In some embodiments, the aryl diazonium compound and the naphthalene derivative are as described herein.

In other embodiments, the first container comprises o-dianisidine bis(diazotized) zinc double salt.

In one embodiment, the second container comprises the naphthalene derivative, wherein the naphthalene derivative has the Formula (a):

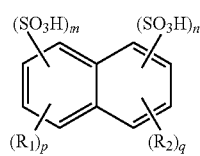

Formula (a)

wherein $R_1$ and $R_2$ each independently is —OH or —$NH_2$; m, n, p and q each independently is 0, 1, 2, 3, or 4 and the sum of m+n is not zero.

In some embodiments, the naphthalene derivative is X-amino-(Y-hydroxy)-Z-napthalenesulfonic acid, wherein the X represents a numbered position, the Y represents one or more numbered positions, and the Z represents one or more numbered positions.

In other embodiments, the naphthalene derivative is a naphthalenemonosulfonic acid, a naphthalenedisulfonic acid, a naphthalenetrisulfonic acid, a naphtholsulfonic acid, a naphtholdisulfonic acid, a naphthol-trisulfonic acid, a naphthylaminesulfonic acid, a naphthylamine-disulfonic acid, a naphthylamine-trisulfonic acid, a hydroxynaphthalenesulfonic acid, a dihydroxynaphthalenesulfonic acid, a hydroxynaphthalenedisulfonic acid, a dihydroxynaphthalenedisulfonic acid, an aminonaphthol-sulfonic acid, an aminonaphthol-disulfonic acid, a naphthylenediaminesulfonic acid, or a naphthylenediaminedisulfonic acid.

In one embodiment, the naphthalene derivative is 4-Amino-1-naphthalenesulfonic acid, 4-Amino-5-hydroxy-2,7-naphthalenedisulfonic acid, or 1-Amino-8-naphthalenesulfonic acid.

In another embodiment, the naphthalene derivative has Formula (VI), (VII), (VIII), (IX), or (X).

In other embodiments, the naphthalene derivative has Formula (VI), (VII), or (VIII).

In some aspects, the present invention provides a method for determining an interaction site of a protein. The method comprises contacting the protein with a compound to form a complex with the compound at an accessible region of the protein that is accessible by the compound; and determining an inaccessible region of the protein that is not accessible by the compound, thereby determining the interaction site, wherein the compound has Formula (I) or is prepared by the azo coupling reaction method described herein.

Accordingly, in some embodiments, the present invention provides a novel panel of synthetic organic small molecules of Formula (I) (or as prepared by the azo coupling reaction method described herein) that bind to protein molecules and mask protease cleavage sites of the protein. For example, in one embodiment, interacting native proteins in solution can be painted with the compounds described herein that can be employed as so-called "paint" or "masking" molecules/pigments/paints that coat the exposed surfaces of the proteins but do not have access to the internal protein-binding partner (e.g., protein-protein) contact domains. Thus, in such an embodiment, if a native protein and its binding partner (e.g., two native proteins) are bound together, the interface domain(s) will remain "non-painted." In some embodiments, the compounds disclosed herein can be classified as so-called "protein paints" or "paint molecules" that can coat with a high resolution (e.g., <5, <4, or <3 amino acids). In another embodiments, following painting, the interacting protein(s) is/are dissociated, to reveal and expose the non-painted interaction domains that were inaccessible to the paint molecules when the protein(s) was/were interacting in its/their native state. In some embodiments, painted regions are masked from proteinase cleavage or antibody recognition, even after dissociation. The dissociated painted proteins can then be subjected to proteinase cleavage (e.g. trypsin) and e.g. mass spectrometry (MS) sequencing, or e.g. antibody probing. In other embodiments, because the compound (or so called "paint") blocks the proteinase cleavage sites that are not in contact, proteinase fragments for MS sequencing will only be generated from the so-called "non-painted" areas exclusively comprising the interaction domain(s).

In one embodiment, the compound has Formula (I):

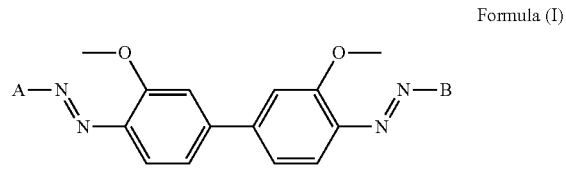

Formula (I)

wherein A and B each independently have Formula (a),

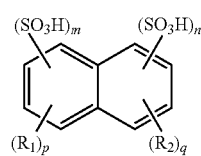

Formula (a)

wherein $R_1$ and $R_2$ each independently is —OH or —$NH_2$; m, n, p and q each independently is 0, 1, 2, 3, or 4 and the sum of m+n is not zero.

In some embodiments, the point of attachment of A and B each independently to the azo group in Formula (I) is at C1, C2, C3, C4, C5, C6, C7, or C8 of the carbon ring of Formula (a).

In another embodiment, the sum of p+q is not zero.
In some embodiments, the sum of p+q is 1 or 2.
In another embodiment, $R_1$ or $R_2$ is —$NH_2$.
In some embodiments, $R_1$ or $R_2$ is —OH.
In other embodiments, $R_1$ or $R_2$ is —$NH_2$ and the sum of p+q is 1 or 2.
In one embodiment, the point of attachment of A and B each independently to the azo group in Formula (I) is para, ortho, or meta to $R_1$ or $R_2$.

In another embodiment, $R_1$ or $R_2$ is —$NH_2$, the sum of p+q is 1 or 2, and the point of attachment of A and B each independently to the azo group in Formula (I) is para or ortho to $R_1$ or $R_2$.

In some embodiments, $R_1$ or $R_2$ is —$NH_2$, the sum of p+q is 1 or 2, and the point of attachment of A and B each independently to the azo group in Formula (I) is meta to $R_1$ or $R_2$.

In one embodiment, the compound has Formula (II), (III), or (IV).

In other embodiments, the interaction site comprises an intrachain interaction site. Thus, in some embodiments, the interaction site can be a site of interaction between a first domain and a second domain of the protein polypeptide chain in a folded state i.e., in a native or undenatured state of the protein e.g., as it is present under physiological conditions, with secondary, tertiary and/or quaternary structures intact.

In another embodiment, the interaction site comprises a site of interaction between the protein and a binding partner, wherein the protein is in a folded state of the protein i.e., in a native or undenatured form of the protein e.g., as it is present under physiological conditions, with secondary, tertiary and/or quaternary structures intact and/or capable of interacting with the binding partner.

In some embodiments, the binding partner comprises a protein, a non-protein molecule, or a molecule comprising a protein or proteinaceous component. In other embodiments, the non-protein molecule is a small molecule.

In one embodiment, the compounds of the present invention non-covalently coat the solvent-accessible surface of the protein but not the inaccessible region of the protein that is not accessible by the compound as a result of intrachain, interchain and/or binding partner interactions. The compounds can remain bound to the protein during denaturation and inhibit digestion via a protease (e.g., trypsin), allowing interaction fragments to be detected e.g., via mass spectrometry. Surface regions not involved in an interaction remain compound covered and undigested, and are thus undetectable e.g., by mass spectrometry. Thus, for example, in some embodiments, wherein the interaction site(s) correspond to sites of interaction between a protein and a binding partner, comparison between a covered or "painted" protein alone and a covered or "painted" protein in complex with the binding partner allows for identification of protein fragments that are only present in the complexed protein/binding partner sample; these fragments are the "hotspots" from the analysis. In other embodiments, for example wherein the interaction site comprises an intrachain interaction site of a single protein polypeptide chain (e.g., an interaction site between two domains of a single folded protein), comparison between a covered or "painted" protein exposed to an agent or stimulus that effects proper folding and a covered or "painted" protein without exposure to the agent or the stimulus allows for identification of protein fragments that are only present in the unexposed protein sample; these fragments are the "hotspots" from the analysis.

In one embodiment, the compound of the present invention is applied in solution to the solution phase native protein when it is folded and/or bound to its binding partner. In other embodiments, the compound will bind to proteins with very high affinity with a low dissociation constant (e.g., $K_D < 10^{-7}$) and a very slow off rate. This can ensure that the protein painting is stable and can remain adherent following partial or complete unfolding of the protein polypeptide chain. In some embodiments, the compound will remain adherent to the protein molecule after exposure to levels of denaturant or detergent treatments that can unfold the protein or dissociate protein-binding partner(s). In other embodiments, once the compound molecules are bound to the protein in solution, and the unbound compound molecules are washed away, the bound compound molecules prevent protease (e.g., trypsin) cleavage at a location at or near the compound binding site.

In some embodiments, the compound of the invention can bind and mask the protein with a resolution. In one embodiment, the resolution comprises sufficient resolution to effectively mask surface domains even over complex 3-D shape curvatures. In another embodiment, the resolution comprises sufficient resolution to achieve a masking density to cover one or more protease cleavage site.

In one embodiment, the resolution comprises sufficient resolution to achieve a masking density to cover at least about 10% of the protease cleavage sites, illustratively, at least about: 10%, 20%, 30%, 40%, 50%, 60%, 70%, 80%, 90%, or 100% of the protease cleavage sites.

In other embodiments, the protease cleavage site is cleavable by a protease, wherein the protease is trypsin, Arg-C proteinase, Asp-N endopeptidase, Caspase1, Caspase2, Caspase3, Caspase4, Caspase5, Caspase6, Caspase7, Caspase8, Caspase9, Caspase10, Chymotrypsin, Clostripain (Clostridiopeptidase B), Enterokinase, Factor Xa, Glutamyl endopeptidase, GranzymeB, LysC, LysN, Pepsin, Proline-endopeptidase, Proteinase K, Staphylococcal peptidase I, Tobacco etch virus protease, Thermolysin, or Thrombin. In one embodiment, the protease is trypsin.

In one embodiment, the compounds of the present invention can bind to the protein with a resolution of about 3 amino acids.

In another embodiment, the compounds of the present invention can bind to the protein with a resolution covering less than 5 contiguous amino acids.

In other embodiments, the compounds having Formula (I) or as prepared by the azo coupling reactions provided herein are masking pigments. In other embodiments, in addition to the compounds having Formula (I) or as prepared by the azo coupling reactions provided herein, one or more additional masking pigments as described herein (e.g., the one or more compounds described herein that include one or more of the aryl hydrocarbon containing organic compounds less than 30 Angstroms in total length as well as the compounds listed in Tables 1 and 2) can be applied in solution to the solution phase native protein e.g., when it is bound to its binding partner or e.g., when folded with/without exposure to an agent or stimulus that effects its folding.

In some embodiments, the compounds described herein including the one or more additional masking pigments can bind to regions of the protein surface using different mechanisms. Some can prefer hydrophobic sites while others can prefer hydrophilic or anionic or cationic regions. In other embodiments, the binding affinity and protein binding region specificity can be a function of the side chain composition of the ring substitutions and the primary structure of the molecule. In one embodiment, one class of pigment mask molecule can bind to the protein molecule at multiple, but limited, number of specific sites. In other embodiments, adding additional classes of pigment mask molecule, which recognize different classes of protein domain, can fill in the gaps such that a proper mixture of molecules will attain full coverage of all the exposed regions of the protein or block all the protease cleavage sites or all the ligand binding sites.

Consequently, in some embodiments, two or more masking molecules with a resolution covering less than about 10, preferably less than about 5, more preferably less than about 3, contiguous amino acids are selected for the masking of a protein surface. In one embodiment, the masking molecules are applied in solution to the solution phase native protein when it is bound to its binding partner.

In one embodiment, a set of masking molecules is selected from a reference list or panel. The set or mixture of masking pigments can be optimally chosen prior to use depending on the known primary and secondary structure of the protein candidates to be analyzed.

In a second embodiment, a set of pigments or masks that are known to prefer phosphorylated amino acids, or other post-translationally modified (PTM) amino acids are selected. Proteins and/or peptides or combinations of proteins/peptides with other molecules such as nucleic acids, can be screened for structures that bind phosphorylated or other post translationally modified regions. The presence of phosphorylation sites or other PTM in the binding interaction can be identified.

In a further embodiment, bioinformatic analysis can be used to automatically reconstruct the amino acid sequence of the binding domain based on the following parameters: a. the selected panel of masking pigments, b. the known amino acid structure of the proteins being studied, and c. the difference in ms peptides generated before and after the binding reaction.

In a further embodiment, provided herein is a diagnostic kit for determining whether one or more protein-ligand (ligand includes drug, or non-protein molecule such as a nucleic acid or carbohydrate) binding events has occurred in a mixture of at least 1 protein and 1 ligand.

In a further embodiment of the invention, the proteins or the masking pigments can be pre-treated or co-incubated with substances that will enhance the binding affinity or specificity by reacting with the protein or with the masking pigment.

In a further embodiment the affinity masking pigments can be administered to the folded protein or to the protein-protein or protein-ligand complex in an automated fashion using appropriate fluidics and molecular size exclusion chromatography, or other means, to rapidly separate the free unbound masking molecules from the proteins with the bound pigments. The quantity of bound or free masking pigments can be monitored by taking advantage of the light absorbance or transmission spectrum of the particular masking molecule.

In some embodiments, the interaction zone exposed following masking (painting) and protein unfolding or dissociation is digested with proteolytic enzymes and sequenced by MS. The masking molecules remain on the proteins after they are unfolded and/or dissociated and unfolded. Proteolytic enzymes such as trypsin will not cleave the regions of the protein that are masked or "painted". The proteolytic enzymes will only cleave the protein domains that participated in the interaction zone and are not blocked by the masking molecules. Following proteolysis, therefore, proteolytic peptides will only be generated from the interacting zone. The cleaved peptides are sequenced by mass spectrometry. The derived mass spectrometry sequence will comprise only the region of interaction, since the peptides will be cleaved only from the regions of the protein(s) that are touching each other and therefore protected from exposure or interaction with the affinity masking molecules.

In another embodiment, the mask can be applied (a) individually to each of two native proteins and then after they interact or (b) individually to a native protein and then after it interacts with its non-protein binding partner. The difference between the sequences revealed before and after the protein(s) bind(s) will reveal the interaction or binding site.

In other embodiments, the method of the present invention can be applied to one binary set of interacting proteins or it can be applied to a large population of native proteins containing a subset of interacting proteins. If applied to a cell protein lysate the output will be the amino acid sequences from only the subset of protein domains that were participating in the protein-protein interactions at the time the masking molecules are introduced. If the method is applied to a single folded native protein, or a protein during various stages of folding, the output can be the regions of the protein masked during the folding process. If the method was used over time following cell stimulation with a ligand, or treatment with an inhibitor, all sets of protein interaction zones that change following this perturbation could be directly and specifically sequenced.

In one embodiment, after a masking or painting step described herein, followed by dissociation of the binding partners, a ligand (e.g., antibody, a protein, or a non-protein molecule) will only recognize the exposed unpainted domain if it has been previously occupied by a binding partner. Thus, the ligand will only detect interaction events. Consider an antibody, drug, peptide, aptamer, or other ligand that is specific for the interaction domain interface of two proteins. In some embodiments, this ligand can be applied to a cell lysate (or a living cell) after the native interacting proteins have been masked (painted) and then dissociated. A positive binding event will only occur if the lysate contains protein interaction events. If the masked and dissociated interacting protein is used as an antigen or immunogen or vaccine only the interaction binding domain will generate an antibody. The result will be the automatic generation of an antibody specific for the interaction domain.

In other embodiments, the present invention provides a method for determining a contact region or binding domain within a folded protein or between the protein and a molecule, the method comprising analyzing a region of an unfolded protein polypeptide chain of a complex comprising a compound complexed or bound to the unfolded protein polypeptide chain, wherein the region does not contain the compound complexed or bound to the unfolded protein polypeptide chain, wherein the unfolded protein polypeptide chain is an unfolded chain of the folded protein, and wherein the region of the unfolded polypeptide chain that does not contain the complexed or bound organic compound corresponds to the contact region or binding domain within the folded protein or between the protein and the molecule, and wherein the compound has Formula (I) or is prepared by the azo coupling reaction disclosed herein.

In another embodiment, the present invention provides a method for determining the contact region within a single folded protein or between a protein complexed with another molecule, comprising introducing a mixture of small organic masking molecules to said protein, wherein said small organic masking molecules bind with high affinity to all exposed sites on said protein or protein complex, thereby coating said protein, wherein the mixture comprises a compound having Formula (I) or prepared by the azo coupling reaction disclosed herein; dissociating said protein or protein complex, such that the small organic masking molecules coat all areas of the protein or protein complex excluding the contact region; and sequencing the contact region.

In other embodiments, the present invention provides a method for mapping the protein-protein contact or binding domains within a single folded protein or between two or more different proteins, the method comprising forming complexes with a compound on the exposed surface of a native protein in solution, b) unfolding the protein to reveal the regions of the polypeptide chain that do not contain the complex(s), and c) analyzing the regions of the polypeptide chain that do not contain the complexes between the compound and the polypeptide chain, wherein the compound has Formula (I) or is prepared by the azo coupling method disclosed herein.

The instant technology finds use in a variety of applications. Drugs that block protein-protein interactions are the next frontier for pharmaceutical companies. In various embodiments, the present invention provides a novel product and methods and articles of manufacture for using same, for a) de novo discovering the protein binding domain targets for this new class of drugs, and b) finding and assaying drugs that block protein interactions. Examples of applications include but are not limited to elucidation of protein-protein interaction, elucidation of drug interaction, elucidation of protein folding, detection of protein-nucleic acid interactions, identification of protein misfolding sequences and the subsequent exposed binding sites, detection of heterochromatin and euchromatin in nucleic acids, miRNA binding, inhibition of protein-protein or protein-nucleic acid interactions, and production of antibodies to specific protein-ligand regions.

In other embodiments, the instant technology disclosed herein can be used to characterize the step-wise folding of an individual protein at the amino acid level, or to map the sequence of binding events over time. It can also be used to discover or evaluate drugs that block protein-protein interactions. The methodology and compositions can be used to map antibody-antigen binding domains for antibody-based therapy, vaccine development, and infectious disease research. The disclosure can be used to directly generate or screen ligands (including drugs or nucleic acids) or antibodies that are specific for the interaction face region of a protein. The technology can be applied to study, characterize, or mark in vitro, or in vivo native protein interaction domains.

The instant technology finds use in a variety of applications and several products may derive. In one embodiment, provided is a diagnostic kit for determining whether one or more protein-ligand (ligand includes drug, or non-protein molecule such as a nucleic acid or carbohydrate) binding events has occurred in a mixture of at least 1 protein and 1 ligand. This diagnostic kit could be used in personalized medicine approaches for determining, in vitro prior to treatment, if the desired protein-drug interaction will occur in a given patient's sample.

In another embodiment, the present disclosure contemplates enhancing protein-ligand interaction specificity for in vitro assays and coupling reactions. The proteins or the masking dyes can be pre-treated or co-incubated with substances that will enhance the binding affinity or specificity by reacting with the protein or with the masking pigment.

Bioinformatic analysis can replace X-ray crystallography for determining protein structure. Bioinformatic analysis can automatically reconstruct the amino acid sequence of the binding domain based on the following parameters: a. the selected panel of masking pigments, b. the known amino acid structure of the proteins being studied, and c. the difference in mass spectrometry identified peptides generated before and after the binding reaction.

The instant disclosure contemplates producing novel antibodies with a specific affinity to the binding interaction. If the masked and dissociated interacting protein is used as an antigen, immunogen, or vaccine, only the interaction binding domain will generate an antibody. The result will be the automatic generation of an antibody specific for the interaction domain.

In other aspects, the present invention provides a method for determining an inhibitor for an interaction site of a protein. The method comprises contacting the protein with a composition comprising a compound to form a complex with the compound at an accessible region of the protein that is accessible by the compound; and determining an amino acid sequence of an inaccessible region of the protein that is not accessible by the compound, thereby determining the inhibitor. The compound has Formula (I) or is prepared by the azo coupling method disclosed herein.

In some embodiments, the method further comprises screening for the inhibitor based on the amino acid sequence of the inaccessible region.

In one embodiment, the inhibitor is a peptide inhibitor.

In another embodiment, the peptide inhibitor comprises the amino acid sequence, or a variant sequence thereof, of the inaccessible region.

In other embodiments, the inhibitor is a large or small molecule inhibitor.

In one embodiment, the large molecule inhibitor is an antibody or a binding fragment thereof.

In other aspects, the present invention provides a peptide that can be of utility in a variety of applications and fields including, but not limited to, diagnostics, therapeutics, and/or medical research for example. In some embodiments, the peptide is screened for and/or determined by the methods disclosed herein.

In one embodiment, the present invention provides a peptide comprising the amino acid sequence set forth as: YRCMISYGGADYKRITV (SEQ ID NO:1) or variant thereof; CYRAMISYGGADYKRITC (SEQ ID NO:2) or variant thereof; LKYDAPAFTVT (SEQ ID NO: 3) or variant thereof; CLKYDAPAFTVTC (SEQ ID NO:4) or variant thereof; LNWYRMSPSNQTDKLAA (SEQ ID NO:5) or variant thereof; LNWYRMSPSNQTDKLAA (SEQ ID NO:6) or variant thereof; CLNWYRMSPSNQTDKLAAC (SEQ ID NO:7) or variant thereof; AISLAPKAQIK (SEQ ID NO:8) or variant thereof; or CAISLAPKAQIKC (SEQ ID NO: 9) or variant thereof.

In another embodiment, the present invention provides a peptide comprising the amino acid sequence, or variant thereof, set forth as: KVTLV (SEQ ID NO:10) or variant thereof; RDDISEIQSLASDHSGR (SEQ ID NO:11) or variant thereof; KEGLEEGDQILRV (SEQ ID NO: 12) or variant thereof; KFPAYER (SEQ ID NO:13) or variant thereof; or KHALLDVTPNAVDR (SEQ ID NO:14) or variant thereof.

Absent an express indication of the N-terminus and/or C-terminus of a peptide set forth herein, the peptide is to be read in the N-terminus to C-terminus orientation. In some embodiments, individual residues are indicated by the identity of the amino acid using a standard one- and/or three-letter code known to one of ordinary skill in the art.

In other embodiments, cyclized peptides are provided that may be more stable in solution. Various methods for cyclizing peptides, e.g., via disulfide bond formation, are known in the art.

In some embodiments, the peptides provided herein can include variants e.g., a peptide variant having one or more (e.g., one, two, three, four, five or more) substitutions, insertions, deletions, and/or additions (and combinations thereof) relative to an amino acid sequence disclosed herein.

Amino acid substitutions can be conservative or non-conservative amino acid substitutions. Conservative amino acid substitutions can be, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitutions also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Non-conservative amino acid substitutions typically entail exchanging a member of one of the classes described above for a member of another class.

In some embodiment, a C-terminal amide, or other C-terminal capping moiety can be present in peptides described herein. In one embodiment, a peptide described herein is amidated at the C-terminal.

In other embodiments, charged linkers may be used. Such charges linkers may contain a significant number of acidic residues (e.g., Asp, Glu, and the like), or may contain a significant number of basic residues (e.g., Lys, Arg, and the like), such that the linker has a pI (isoelectric point) lower than 7 or greater than 7, respectively. As understood by one of ordinary skill in the art, and all other things being equal, the greater the relative amount of acidic or basic residues in a given linker, the lower or higher, respectively, the pI of that linker will be. Such linkers may impart advantageous properties to the peptides disclosed herein, such as modifying the peptides pI, which can in turn improve solubility and/or stability characteristics of such peptides at a particular pH, such as at physiological pH (e.g., between pH 7.2 and pH 7.6, inclusive), or in a pharmaceutical composition including such peptides. As is known to one of ordinary skill in the art, solubility for a peptide may be improved by formulation in a composition having a pH that is at least or more than plus or minus one pH unit from the pI of the peptide.

Amino acid-based linkers can be L form, D form, combinations of L and D forms, β-form, PEG backbone, and the like.

In some embodiments, the peptide has the amino acid sequence set forth in SEQ ID NO:1, 2, 3, 4, 5, 6, 7, 8, 9, 10, 11, 12, 13, or 14, provided that the peptide is not intact PD-1 (also known as CD279), PD-L1 (also known as B7-H1; or CD274), yes-associated protein 2 (YAP2), or zonula occludens-1 (ZO-1) (also known as Tight junction protein-1) polypeptide.

In other embodiments, the peptides provided herein have a length of about 5 amino acids to about 50 amino acids. For example, in some embodiments, a peptide has a length of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. In other embodiments, a peptide can have a length of, without limitation, about 5 to about 15 amino acids, about 15 to about 20 amino acids, about 20 to about 25 amino acids, about 25 to about 30 amino acids, about 30 to about 35 amino acids, about 35 to about 40 amino acids, about 40 to about 45 amino acids, about 45 to about 50 amino acids, about 10 to about 20 amino acids, about 20 to about 30 amino acids, about 30 to about 40 amino acids, or about 40 to about 50 amino acids.

In one embodiment, the peptide has the amino acid sequence YRCMISYGGADYKRITV (SEQ ID NO:1) or the amino acid sequence set forth in SEQ ID NO:1 with one substitution, wherein the peptide has a length of 17 amino acids.

In another embodiment, the peptide has the amino acid sequence CYRAMISYGGADYKRITC (SEQ ID NO:2) or the amino acid sequence set forth in SEQ ID NO: 2 with one substitution, wherein the peptide has a length of 18 amino acids.

In some embodiments, the peptide has the amino acid sequence LKYDAPAFTVT (SEQ ID NO: 3) or the amino acid sequence set forth in SEQ ID NO:3 with one substitution, wherein the peptide has a length of 11 amino acids.

In other embodiments, the peptide has the amino acid sequence CLKYDAPAFTVTC (SEQ ID NO: 4) or the amino acid sequence set forth in SEQ ID NO:4 with one substitution, wherein the peptide has a length of 13 amino acids.

In one embodiment, the peptide has the amino acid sequence LNWYRMSPSNQTDKLAA (SEQ ID NO:5) or the amino acid sequence set forth in SEQ ID NO:5 with one substitution, wherein the peptide has a length of 17 amino acids.

In another embodiment, the peptide has the amino acid sequence LNWYRMSPSNQTDKLAA (SEQ ID NO:6) or the amino acid sequence set forth in SEQ ID NO: 6 with one substitution, wherein the peptide has a length of 17 amino acids.

In some embodiments, the peptide has the amino acid sequence CLNWYRMSPSNQTDKLAAC (SEQ ID NO:7) or the amino acid sequence set forth in SEQ ID NO: 7 with one substitution, wherein the peptide has a length of 19 amino acids.

In other embodiments, the peptide has the amino acid sequence AISLAPKAQIK (SEQ ID NO: 8) or the amino acid sequence set forth in SEQ ID NO:8 with one substitution, wherein the peptide has a length of 11 amino acids.

In one embodiment, the peptide has the amino acid sequence CAISLAPKAQIKC (SEQ ID NO: 9) or the amino acid sequence set forth in SEQ ID NO:9 with one substitution, wherein the peptide has a length of 13 amino acids.

In another embodiment, the peptide has the amino acid sequence KVTLV (SEQ ID NO:10) or the amino acid sequence set forth in SEQ ID NO:10 with one substitution, wherein the peptide has a length of 5 amino acids.

In some embodiments, the peptide has the amino acid sequence RDDISEIQSLASDHSGR (SEQ ID NO:11) or the amino acid sequence set forth in SEQ ID NO:11 with one substitution, wherein the peptide has a length of 17 amino acids.

In other embodiments, the peptide has the amino acid sequence KEGLEEGDQILRV (SEQ ID NO: 12) or the amino acid sequence set forth in SEQ ID NO:12 with one substitution, wherein the peptide has a length of 13 amino acids.

In one embodiment, the peptide has the amino acid sequence KFPAYER (SEQ ID NO:13) or the amino acid sequence set forth in SEQ ID NO:13 with one substitution, wherein the peptide has a length of 7 amino acids.

In another embodiment, the peptide has the amino acid sequence KHALLDVTPNAVDR (SEQ ID NO:14) or the amino acid sequence set forth in SEQ ID NO:14 with one substitution, wherein the peptide has a length of 14 amino acids.

In some embodiments, a C-terminal amide, or other C-terminal capping moiety can be present in peptides described herein. In one embodiment, a peptide as provided herein has a C-terminus that is amidated.

The term "amino acid" as used herein refers to natural amino acids, unnatural amino acids, and amino acid analogs, all in their various stereoisomers (e.g., D and L stereoisomers or other allostereomers if their structures so allow). Natural (or "naturally-occurring") amino acids include the 20 "standard" amino acids that are encoded by the codons of the universal genetic code (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), as well as other "non-standard" amino acids that occur naturally but are not encoded by the codons of the universal genetic code (e.g., hydroxyproline, selenomethionine, and norleucine). Amino acids that are non-standard and/or non-naturally occurring include, without limitation, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

An "analog" is a chemical compound that is structurally similar to another but differs slightly in composition (as in the replacement of one atom by an atom of a different element or in the presence of a particular functional group). An "amino acid analog" therefore is structurally similar to a naturally occurring amino acid molecule as is typically found in native peptides but differs in composition such that either the C-terminal carboxy group, the N-terminal amino group, or the side-chain functional group has been chemically modified or replaced with another functional group. Amino acid analogs include natural and unnatural amino acids that are chemically blocked, reversibly or irreversibly, or modified on their N-terminal amino group or their side-chain groups, and include, for example, methionine sulfoxide, methionine sulfone, S-(carboxymethyl)-cysteine, S-(carboxymethyl)-cysteine sulfoxide and S-(carboxymethyl)-cysteine sulfone. Amino acid analogs may be naturally occurring or can be synthetically prepared. Non-limiting examples of amino acid analogs include 5-Hydroxytrpophan (5-HTP), aspartic acid-(beta-methyl ester), an analog of aspartic acid; N-ethylglycine, an analog of glycine; and alanine carboxamide, an analog of alanine. Other examples of amino acids and amino acids analogs are listed in Gross and Meienhofer, The Peptides: Analysis, Synthesis, Biology, Academic Press, Inc., New York (1983).

The stereochemistry of a peptide can be described in terms of the topochemical arrangement of the side chains of the amino acid residues about the peptide backbone, which is defined by the peptide bonds between the amino acid residues and the l-carbon atoms of the bonded residues. In addition, peptide backbones have distinct termini and thus direction. The majority of naturally occurring amino acids are L-amino acids (including the 20 standard amino acids as well as a number of other naturally-occurring, non-standard amino acids), and naturally occurring, ribosomally-produced peptides are largely comprised of L-amino acids. D-amino acids are the enantiomers of L-amino acids. Assembling peptides out of D-amino acids, which are not recognized by proteases, can enable evasion from digestion and remain intact until reaching membranes (Wade et al., Proc Natl Acad Sci USA 87 (12): 4761-4765, 1990).

The peptides provided herein can be made up of L-amino acids, D-amino acids, or a combination thereof. For example, in some embodiments, a peptide can have an amino acid composition in which at least about 10% (e.g., at least about 10%, at least about 20%, at least about 25%, at least about 30%, at least about 40%, at least about 50%, at least about 60%, at least about 70%, at least about 75%, at least about 80%, at least about 85%, at least about 90%, at least about 95%) of the amino acids are D-amino acids. It is to be noted that some amino acid residues have more than one stereocenter, and the peptides provided herein can, in some embodiments, include diastereomers of these amino acids that differ from each other only in the configuration of one of their stereocenters.

In one embodiment, the peptide comprises one or more D-amino acid residues. In some embodiments, at least about 25 percent, illustratively, about 25 to 100 percent, about 50 to about 55 percent, and about 60 to about 75 percent of the amino acids in the peptide can be D-amino acids. In one embodiment, at least about 25 percent of the amino acids in the peptide can be D-amino acids. In another embodiment, 50 percent of the amino acids in the peptide can be D-amino acids. In one embodiment, at least about 75 percent of the amino acids in the peptide can be D-amino acids. In another embodiment, 100 percent of the amino acids in the peptide can be D-amino acids.

In some embodiments, peptidomimetic compounds can be used in place of the peptides provided herein. As used herein, the term "peptidomimetic" refers to compounds that are synthetic, non-peptide compounds having a three-dimensional conformation (a "peptide motif") that is substantially the same as the three-dimensional conformation of a selected peptide; a peptidomimetic compound therefore can essentially reproduce elements of amino acid structural properties and can confer the same or similar function as the selected peptide. As compared to a selected peptide, a peptidomimetic compound includes non-naturally occurring modifications, such as an altered backbone and/or non-natural amino acids. In some embodiments, for example, peptidomimetics can include beta-amino acids, peptoids, and/or N-methyl amino acids.

Peptidomimetic compounds can include amide ("peptide") or non-amide ("non-peptide") bonds in their backbone structure or can include a combination of peptide and non-peptide bonds in their backbone structure. Peptidomimetic compounds that are protease resistant or that have additional characteristics that enhance therapeutic utility, such as increased cell permeability and prolonged biological half-life, can be particularly useful. Such compounds typically have a backbone that is partially or completely non-peptide, but with side groups that are identical or similar to the side groups of the amino acid residues that occur in the peptide upon which the peptidomimetic compound is based. Several types of chemical bonds (e.g., ester, thioester, thioamide, retroamide, sulfonamide, reduced carbonyl, dimethylene and ketomethylene) can be useful substitutes for peptide bonds in the construction of peptidomimetic compounds. In some embodiments, the compounds provided herein include hybrids that contain one or more peptide portions and one or more peptidomimetic portions. Such hybrid peptides can incorporate a combination of natural amino acids and mimetic amino acids (e.g., standard amino acids and peptoids) in the same molecule.

The peptides provided herein can be obtained by any of a number of methods, including those known in the art. In some embodiments, a peptide can be obtained by extraction from a natural source (e.g., from isolated cells, tissues or bodily fluids), or can be produced by expression of a recombinant nucleic acid encoding the peptide, or by chemical synthesis (e.g., using solid phase peptide synthesis methods or a peptide synthesizer such as an ABI Peptide Synthesizer; Applied Biosystems; Foster City, CA). For example, standard recombinant technology using an expression vector encoding a peptide provided herein can be used. The resulting peptide then can be purified using, for example, affinity chromatographic techniques and HPLC. The extent of purification can be measured by any appropriate method, including but not limited to: column chromatography, polyacrylamide gel electrophoresis, or high-performance liquid chromatography. In some embodiments, a peptide can be designed or engineered to contain a tag sequence that allows the peptide to be purified (e.g., captured onto an affinity matrix). For example, a tag such as c-myc, hemagglutinin, polyhistidine, or FLAG™ tag (Kodak) can be used to aid peptide purification. Such tags can be inserted anywhere within the peptide, including at either the carboxyl or amino terminus. Other fusions that can be used include enzymes that aid in the detection of the peptide, such as alkaline phosphatase. In some embodiments, a peptide can be amidated at its carboxy terminus.

In some embodiments, a peptide provided herein can be isolated or purified. A "purified peptide" is a peptide that either has no naturally occurring counterpart (e.g., a peptidomimetic), or has been chemically synthesized and is thus uncontaminated by other peptides, or has been recombinantly produced and has been separated from components of the cell in which it was produced, or that has been separated or purified from other cellular components by which it is naturally accompanied (e.g., other cellular proteins, polynucleotides, or cellular components). Typically, a peptide is considered "purified" when it is at least 70%, by dry weight, free from the proteins and other molecules with which it naturally associates. A preparation of a purified peptide therefore can be, for example, at least about 80%, at least about 90%, or at least about 99%, by dry weight, the peptide. Suitable methods for purifying peptides can include, for example, affinity chromatography, immunoprecipitation, size exclusion chromatography, and ion exchange chromatography. The extent of purification can be measured by any appropriate method, including but not limited to: column chromatography, polyacrylamide gel electrophoresis, or high-performance liquid chromatography.

In one aspect, the present invention provides a polynucleotide encoding a peptide provided herein, or a nucleic acid molecule (e.g., expression vector, plasmid, etc.) comprising the polynucleotide encoding the peptide.

Subjects that can be administered or otherwise benefit from the peptides, compositions, methods, articles, and kits provided herein include vertebrates such as, without limitation, mammals. A mammal can be a human or animal including livestock and companion animals. Companion animals include but are not limited to animals kept as pets. In some embodiments, the subject is a human. In another embodiment, the subject is a non-human mammal.

In another aspect, the present invention provides a composition comprising a peptide, or a polynucleotide encoding the peptide, provided herein. In some embodiments, the peptides provided herein may be formulated with pharmaceutically acceptable carriers or diluents as well as any other known adjuvants and excipients in accordance with conventional techniques such as those disclosed in e.g., Remington: The Science and Practice of Pharmacy, 19th Ed. (Easton, Pa.: Mack Publishing Company, 1995); Remington's Pharmaceutical Sciences, 18th Ed. (1990, Mack Publishing Co., Easton, PA 18042); Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

For example, peptides as provided herein can be formulated in compositions by admixture with one or more pharmaceutically acceptable, non-toxic excipients or carriers. In some embodiments, a composition can include one particular peptide, while in other embodiments a composition can include two or more different peptides (e.g., peptides having different sequences or different amounts of D- and L-amino acids).

In some embodiments, the compositions provided herein can contain one or more peptides at a concentration of about 0.001 µg/ml to about 100 µg/ml (e.g., about 0.001 µg/ml to about 0.01 µg/ml, about 0.005 µg/ml to about 0.05 µg/ml, about 0.01 µg/ml to about 1 µg/ml, about 0.01 µg/ml to about 10 µg/ml, about 0.05 µg/ml to about 5 µg/ml, about 0.05 µg/ml to about 25 µg/ml, about 0.1 µg/ml to about 10 µg/ml, about 0.5 µg/ml to about 50 µg/ml, about 1 µg/ml to about 100 µg/ml, or about 10 µg/ml to about 100 µg/ml.

In other embodiments, the composition further comprises an excipient. Excipients (also referred to as pharmaceutically acceptable carriers) can be liquid or solid and can be selected with the planned manner of administration in mind so as to provide for the desired bulk, consistency, and other pertinent transport and chemical properties, when combined with one or more of peptides and any other components of a given composition. Common excipients include, without limitation, sterile water, saline, polyalkylene glycols such as polyethylene glycol, oils of vegetable origin, hydrogenated naphthalenes, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). In some embodiments, biocompatible, biodegradable lactide polymer, lactide/glycolide copolymer, polyoxyethylene-polyoxypropylene copolymers, or combinations thereof can be used as excipients for controlling the release of a peptide in vivo.

In other embodiments, a composition can include a peptide and one or more molecular crowding agents such as, by way of example and not limitation, FICOLL™ (e.g., FICOLL™ 70), polyethylene glycol (PEG), and dextran. FICOLL™ is a neutral, highly branched, high-mass, hydrophilic polysaccharide that dissolves readily in aqueous solutions. PEG is a polymer of ethylene oxide and is commercially available over a wide range of molecular weights from 300 g/mol to 10,000,000 g/mol. Dextran is a complex, branched polysaccharide made of glucose molecules. Without being bound by a particular mechanism, such agents may help to mimic the natural cellular environment, which may enhance the activity of the peptide. Such agents can be included in the compositions in amounts from about 5% to about 50% wt/vol (e.g., about 5%, about 10%, about 15%, about 20%, about 25%, about 30%, about 35%, about 40%, about 45%, or about 50% wt/vol, or any range there between, including about 5% to about 10%, about 10% to about 20%, about 20% to about 25%, about 25% to about 30%, about 30% to about 40%, or about 40% to about 50%).

In some embodiments, pharmaceutical formulations contemplated for use in the methods of the invention may include about 0.01 to 1.0% (w/v), in certain embodiments about 0.05 to about 1.0%, of the peptide, about 0.02 to about 0.5% (w/v) of an acetate, phosphate, citrate or glutamate buffer allowing a pH of the final composition of from about 3.0 to about 7.0; about 1.0 to 10% (w/v) of a carbohydrate or polyhydric alcohol tonicifier and, optionally, about 0.005 to 1.0% (w/v) of a preservative selected from the group of m-cresol, benzyl alcohol, methyl, ethyl, propyl and butyl parabens and phenol. In another embodiment, such a preservative may be included if the formulated peptide is to be included in a multiple use product.

In still further embodiments, a pharmaceutical formulation of the present peptides may contain a range of concentrations of the peptide(s), e.g., between about 0.01% to about 98% w/w, or between about 1 to about 98% w/w, or preferably between 80% and 90% w/w, or preferably between about 0.01% to about 50% w/w, or more preferably between about 10% to about 25% w/w in these embodiments. A sufficient amount of water for injection may be used to obtain the desired concentration of solution.

In some embodiments, compositions can further include one or more other peptides, wherein each of the one or more other peptides has one or more biological activities (e.g., anticancer activity).

Compositions can be prepared for topical (e.g., transdermal, sublingual, ophthalmic, or intranasal) administration, parenteral administration (e.g., by subcutaneous, intrathecal, intraventricular, intramuscular, or intraperitoneal injection, or by intravenous drip, in the form of liquid solutions or suspensions in aqueous physiological buffer solutions), for oral administration (e.g., in the form of tablets or capsules), or for intranasal administration (e.g., in the form of powders, nasal drops, or aerosols), depending on whether local or systemic treatment is desired and on the area to be treated. Administration can be rapid (e.g., by injection) or can occur over a period of time (e.g., by slow infusion or administration of slow release formulations). Compositions for other routes of administration also can be prepared as desired using appropriate methods. In addition, compositions can be prepared for in vitro use.

Formulations for topical administration of peptides include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Nasal sprays also can be useful, and can be administered by, for example, a nebulizer, an inhaler, or another nasal spray device. Conventional pharmaceutical carriers, aqueous, powder or oily bases, thickeners and the like may be useful.

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Compositions and formulations for parenteral, intrathecal or intraventricular administration can include sterile aqueous solutions, which also can contain buffers, diluents and other suitable additives (e.g., penetration enhancers, carrier compounds and other pharmaceutically acceptable carriers).

In other embodiments, the composition is a pharmaceutical composition.

In some embodiments, pharmaceutical compositions can include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations can be useful for oral delivery of therapeutics due to their ease of formulation and efficacy of solubilization, absorption, and bioavailability.

Liposomes are vesicles that have a membrane formed from a lipophilic material and an aqueous interior that can contain the composition to be delivered. Liposomes can be particularly useful due to their specificity and the duration of action they offer from the standpoint of drug delivery. Liposome compositions can be formed, for example, from phosphatidylcholine, dimyristoyl phosphatidylcholine, dipalmitoyl phosphatidyl-choline, dimyristoyl phosphatidylglycerol, or dioleoyl phosphatidylethanolamine. Numerous lipophilic agents are commercially available, including LIPOFECTIN® (Invitrogen/Life Technologies, Carlsbad, CA) and EFFECTENE™ (Qiagen, Valencia, CA).

The peptides provided herein further encompass pharmaceutically acceptable salts, esters, or salts of such esters, or any other compound which, upon administration to an animal including a human, is capable of providing (directly or indirectly) the biologically active metabolite or residue thereof. Accordingly, for example, provided herein are pharmaceutically acceptable salts of peptides, prodrugs and pharmaceutically acceptable salts of such prodrugs, and other bioequivalents. The term "prodrug" indicates a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the peptides provided herein (i.e., salts that retain the desired biological activity of the parent peptide without imparting undesired toxicological effects). Examples of pharmaceutically acceptable salts include, without limitation, salts formed with cations (e.g., sodium, potassium, calcium, or polyamines such as spermine), acid addition salts formed with inorganic acids (e.g., hydrochloric acid, hydrobromic acid, sulfuric acid, phosphoric acid, or nitric acid), and salts formed with organic acids (e.g., acetic acid, citric acid, oxalic acid, palmitic acid, or fumaric acid).

Compositions additionally can contain other adjunct components such as, for example, lubricants, preservatives, stabilizers, wetting agents, emulsifiers, salts for influencing osmotic pressure, buffers, colorings, flavorings, and aromatic substances. When added, however, such materials should not unduly interfere with the biological activities of the peptide components within the compositions provided herein. The formulations can be sterilized if desired.

Dosing of compositions for administration to a subject typically is dependent on the severity and responsiveness of the condition to be treated, with the course of treatment lasting, in some embodiments, from several days to several months, or in other embodiments until a cure is affected or a diminution of the condition is achieved. Persons of ordinary skill in the art routinely determine optimum dosages, dosing methodologies and repetition rates. Optimum dosages can vary depending on the relative potency of individual peptides and can generally be estimated based on $EC_{50}$ found to be effective in in vitro and in vivo animal models.

In some embodiments, dosage is about 0.01 μg to about 100 g per kg of body weight, and may be given once or more daily, biweekly, weekly, monthly, or even less often. Following successful treatment, it may be desirable to have the patient undergo maintenance therapy to prevent the recurrence of the disease state.

In some embodiments, a preliminary dosage can be inferred using guidelines put forth by the FDA (Guidance for Industry: Estimating the Maximum Safe Starting Dose in Initial Clinical Trials for Therapeutics in Adult Healthy Volunteers F.a.D. Administration, Editor. 2005 (Rockville, MD), which is herein incorporated by reference in its entirety).

In one embodiment, dosage is at least about 0.01 mg per kg of body weight, illustratively, about 0.01 mg to about 100 mg per kg of body weight, about 0.05 mg to about 50 mg per kg of body weight, about 0.1 mg to about 10 mg per kg of body weight, about 0.4 mg to about 5 mg per kg of body weight, and may be given once or more daily, biweekly, weekly, monthly, or even less often.

In some embodiments, dosage is about 0.4 mg to about 5 mg per kg of body weight, and may be given once or more daily, biweekly, weekly, monthly, or even less often.

In other embodiments, a dose of at least about 0.01 μg is given, illustratively, about 0.01 μg to about 1 g, about 0.1 μg to about 0.1 g, about 1 μg to about 24 mg, and may be given once or more daily, biweekly, weekly, monthly, or even less often.

In other embodiments, one or more peptides can be admixed, encapsulated, conjugated or otherwise associated with other molecules, molecular structures, or mixtures of compounds such as, for example, liposomes, polyethylene glycol, receptor targeted molecules, or oral, topical or other formulations, for assisting in uptake, distribution, absorption, or activity.

In some aspects, the present invention provides a method for preventing or disrupting an interaction between PD-1 and PD-L1. The method comprises contacting PD-1 or PD-L1 with a peptide provided herein, or a composition comprising the peptide or a polynucleotide encoding the peptide, before, concomitant with, or after the interaction between PD-1 and PD-L1.

In one embodiment, the contacting occurs in vitro, ex vivo, or in vivo.

PD-1 is expressed on the surface of activated T cells. Its ligand, PD-L1 is expressed on the surface of dendritic cells or macrophages. PD-1 and PD-L1 belong to the family of immune checkpoint proteins that act as co-inhibitory factors, which can halt or limit the development of the T cell response. For example, PD-L1 is commonly overexpressed on tumor cells in the tumor microenvironment. Without wishing to be bound to any particular theory, it is believed that PD-L1 expressed on the tumor cells binds to PD-1 receptors on the activated T cells, which leads to the inhibition of the cytotoxic T cells and that these deactivated T cells remain inhibited in the tumor microenvironment, thereby allowing tumor cells to exert immune resistance.

Thus, one approach in treating (or drug discovery for) a disease, disorder, or condition associated with PD-1/PD-L1 interaction (e.g., cancer or infection) is the development of immune checkpoint inhibitors as therapeutics.

In one embodiment, the present invention provides a method for treating or preventing a disease, disorder, or condition associated with PD-1/PD-L1 interaction in a subject in need thereof. The method comprises administering to the subject a therapeutically or prophylactically effective amount of a peptide provided herein, or a composition comprising the peptide or a polynucleotide encoding the peptide.

In another embodiment, the therapeutically or prophylactically effective amount sufficient to prevent or disrupt an interaction between PD-1 and PD-L1, thereby preventing formation of or disrupting a PD-1/PD-L1 complex.

In some embodiments, the disease, disorder, or condition associated with PD-1/PD-L1 interaction is a viral infection or cancer.

In some embodiments, the peptide comprises the amino acid sequence set forth as: YRCMISYGGADYKRITV (SEQ ID NO:1) or variant thereof; CYRAMISYGGADYKRITC (SEQ ID NO:2) or variant thereof; LKYDAPAFTVT (SEQ ID NO:3) or variant thereof; CLKYDAPAFTVTC (SEQ ID NO:4) or variant thereof; LNWYRMSPSNQTDKLAA (SEQ ID NO: 5) or variant thereof; LNWYRMSPSNQTDKLAA (SEQ ID NO:6) or variant thereof; CLNWYRMSPSNQTDKLAAC (SEQ ID NO:7) or variant thereof; AISLAPKAQIK (SEQ ID NO: 8) or variant thereof; or CAISLAPKAQIKC (SEQ ID NO:9) or variant thereof.

In one embodiment, the peptide has the amino acid sequence YRCMISYGGADYKRITV (SEQ ID NO:1) or the amino acid sequence set forth in SEQ ID NO:1 with one substitution, wherein the peptide has a length of 17 amino acids.

In another embodiment, the peptide has the amino acid sequence CYRAMISYGGADYKRITC (SEQ ID NO:2) or the amino acid sequence set forth in SEQ ID NO: 2 with one substitution, wherein the peptide has a length of 18 amino acids.

In some embodiments, the peptide has the amino acid sequence LKYDAPAFTVT (SEQ ID NO: 3) or the amino acid sequence set forth in SEQ ID NO:3 with one substitution, wherein the peptide has a length of 11 amino acids.

In other embodiments, the peptide has the amino acid sequence CLKYDAPAFTVTC (SEQ ID NO: 4) or the amino acid sequence set forth in SEQ ID NO:4 with one substitution, wherein the peptide has a length of 13 amino acids.

In one embodiment, the peptide has the amino acid sequence LNWYRMSPSNQTDKLAA (SEQ ID NO:5) or the amino acid sequence set forth in SEQ ID NO:5 with one substitution, wherein the peptide has a length of 17 amino acids.

In another embodiment, the peptide has the amino acid sequence LNWYRMSPSNQTDKLAA (SEQ ID NO:6) or the amino acid sequence set forth in SEQ ID NO: 6 with one substitution, wherein the peptide has a length of 17 amino acids.

In some embodiments, the peptide has the amino acid sequence CLNWYRMSPSNQTDKLAAC (SEQ ID NO:7) or the amino acid sequence set forth in SEQ ID NO: 7 with one substitution, wherein the peptide has a length of 19 amino acids.

In other embodiments, the peptide has the amino acid sequence AISLAPKAQIK (SEQ ID NO: 8) or the amino acid sequence set forth in SEQ ID NO:8 with one substitution, wherein the peptide has a length of 11 amino acids.

In one embodiment, the peptide has the amino acid sequence CAISLAPKAQIKC (SEQ ID NO: 9) or the amino acid sequence set forth in SEQ ID NO:9 with one substitution, wherein the peptide has a length of 13 amino acids.

As used herein, the term "treating" does not necessarily imply that a subject is treated until total recovery and includes, for example, the amelioration or management of one or more symptoms of the disease, disorder, or condition associated with PD-1/PD-L1 interaction. "Preventing" the disease, disorder, or condition associated with PD-1/PD-L1 interaction should not be taken to necessarily imply that development of the disease, disorder, or condition associated with PD-1/PD-L1 interaction is completely prevented and includes, without limitation, delay of the development of the disease, disorder, or condition associated with PD-1/PD-L1 interaction.

In one embodiment, the therapeutically effective amount is an amount sufficient to stop or slow the progression of the disease, disorder, or condition associated with PD-1/PD-L1 interaction.

In some embodiments, the method for treating the disease, disorder, or condition associated with PD-1/PD-L1 interaction is used as a co-therapy such as, for example, administration in conjunction with radiation, surgery, or other chemotherapeutics. In other embodiments, the method includes administration of a therapeutically effective amount of the peptide in combination with an additional therapeutic e.g., an anti-cancer agent. A wide variety of anti-cancer (i.e., anti-neoplastic) agents are known in the art and include, for example alkylating agents, antimetabolites, natural antineoplastic agents, hormonal antineoplastic agents, angiogenesis inhibitors, differentiating reagents, RNA inhibitors, antibodies or immunotherapeutic agents, gene therapy agents, small molecule enzymatic inhibitors, biological response modifiers, and anti-metastatic agents.

In still further embodiments, the method for treating the disease, disorder, or condition associated with PD-1/PD-L1 interaction can be used an adjuvant therapy such as, for example, administering after surgery or other treatments (e.g., radiation, hormone therapy, or chemotherapy). Accordingly, in such embodiments, the method of adjuvant therapy encompasses administering following a primary or initial treatment, and either alone or in combination with one or more other adjuvant treatments, including, for example surgery, radiation therapy, or systemic therapy (e.g., chemotherapy, immunotherapy, hormone therapy, or biological response modifiers). In other embodiments, the method relates to neoadjuvant therapy, which is administered prior to a primary treatment.

Some non-limiting examples of cancer include carcinoma, melanoma, lymphoma, blastoma, sarcoma, germ cell tumors, and leukemia or lymphoid malignancies. Non-limiting examples of cancers that fall within these broad categories include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including lung cancer, gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, melanoma, multiple myeloma and B-cell lymphoma, brain, as well as head and neck cancer, and associated metastases.

In other embodiments, cancer also encompasses cell proliferative disorders which are associated with some degree of abnormal cell proliferation and includes tumors, which include neoplasms or neoplastic cell growth and proliferation, whether malignant or benign, and all pre-cancerous and cancerous cells and tissues.

In other aspects, the present invention provides a method for preventing or disrupting an interaction between YAP and ZO. The method comprises contacting YAP or ZO with a peptide provided herein, or a composition comprising the peptide or a polynucleotide encoding the peptide, before, concomitant with, or after the interaction between YAP and ZO.

In one embodiment, the contacting occurs in vitro, ex vivo, or in vivo.

In another embodiment, YAP is YAP2 and ZO is ZO-1.

The Hippo pathway, a signaling network with both pro-apoptotic and anti-apoptotic activities, regulates growth and differentiation of tissues and has been implicated in wound-healing processes. Specifically, Hippo pathway signaling has been shown by others to regulate wound-induced polyploidization, or expansion of non-dividing diploid cells, in *Drosophila*. Mammalian transcriptional factors YAP and TAZ upregulate a host of essential wound healing genes, such that siRNA knockdown of either YAP or TAZ results in a delayed rate of skin wound closure.

One of ordinary skill in the art considers YAP itself a bonafide oncogene upregulated in some cancers and regulated in vivo by a variety of different proteins such as kinase LATS, ZOs, and regulatory 14-3-3, which primarily effect that migration of YAP from the cytoplasm to the nucleus. YAP may have both pro-apoptotic and pro-proliferative effects; YAP interaction with TEAD has been shown to promote expression of growth factors and support proliferation, while YAP interaction with p73 promotes apoptosis. The ZO family of proteins, namely the three isoforms, ZO-1, ZO-2, and ZO-3, are a set of binding partners of YAP which have been shown to form intracellular plaques that join transmembrane proteins with the actin cytoskeleton at tight junctions.

Thus, one approach in treating (or drug discovery for) a disease, disorder, or condition associated with YAP/ZO interaction (e.g., a disease, disorder, or condition relating to or involving e.g., cancer, wound healing, Hippo pathway, etc.) is the development of inhibitors of YAP/ZO interaction as therapeutics.

In one embodiment, the present invention provides a method for treating or preventing a disease, disorder, or condition associated with YAP/ZO interaction in a subject in need thereof. The method comprises administering to the subject a therapeutically or prophylactically effective amount of a peptide provided herein, or a composition comprising the peptide or a polynucleotide encoding the peptide.

In another embodiment, the therapeutically or prophylactically effective amount sufficient to prevent or disrupt an interaction between YAP and ZO, thereby preventing formation of or disrupting a YAP/ZO complex.

In some embodiments, the disease, disorder, or condition associated with YAP/ZO interaction is cancer or wound healing.

In another embodiment, YAP is YAP2 and ZO is ZO-1.

In some embodiments, the peptide comprises the amino acid sequence set forth as: YRCMISYGGADYKRITV (SEQ ID NO:1) or variant thereof; CYRAMISYGGA-DYKRITC (SEQ ID NO:2) or variant thereof; LKYDAPAFTVT (SEQ ID NO:3) or variant thereof; CLKYDAPAFTVTC (SEQ ID NO:4) or variant thereof; LNWYRMSPSNQTDKLAA (SEQ ID NO: 5) or variant thereof; LNWYRMSPSNQTDKLAA (SEQ ID NO:6) or variant thereof; CLNWYRMSPSNQTDKLAAC (SEQ ID NO:7) or variant thereof; AISLAPKAQIK (SEQ ID NO: 8) or variant thereof; or CAISLAPKAQIKC (SEQ ID NO:9) or variant thereof.

In one embodiment, the peptide has the amino acid sequence YRCMISYGGADYKRITV (SEQ ID NO:1) or the amino acid sequence set forth in SEQ ID NO:1 with one substitution, wherein the peptide has a length of 17 amino acids.

In another embodiment, the peptide has the amino acid sequence CYRAMISYGGADYKRITC (SEQ ID NO:2) or the amino acid sequence set forth in SEQ ID NO: 2 with one substitution, wherein the peptide has a length of 18 amino acids.

In some embodiments, the peptide has the amino acid sequence LKYDAPAFTVT (SEQ ID NO: 3) or the amino acid sequence set forth in SEQ ID NO:3 with one substitution, wherein the peptide has a length of 11 amino acids.

In other embodiments, the peptide has the amino acid sequence CLKYDAPAFTVTC (SEQ ID NO: 4) or the amino acid sequence set forth in SEQ ID NO:4 with one substitution, wherein the peptide has a length of 13 amino acids.

In one embodiment, the peptide has the amino acid sequence LNWYRMSPSNQTDKLAA (SEQ ID NO:5) or the amino acid sequence set forth in SEQ ID NO:5 with one substitution, wherein the peptide has a length of 17 amino acids.

In another embodiment, the peptide has the amino acid sequence LNWYRMSPSNQTDKLAA (SEQ ID NO:6) or the amino acid sequence set forth in SEQ ID NO: 6 with one substitution, wherein the peptide has a length of 17 amino acids.

In some embodiments, the peptide has the amino acid sequence CLNWYRMSPSNQTDKLAAC (SEQ ID NO:7) or the amino acid sequence set forth in SEQ ID NO: 7 with one substitution, wherein the peptide has a length of 19 amino acids.

In other embodiments, the peptide has the amino acid sequence AISLAPKAQIK (SEQ ID NO: 8) or the amino acid sequence set forth in SEQ ID NO:8 with one substitution, wherein the peptide has a length of 11 amino acids.

In one embodiment, the peptide has the amino acid sequence CAISLAPKAQIKC (SEQ ID NO: 9) or the amino acid sequence set forth in SEQ ID NO:9 with one substitution, wherein the peptide has a length of 13 amino acids.

As used herein, the term "treating" does not necessarily imply that a subject is treated until total recovery and includes, for example, the amelioration or management of one or more symptoms of the disease, disorder, or condition associated with YAP/ZO interaction. "Preventing" the disease, disorder, or condition associated with YAP/ZO interaction should not be taken to necessarily imply that development of the disease, disorder, or condition associated with YAP/ZO interaction is completely prevented and includes, without limitation, delay of the development of the disease, disorder, or condition associated with YAP/ZO interaction.

In one embodiment, the therapeutically effective amount is an amount sufficient to stop or slow the progression of the disease, disorder, or condition associated with YAP/ZO interaction.

In some embodiments, the method for treating a disease, disorder, or condition associated with YAP/ZO interaction is used as a co-therapy such as, for example, administration in conjunction with radiation, surgery, or other chemotherapeutics. In other embodiments, the method includes administration of a therapeutically effective amount of the peptide in combination with an additional therapeutic e.g., an anti-cancer agent.

In still further embodiments, the method for treating a disease, disorder, or condition associated with YAP/ZO interaction can be used an adjuvant therapy such as, for example, administering after surgery or other treatments (e.g., radiation, hormone therapy, or chemotherapy).

The invention will be further described in the following examples, which do not limit the scope of the invention described in the claims.

EXAMPLES

Example 1

Materials and Methods

Thyroglobulin, catalase, carbonic anhydrase, and lysozyme standards were purchased from Sigma Aldrich, catalog numbers 9010-34-8, C1345, 9001-03-0, and 12650-88-3 respectively. Apoferritin was purchased from Alfa Aesar, catalog number AAJ60630MC. Proteins stocks were prepared in 1×PBS and stored in single use aliquots at −80° C. Hippo pathway proteins were purchased from the following suppliers: YAP1, transcript variant 1 (Origene, catalog number TP325864), LATS1 (Abcam, catalog number ab125612), TJP1 (Origene, catalog number TP322836), and YWHAQ (Origene, catalog number TP308646). Fast Blue B salt and Fast Red TR salt were purchased from Sigma, catalog numbers 14263-94-6 and 368881 respectively. Coupling agents Naphthionic Acid, H-acid, 2-napthol, Peri Acid, 6-Cleve Acid, and Laurent Acid were purchased from TCI Chemicals.

Preparation of Compounds

Dyes stocks were prepared to 1 mg/mL final concentrations. Synthesis was conducted as follows: Fast Dyes were mixed in 1× Dubelcco's PBS with an excess of coupling agent (3-fold molar concentration of coupling agent to fast dye) and vortexed. Reactions were conducted at room temperature and proceeded in the first 5 minutes of mixing with evident color change. Dye stocks were allowed to incubate at room temperature for one week prior to use. Dyes were used without further purification and were diluted prior to use in protein painting. Dye reagents were vortexed before each use, and stable for >6 months at room temperature. Reactions were monitored by reverse phase C18 TLC (mobile phase of 60% methanol, 40% water) to determine number of product bands. For Fast Blue B+Naphthionic Acid, 2 major product bands were observed with Rf=0.32 (Orange) and Rf=0.61 (Pink), while 1 minor product band was observed with Rf=0.51 (Light Orange). The two major product bands were separated via reverse-phase flash column chromatography conducted essentially as described previously using a 20 mm column, stationary phase of COSMOSIL C18-OPN reverse phase resin (Nacalai USA, Catalog number 37842-66), and mobile phase of 60% methanol or 30% acetonitrile. Fractions containing individual bands were identified via reverse-phase TLC and were pooled and dried. Pure samples by TLC were analyzed by NMR to confirm structure of each major product.

Confirmation of coupling positions of naphthionic acid to Fast Blue B for each major product were confirmed via NMR. Samples were isolated via reverse-phase column chromatography as described above, and 5-10 mg of dried sample was resuspended in d6-DMSO for NMR.

Determination of Specific Binding

To determine specific binding of each candidate dye, thyroglobulin was primarily used as a model protein, because its large surface area facilitated more molecules of dye binding per protein, and thus higher signal to noise ratios versus smaller proteins. Candidate dyes were examined on a UV-2501PC UV-Vis spectrometer to determine Amax values. Standard curves were prepared for quantification of molecules of dye; dyes were eliminated from consideration if sensitivity of detection was not greater than 10 µM in solution. Thyroglobulin (1-5 µM) was mixed with 100-fold molar excess of candidate dye dissolved in PBS and allowed to associate between 15 seconds to 2 hours at room temperature. After association, 50 µL of the dye-protein mixtures were passed through a mini Quick Spin Oligo Column (Sephadex G-25 resin, Roche) and centrifugated at 1000×g for 1 min to separate unbound dye from the protein-dye complex. The collected flow-through was examined with UV-Vis spectroscopy, and quantity of dye in the flow-through was calculated using the previously developed standard curve for the dye. Specific Binding was defined as [Paint Molecules Bound]/[Protein]. A plot of specific binding versus time was fit with the Michaelis-Menton equation in GraphPad Prism 6 as a model to determine association kinetics and maximum dye binding, where Vmax represents the maximum amount of dye molecules that bind to the protein at equilibrium. All curves are fit to data from two independent experiments. Specific binding of dye candidates to lysozyme was conducted similarly, with the change that lysozyme (2-10 µM) was mixed with 50-fold molar excess of dye candidate dissolved in PBS and allowed to associate for the indicated time points.

Circular Dichroism Spectroscopy

Circular dichroism spectroscopy was conducted using bovine serum albumin on a Jasco J-1500 CD spectrometer from 190-350 nm using a 1 mm cuvette. BSA stock solutions were prepared to 2 mg/mL from lyophilized protein in sterile-filtered 10 mM phosphate buffer, pH 7.0 and centrifuged at 16,000×g to remove particulates. Concentration was determined via A280 using an extinction coefficient of 43,824 $M^{-1}$ $cm^{-1}$ for BSA. Stocks were stored at −80° C. and diluted to the appropriate concentration in sterile-filtered MilliQ water for each experiment. Final concentration of BSA in each sample was 2 µM (0.12 mg/mL). Samples were incubated for 10 minutes with dye at a molar ratio equal to the specific binding of the molecule to the protein (i.e. 18 µM of FBBNA for 1 µM of BSA). Controls were incubated with equivolume amounts of MilliQ water in place of dye. Samples were subsequently either incubated at room temperature or denatured at 37° C. for 1 hr in the presence of varying concentrations of urea (2M, 4M, or 6M) and 3.5 mM DTT. Each spectrum shown is an average of 3 scans taken using a band width of 1 nm, a scanning speed of 50 nm/min, and an integration time of 8 s. All samples with dye or urea have CD contributions from these buffers alone subtracted from the final spectrum. Helical content of BSA spectra was determined using the online server DICHROWEB (Whitmore, L., and Wallace, B. A., "Protein secondary structure analyses from circular dichroism spectroscopy: methods and reference databases." Biopolymers. 89, 392-400, 2008; Whitmore, L., and Wallace, B. A., "DICHROWEB, an online server for protein secondary structure analyses from circular dichroism spectroscopic data." Nucleic Acids Res. 32, W668-673, 2004) to confirm native structure.

Protein Painting

To prepare protein complexes, ~1 µg of the larger protein in the complex was mixed with an equimolar concentration of its protein binding partner (final molar concentration of proteins ranged from 0.1-2 µM) in 1×PBS and allowed to incubate for 1 hour under rotation at room temperature to facilitate complex formation. After incubation, protein complexes were pulsed with >100-fold molar excess of dye dissolved in PBS and allowed to associate for 5 minutes. After association, samples were passed through a mini Quick Spin Oligo Column (Sephadex G25 resin, Roche) and centrifuged at 1000×g for 1 min at room temperature. The flow through was collected and denatured with urea (final concentration 2M), reduced with 10 mM dithiothreitol and incubated at 37° C. for 15 min, then alkylated with 50 mM iodoacetamide and incubated 15 min in the dark. Samples were digested for 1.5 hours at 37° C. with sequencing-grade trypsin (Promega) at a 1:10 w/w protease/protein ratio. Digestion was stopped with 6 µL of glacial acetic acid. Tryptic peptides were purified using Pierce C18 Spin columns (Thermo Scientific) according to the manufacturer's directions. Desalted peptides were dried under nitrogen and stored at −20° C. until mass spectrometry analysis.

Mass Spectrometry (MS)

LC-MS/MS experiments were performed on an Orbitrap Fusion (ThermoFisher Scientific, Waltham, MA, USA) equipped with a nanospray EASY-nLC 1200 HPLC system (Thermo Fisher Scientific, Waltham, MA, USA). Peptides were separated using a reversed-phase PepMap RSLC 75 µm i.d.×15 cm long with 2 µm, C18 resin LC column (ThermoFisher Scientific, Waltham, MA, USA). The mobile phase consisted of 0.1% aqueous formic acid (mobile phase A) and 0.1% formic acid in 80% acetonitrile (mobile phase B). After sample injection, the peptides were eluted by using a linear gradient from 5% to 50% B over 30 min and ramping to 100% B for an additional 2 min. The flow rate was set at 300 nL/min. The Orbitrap Fusion was operated in a data-dependent mode in which one full MS scan (60,000 resolving power) from 300 Da to 1500 Da using quadrupole isolation was followed by MS/MS scans in which the most abundant molecular ions were dynamically selected by Top Speed, and fragmented by collision-induced dissociation (CID) using a normalized collision energy of 35%. "Peptide Monoisotopic Precursor Selection" and "Dynamic Exclusion" (8 sec duration), were enabled, as was the charge state dependency so that only peptide precursors with charge states from +2 to +4 were selected and fragmented by CID. Tandem mass spectra were searched against the NCBI human and bovine databases using Proteome Discover v 2.1 with SEQUEST using tryptic cleavage constraints. Mass tolerance for precursor ions was 5 ppm, and mass tolerance for fragment ions was 0.05 Da. Data were analyzed with oxidation (+15.9949 Da) on methionine as a variable post translation modification, and carbamidomethyl cysteine (+57.0215) as a fixed modification. A 1% false discovery rate (FDR) was used as a cut-off value for reporting peptide spectrum matches (PSM) from the database.

Protein Painting Data Analysis and Identification of Hotspots

Individual PSMs for each protein of interest were aligned and compared from at least three independent experiments. Unpainted proteins were used as controls to ensure significant sequence coverage of the protein and ensure proper trypsin digestion. Threshold sequence coverage for unpainted proteins was 50%. Conserved Hippo pathway proteins were identified via protein BLAST and aligned using the Clustal Omega web server.

Generation and Evaluation of Peptide Inhibitors

Peptide inhibitors were synthesized by Peptide 2.0 Inc (Chantilly, VA) and received lyophilized. Peptides were dissolved to 1 mM stock solutions in MilliQ water with the addition of either acetic acid or acetonitrile (ACN) to promote solubility. Final concentrations of acetic acid or acetonitrile in each 1 mM stock solutions are as follows: Peptide 1, 15.3% acetic acid and 14.2% ACN; Peptide 2, 9.8% acetic acid; Peptide 3, 8.9% ACN; Peptide 4, 10.2% CAN; Peptide 5, 5.1% acetic acid; Peptide 6, 5.2% acetic acid; Peptide 7, 3.0% acetic acid; Peptide 8, 3.4% acetic acid. Peptide inhibitors were evaluated for inhibition of PD-1/PD-L1 binding using a PD-1: PD-L1 [Biotinylated] Inhibitor Screening Assay Kit from BPS Biosciences (catalog #72003) according to the manufacturer's directions. Luminescence was measured using a DTX 880 plate reader with 100 ms accumulation time. Each data point was collected in duplicate. Curve fitting was conducted using GraphPad Prism 6 to a sigmoidal dose response curve with equation $Y=\text{Bottom}+(\text{Top}-\text{Bottom})/(1+10^{\wedge}(X-\log IC50))$, where Bottom and Top represent the minimum and maximum plateaus on the sigmoidal curve, respectively. Curve fitting was constrained by setting the parameter Bottom $\geq 0$.

Example 2

Development of Compounds

To develop and identify candidate compounds most highly correlated to successful protein binding, previously used dye classes were examined, and representative molecules selected to probe with model proteins lysozyme and thyroglobulin, representing likely the smallest and the largest protein complex sizes examined with this technique. Representing the diazo class of molecular dyes is Trypan Blue (TB, CAS 72-57-1), a well-known dye used in microscopy and previously used for protein painting; representing the phthalocyanine class of molecular dyes is Direct Blue 199 (DB199, CAS 12222-04-7), a water-soluble dye known to bind carbohydrates, likely in a manner similar to well-known carbohydrate binding dye Alcian Blue; and representing the halogenated small molecule dyes is Acid Orange 50 (AO50, CAS 10214-07-0), a dye we have previously worked with in protein painting.

As shown in FIG. 1, examination of these three dyes with lysozyme and thyroglobulin revealed a few key insights into optimization of dye binding. First, the phthalocyanine dye Direct Blue 199 was unable to bind to lysozyme, and its binding to thyroglobulin was unaffected by high concentration of copper sulfate, indicating that binding was not mediated through the copper ion of the dye, as shown in FIG. 1B. Because the copper moiety of some pthalocyanine-based dyes has been shown to be essential for carbohydrate binding, the lack of copper ion involvement in protein binding to the glycoprotein thyroglobulin suggests that DB199 binding occurs primarily through interactions with the protein rather than interactions with the surface glycans. DB199 binding was dependent on the age of the dye; after one week, significantly lower specific binding was observed. Dyes for experimentation were therefore prepared fresh every morning prior to examination.

Acid Orange 50 conversely, was able to bind both lysozyme as well as thyroglobulin, with specific binding to thyroglobulin of equal magnitude to the specific binding of DB199 to thyroglobulin. We hypothesized that the ability of AO50 to bind lysozyme may be partially dependent on the small size of AO50 as compared to both DB199 and TB and warrants further investigation. TB showed the least specific binding to thyroglobulin and was unable to bind to lysozyme. While the inability to bind lysozyme is hypothesized to be related to the size of the molecules, the limited binding to thyroglobulin was surprising. TB is the most hydrophilic of the commercially available dyes tested, and this hydrophilicity may reduce binding by rendering hydrophobic pockets on the protein inaccessible to the dye.

To further explore the binding hypotheses raised by examination of DB199, AO50, and TB, we concluded that optimization would proceed based on the diazo and halogenated small molecule classes of dye in tandem to investigate both the effect of size as well as hydrophobicity. Because both dyes contain an azo linkage, further optimization of dyes could utilize azo coupling reactions, where electrophilic aryl diazonium salts couple to activated aromatic compounds such as anilines or phenols favoring the para position if available, and the ortho position if not. This chemistry has the advantage of compatibility with aqueous solvents and can be completed in one step, which fulfills the criterion set forth for production of a "universal" dye. Additionally, reaction progress is easy to monitor as color develops when the dye is synthesized.

Two different fast dyes were used to synthesize new dye candidates. Fast Blue B was chosen to synthesize new diazo dyes, as it is structurally similar to the core of TB, while Fast Red TR was chosen to synthesize new halogenated small dyes. Four diverse coupling agents, 4-Amino-1-naphthalenesulfonic Acid or naphthionic acid, 4-Amino-5-hydroxy-2,7-naphthalenedisulfonic acid or H-acid, 7-Amino-1,3-naphthalenedisulfonic acid or Amino G Acid, and 2-napthol were chosen to evaluate the role of sulfonates on specific binding. The dye candidates were synthesized at room temperature in PBS, pH 7.4. During synthesis, it became clear that the coupling agent lacking a sulfonate moiety, 2-napthol, lead to the production of insoluble pigments rather than soluble dyes. Additionally, the dye product of Fast Blue B+Amino G acid was shown to flow through sephadex gel filtration columns without significant loss, eliminating it from consideration as a protein painting dye as any unbound dye could not be effectively removed from the protein solution using gel filtration. The remaining 5 candidate dyes, Fast Blue B+Naphthionic Acid (FBBNA), Fast Blue B+H-acid (FBBHA), Fast Red TR+Naphthionic Acid (FRNA), Fast Red TR+H-acid (FRHA), and Fast Red TR+Amino G Acid (FRAGA), were all evaluated for their specific binding with respect to thyroglobulin (see Table 3).

TABLE 3

Structures of Candidate Dyes based on AO50 and TB

| Coupling Agent ↓ | Fast Blue B 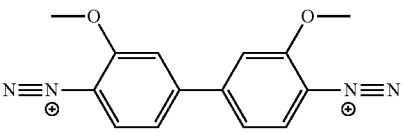 [SMILES: COc1cc(-c2ccc([N+]#N)c(OC)c2)ccc1[N+]#N] | Fast Red TR 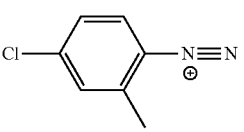 |
|---|---|---|
| Naphthionic Acid 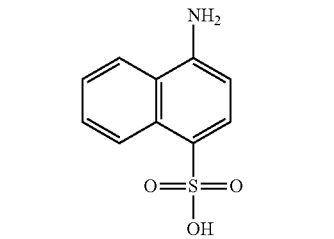 [SMILES: Nc1ccc(S(=O)(=O)O)c2ccccc12] | FBBNA: Soluble, Brown-Red<br>57 molecules/thyroglobulin | FRNA: Soluble, Yellow<br>No binding |
| H-Acid  | FBBHA: Soluble, Dark Purple<br>6 molecules/thyroglobulin | FRHA: Soluble, Dark Pink<br>No binding |
| Amino-G Acid 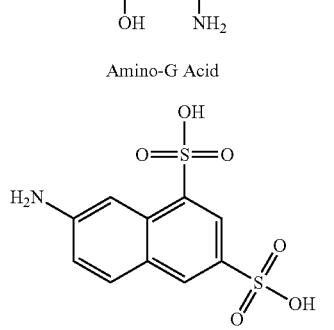 | FBBAGA: Soluble, Brown<br>No binding | FRAGA: Soluble, Tan<br>No binding |
| 2-Napthol 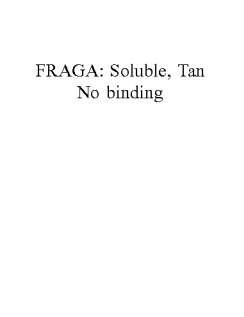 | FBB2N: Dark Blue Pigment<br>Insoluble | FR2N: Bright Orange Pigment<br>Insoluble |

Figure 2:
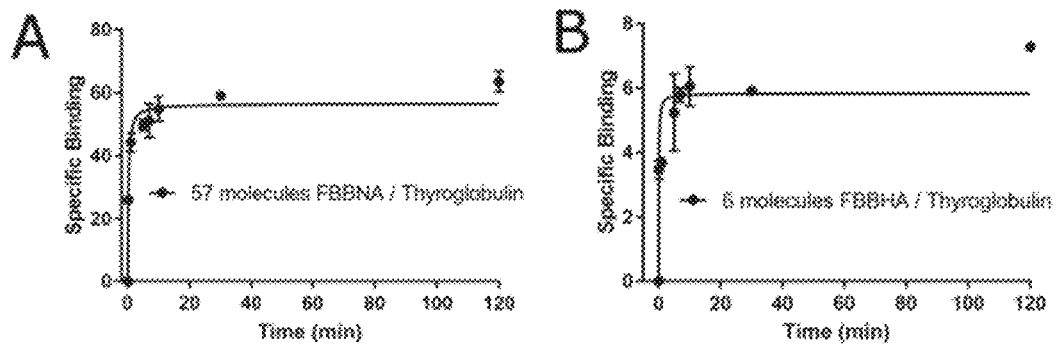
FIGS. 2A-2B are graphs showing specific binding of FBBNA (i.e., compound of Formula (II)) and FBBHA (i.e., compound of Formula (III)). A) Specific Binding of FBBNA to Thyroglobulin. B) Specific Binding of FBBHA to Thyroglobulin. All data points were collected in duplicate, and final data was fit to the Michaelis Menton equation where Vmax represents specific binding at saturation.

None of the Fast Red TR-based dyes including FRNA, FRHA, and FRAGA showed any significant binding to thyroglobulin. Both FBBNA (FIG. 2A) and FBBHA (FIG. 2B) were shown to bind to thyroglobulin. FBBHA specific binding had a similar magnitude as the specific binding of TB, which is structurally similar. FBBNA however had an unexpectedly high specific binding to thyroglobulin, with almost 10-fold greater specific binding than FBBHA and was chosen for further investigation.

Fast Blue B was coupled to three additional isomers of naphthionic acid, including 1-Amino-8-naphthalenesulfonic acid (Peri Acid), 5-Amino-1-naphthalenesulfonic acid (Laurent Acid), and 1-Naphthylamine-6-sulfonic Acid (1,6 Cleve's Acid, or Cleve Acid) to investigate the effect of the position of the sulfonate moiety on binding. All of the dyes were soluble and of similar colors, with their structures shown in Table 4. We hypothesized that as the hydrophobic area of the coupling agent was reduced as the sulfonate group moved around the ring structure, the specific binding of the dye candidate would be reduced, with FBBNA and FBBPA having significantly higher specific binding than FBBLA or FBBCA.

TABLE 4

Structures of Candidate Dyes based on FBBNA.

Fast Blue B

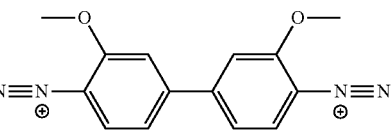

| Coupling Agent ↓ | |
| --- | --- |
| Naphthionic Acid<br>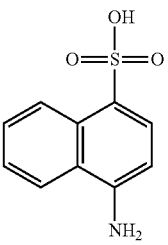 | FBBNA: Soluble, Brown-Red<br>57 molecules/thyroglobulin |
| Peri Acid<br>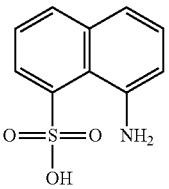 [SMILES: Nc1cccc2cccc(S(=O)(=O)O)c12] | FBBPA: Soluble, Pink-Purple<br>37 molecules/thyroglobulin |
| Laurent Acid<br>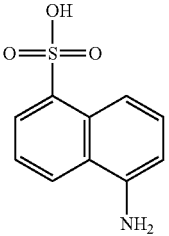 [SMILES: Nc1cccc2c(S(=O)(=O)O)cccc12] | FBBLA: Soluble, Pink-Red<br>32 molecules/thyroglobulin |
| Cleve's Acid<br>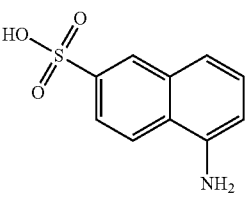 [SMILES: Nc1cccc2cc(S(=O)(=O)O)ccc12] | FBBCA: Soluble, Brown-Purple<br>7 molecules/thyroglobulin |

Figure 3:
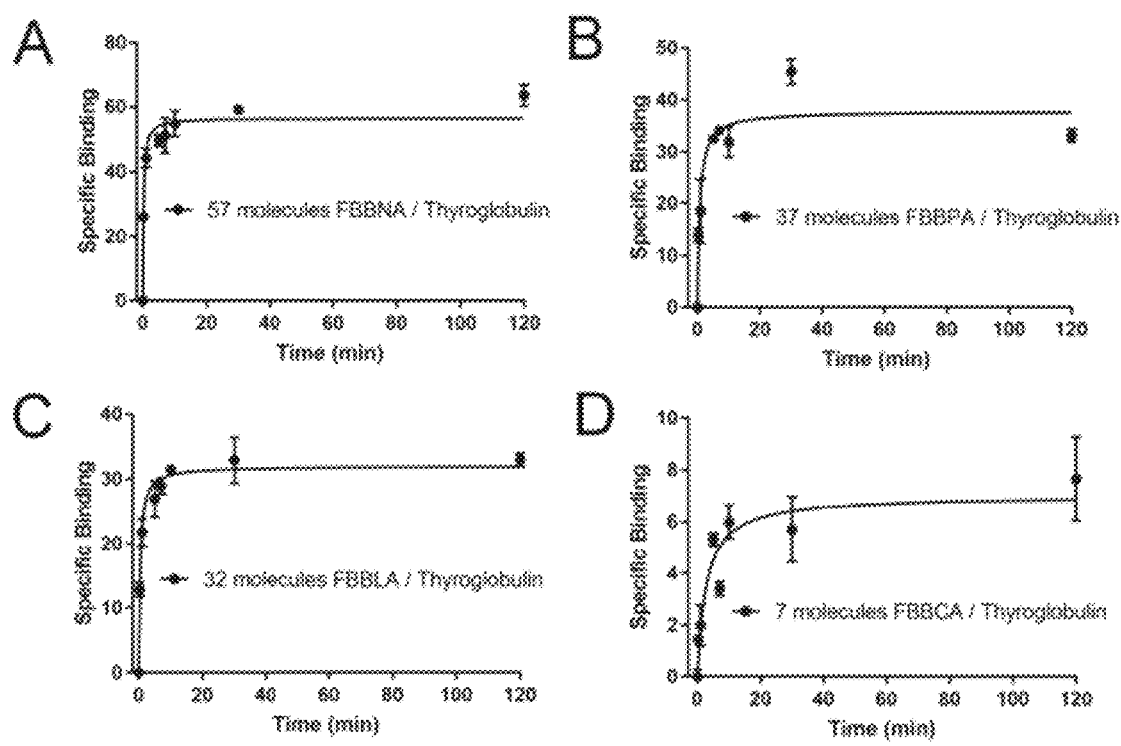
FIGS. 3A-3D are graphs showing specific binding of FBBNA compared to FBBPA, FBBLA, and FBBCA. FBBNA had the highest specific binding of the four compounds tested. A) Specific Binding of FBBNA to Thyroglobulin. B) Specific Binding of FBBPA to Thyroglobulin. C) Specific Binding of FBBLA to Thyroglobulin. D) Specific Binding of FBBCA to Thyroglobulin. All data points were collected in duplicate, and final data was fit to the Michaelis-Menton equation where Vmax represents specific binding at saturation.

As shown in FIG. 3, FBBNA retained the highest specific binding of the four candidate dyes tested, while FBBCA had the lowest specific binding, as hypothesized. However, FBBPA had significantly reduced binding as compared to FBBNA, despite having a large portion of the naphthalene ring free to bury into hydrophobic pockets. We hypothesize that not only is a hydrophobic "anchor" important for binding to hydrophobic pockets of the protein, but the presence of an unobstructed aryl ring such as is found on FBBNA may allow for tighter pi-stacking interactions with aromatic amino acids proteins than is possible for FBBPA.

Example 3

Determination of the Structure and Binding Properties

In order to directly determine moieties with the largest influence on binding, the structure via NMR of the two primary components of FBBNA was determined. Naphthionic acid can be represented by several resonance structures that lead to a partial negative charge on three positions of the naphthalene ring. The classical "activated" position is the ortho position to the primary amine, which is where naphthionic acid is assumed to couple to an aryl diazonium compound as in the case of the dye Congo Red. However, side products consisting of compounds coupling at alternative positions may also represent unique, high-affinity dyes; they also provide a way to compare small changes in structure to protein-binding properties.

Figure 4:
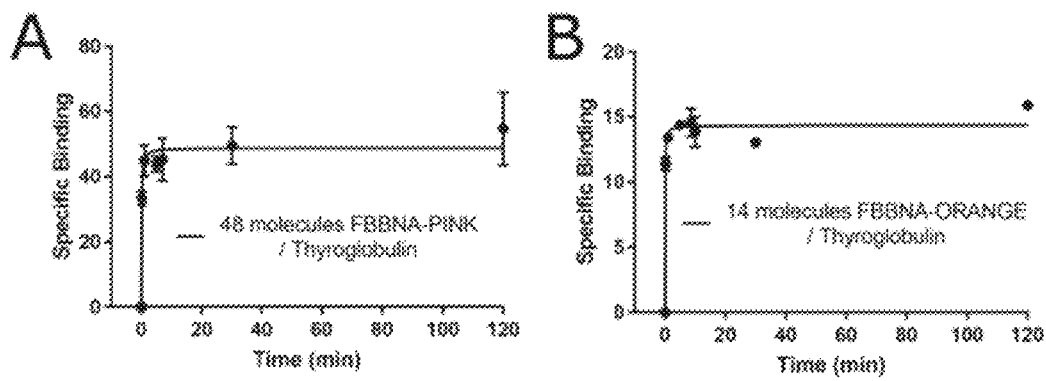
FIGS. 4A-4B are graphs showing specific binding of each component of FBBNA. Both of the two major products found in FBBNA bound to thyroglobulin. A) A total of 48 molecules of the high retention factor component of FBBNA-PINK bound to each molecule of thyroglobulin. B) A total of 14 molecules of the low retention factor component of FBBNA-ORANGE bound to each molecule of thyroglobulin.

FBBNA consists of two primary bands on reverse-phase TLC. These bands were separated via reverse phase flash chromatography and each of the two compounds were examined for their protein binding capability as shown in FIG. 4. The "pink" band was shown to bind to thyroglobulin at three times greater numbers than the orange band, indicating that the pink band was the higher affinity species in the FBBNA dye. However, as the total binding of the two compounds was roughly equal to the specific binding of the complex FBBNA dye, we can hypothesize that these two species bind to unique sites on thyroglobulin.

Using the structure of the high affinity pink dye component of FBBNA, we docked this dye to the PDB coordinates for carbonic anhydrase using PatchDock and compared the binding energy to that of AO50 binding to carbonic anhydrase. We found that as predicted, the binding affinity of FBBNA to carbonic anhydrase was much higher than for AO50 to carbonic anhydrase.

Example 4

Molecular Dye Mixture FBBNA Binds to Proteins of a Large Range of Sizes, and Remains Significantly Bound in the Presence of Heat Treatment Based on the high specific binding of FBBNA to thyroglobulin, and the unique binding of each of the primary species, we examined the specific binding of the complex dye to six proteins to determine size-dependence of specific binding. Shown in Table 5 are the six standard proteins examined. FBBNA effectively bound to all proteins tested except lysozyme, suggesting that despite the significant specific binding to all other proteins tested, FBBNA is still too large to effectively bind to the smallest proteins.

TABLE 5

FBBNA specific binding to six standard proteins. Percentage sequence coverage and specific binding were measured in duplicate.

| Protein Name | Uniprot Number | Species | Complex Weight (kDa) | pI | Stokes Radius (nm) | Specific Binding, 2 hrs |
|---|---|---|---|---|---|---|
| Lysozyme | B8YK79 | *Gallus gallus* | 16 (monomer) | 9.36 | 1.89 | 0.59 ± 0.59 |
| Carbonic anhydrase | P00921 | *Bos taurus* | 29 (monomer) | 6.41 | 2.29 | 8.04 ± 0.91 |
| Serum albumin | P02769 | *Bos taurus* | 69 (monomer) | 5.82 | 3.55 | 13.23 ± 0.80 |
| Catalase | P00432 | *Bos taurus* | 240 (tetramer) | 6.79 | 5.20 | 26.78 ± 1.03 |
| Apoferritin | P02791 Q8MIP0 | *Equus caballus* | 479 (24-mer) | 5.37 | 6.10 | 32.09 ± 0.66 |
| Thyroglobulin | P01267 | *Bos taurus* | 660 (dimer) | 5.48 | 8.58 | 63.54 ± 2.35 |

FIG. 4A shows that the specific binding of FBBNA at 2 hours for each protein follows a linear size-dependent trend. Additionally, FBBNA remains mostly bound following denaturation of the protein at 100 C for 10 min. Because some proteins, such as apoferritin, are particularly stable and may need to be subject to high temperatures in order to fully denature prior to trypsinization and mass spectrometry, it is important that a universal dye candidate remain bound despite such treatment. While apoferritin has an unusually high denaturation point, greater than 93 C at pH 7, the residual dye bound after such treatment indicates that the dye can remain bound even upon denaturation.

Example 5

Binding of Molecular Dyes AO50 and FBBNA Protects Bound Regions of Proteins from Denaturation by Chemotropic Agent Urea or Heat Upon the discovery that significant amounts of FBBNA remain bound even at high temperatures, we hypothesized that binding of the dye to the protein complex of interest may stabilize the bound regions of the proteins and protect from denaturation, particularly if proteins are denatured using the mild denaturant urea. The consensus view of the mechanism of denaturation of proteins by urea is given in Das, A., and Mukhopadhyay, C., "Urea-Mediated Protein Denaturation: A Consensus View," J. Phys. Chem. B. 113, 12816-12824 (2009); proteins denatured by urea are reported to retain some secondary structure, with hydrophobic proteins retaining the most secondary structure (Nick Pace, C., Huyghues-Despointes, B. M. P., Fu, H., Takano, K., Scholtz, J. M., and Grimsley, G. R., "Urea denatured state ensembles contain extensive secondary structure that is increased in hydrophobic proteins," Protein Sci. Publ. Protein Soc. 19, 929-943 (2010); Bennion, B. J., and Daggett, V., "The molecular basis for the chemical denaturation of proteins by urea," Proc. Natl. Acad. Sci. U.S.A 100, 5142-5147 (2003)). Without wishing to be held to any particular theory, urea is thought to first displace the solvation shell around the protein, both through direct interactions with the protein as well as through indirect effects in which urea disrupts the hydrogen bonding network of water allowing for increased access of the urea to the protein. Urea preferentially makes contacts with the protein backbone, displacing backbone-water H-bonds with backbone-urea H-bonds. The denatured state is then stabilized through backbone-urea interactions as well as backbone-hydrophobic side chain interactions in which urea binding is enthalpically and entropically favored by freeing the bulk water to form water-water H-bonds. Because urea denatures proteins only partially, and is dependent early on backbone-urea interactions, protection of the protein backbone by dyes may help increase the amount of secondary structure remaining following denaturation.

Figure 5:
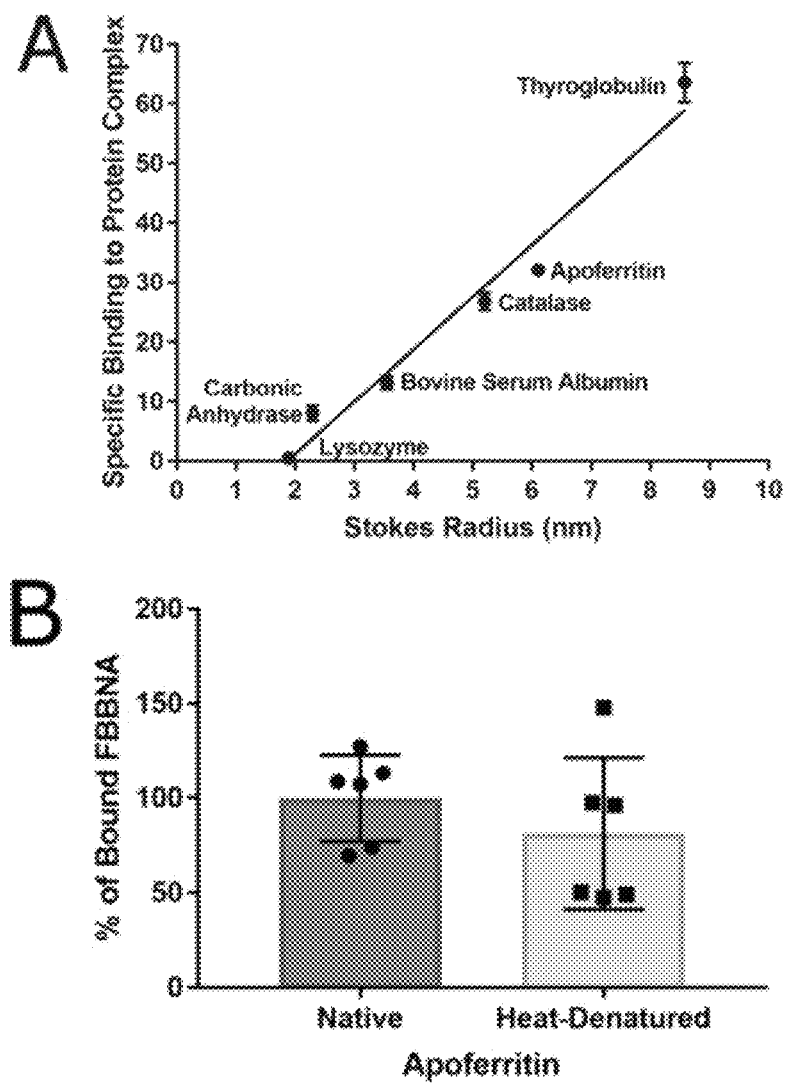
FIGS. 5A-5B are graphs showing binding behavior of FBBNA. A) FBBNA binds to multiple proteins in a size-dependent manner. Specific binding is not significantly affected by the presence of glycosylation (thyroglobulin) or metallo-binding prosthetic groups (catalase). B) The percentage of FBBNA bound to apoferritin decreased only slightly upon heating at 100 C for 10 min. FBBNA was allowed to bind to apoferritin, excess was removed by gel filtration, then native samples were incubated at room temperature for 10 minutes while heat denatured samples were incubated at 100 C for 10 min. Samples were subsequently passed through a second gel filtration column and binding was compared.
Figure 6:
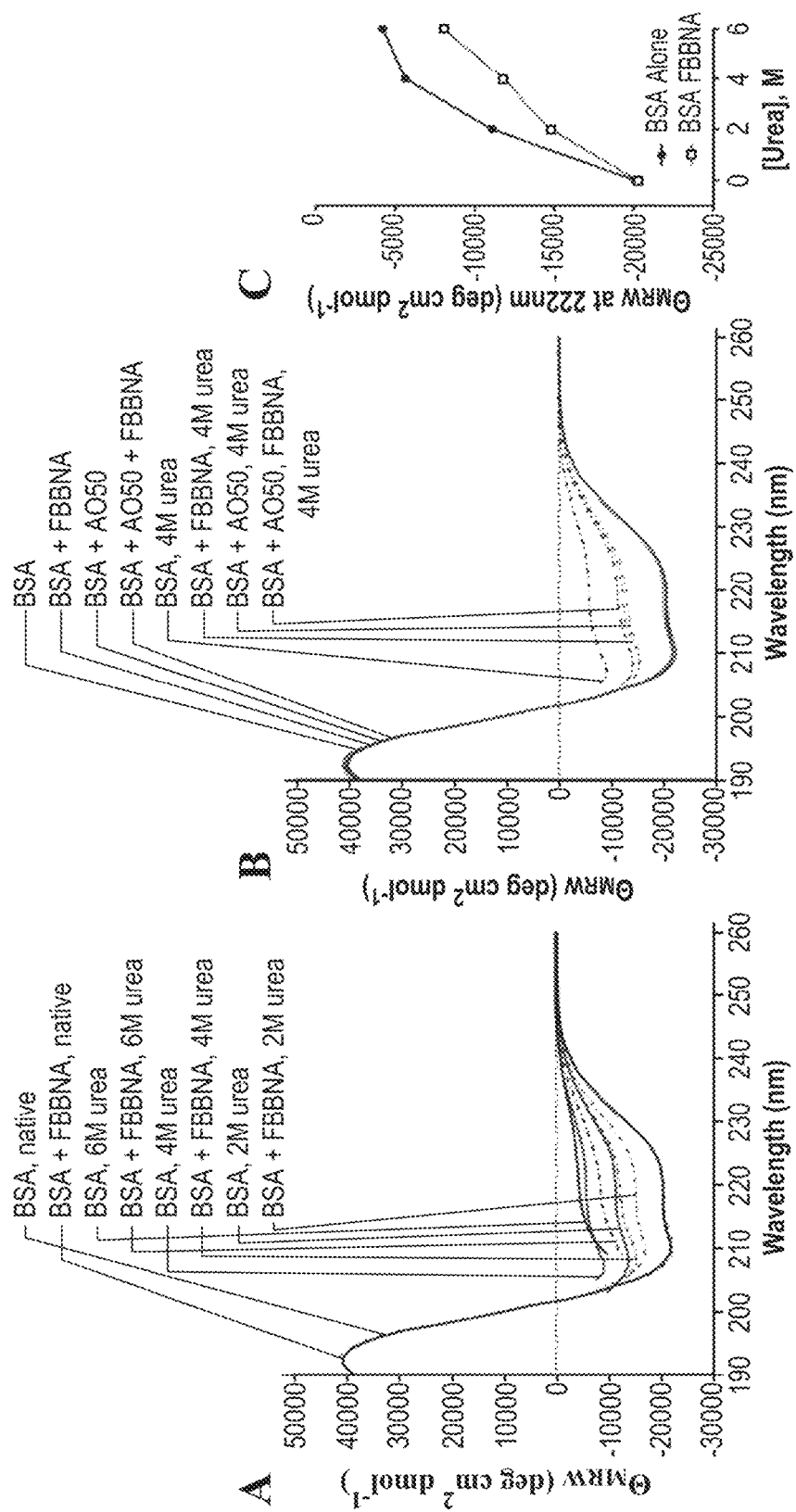
FIGS. 6A-6C are graphs showing circular dichroism spectroscopy of bovine serum albumin in the presence of molecular dyes. A) Native secondary structure of BSA does not change in the presence of FBBNA dye. Denaturation at 2M, 4M, and 6M is attenuated in the presence of FBBNA at 2M, 4M, and 6M as measured by an increase in helical content of the CD spectra. B) Native secondary structure of BSA does not change in the presence of AO50 dye or the combination of AO50 and FBBNA. Denaturation by 4M urea is attenuated by FBBNA, AO50, and FBBNA+AO50 as compared to BSA denatured without dye. C) Larger magnitude mean residue ellipticity at 222 nm was observed for BSA in the presence of FBBNA dye as compared to BSA alone in all urea concentrations tested. The greatest difference in magnitude was observed at 4M urea.

In order to test the hypothesis that dye binding decreases total denaturation of the protein, circular dichroism spectroscopy was performed on native, denatured, and dye-bound samples of bovine serum albumin to determine the extent of denaturation in the presence of the dye. In FIG. 5A it was observed that upon treatment with FBBNA for 10 minutes, BSA was partially stabilized against denaturation at 2M, 4M, and 6M urea. Additionally, the presence of FBBNA did not affect the secondary structure of BSA, confirming its utility for protein painting analysis. Because FBBNA failed to bind to lysozyme, potentially due to its large size, we additionally examined the affect of FBBNA binding on protein denaturation in comparison to AO50, as well as in conjunction with AO50. Shown in FIG. 5B, both AO50 and FBBNA both were able to partially stabilize BSA against denaturation and were able to do so in conjunction as well. This data, in conjunction with FIG. 5C showing the greatest protection at 4M urea, suggest that a "universal" protein painting dye could consist of both FBBNA and AO50 in combination, and that the protein painting protocol could be conducted using 4M urea without detriment.

Furthermore, this data suggests a mechanism by which protein painting dyes can protect regions of proteins from trypsinization, even after denaturation. An individual dye molecule binds to a protein region consisting of amino acids than may be separated in the primary sequence by adjacent in the native folded protein; upon exposure to urea, the dye-bound area resists denaturation and remains partially folded, as demonstrated by the stabilization of some of the secondary structure of BSA when bound to FBBNA or AO50. Upon trypsinization, the folded, dye-bound regions are inaccessible to trypsin cleavage. As a note, trypsinization in the protein painting protocol is conducted very rapidly (2 hrs or less) to ensure significant digestion prior to significant disassociation of the dye. Based on this CD data, one could hypothesize that upon trypsinization, even dye molecules that dissociate may leave behind regions that remain partially folded, suggesting that will still be somewhat less amenable to trypsinization than the denatured regions of the proteins. Given our characterization of FBBNA, and the growing understanding of how the dye may be functioning in a protein painting protocol, we decided to test the new dye in case study using two proteins in the Hippo pathway.

Example 6

Protein Painting of Hippo Signaling Pathway Proteins

The Hippo pathway, a signaling network with both pro-apoptotic and anti-apoptotic activities, regulates growth and differentiation of tissues and has been implicated in wound-healing processes. Specifically, Hippo pathway signaling is shown to regulate wound-induced polyploidization, or expansion of non-dividing diploid cells, in *Drosophila*. Mammalian transcriptional factors YAP and TAZ upregulate a host of essential wound healing genes, such that siRNA knockdown of either YAP or TAZ results in a delayed rate of skin wound closure. YAP itself is an bonafide oncogene upregulated in some cancers, and is regulated in vivo by a variety of different proteins such as kinase LATS, zonula occuldens proteins (ZO), and regulatory 14-3-3, which primarily effect that migration of YAP from the cytoplasm to the nucleus. When the core Hippo pathway is activated, phosphorylation by LATS on Ser 127 of YAP allows binding of regulatory 14-3-3, preventing YAP from translocating to the nucleus. However, if YAP remains unphosphorylated on Ser127, it may translocate to the nucleus to interact with a variety of transcription factors, including TEAD and p73. YAP may thus have both pro-apoptotic and pro-proliferative effects; YAP interaction with TEAD is shown to promote expression of growth factors and support proliferation, while YAP interaction with p73 promotes apoptosis. Given YAP's role as a "model of functional dichotomy" as well as the fact that YAP is thought to be partially unstructured in its native state, drug development for modulation of Hippo pathway signaling is often focused on binding partners of YAP, such as TEAD, rather than on YAP itself.

One set of binding partners of YAP worth some attention are the zona occludens (ZO) family of proteins consisting of three isoforms, ZO-1, ZO-2, and ZO-3, which form intracellular plaques that join transmembrane proteins with the actin cytoskeleton at tight junctions. ZO-2 was found to facilitate nuclear localization of YAP, and specifically was involved in regulating the pro-apoptotic function of YAP2. Interactions between ZO proteins and YAP2 are facilitated by interaction between the first PDZ domain of ZO proteins and the C-terminal PDZ-binding domain of YAP2. Given the paucity of crystal structures of YAP with protein binding partners, and the interest in regulation of specifically of the pro-apoptotic activity of the Hippo pathway in the context of wound healing, YAP complex YAP2/ZO-1 was probed and unique regions on each protein corresponding to interaction "hotspots" were identified, using the protein painting technique. The proteins were painted with a 1:1 dye mixture of both FBBNA and AO50 to ensure the highest coverage of painted proteins.

Figure 7:
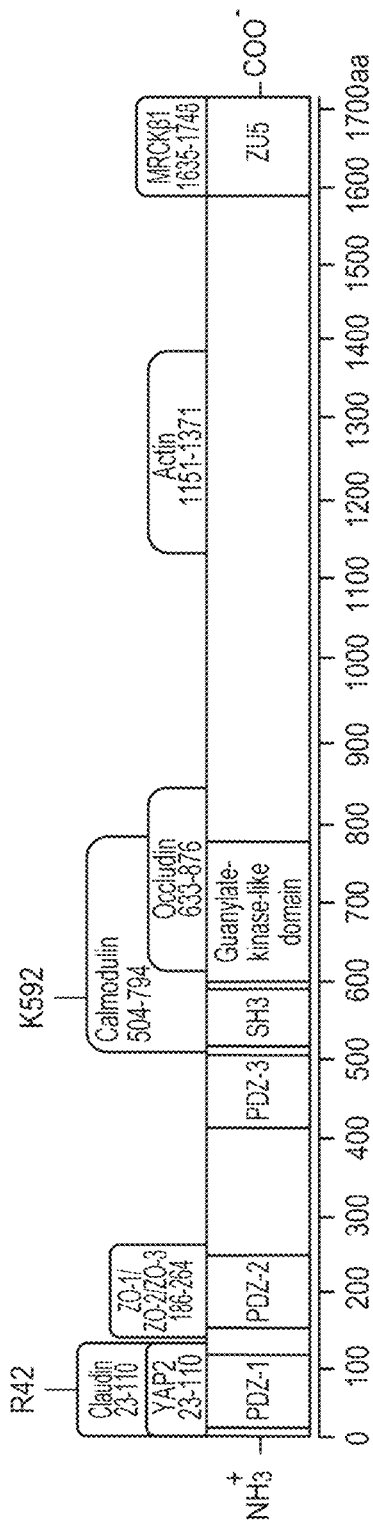
FIG. 7 depicts ZO-1 hotspots in the ZO-1-YAP2 complex as identified by protein painting. TJP1 is shown with PDZ domains, SH3 domain, guanylate kinase-like domain, and ZUS domain. A selection of known binding partners are shown as tabs above the structure, with their binding regions given as amino acid positions in ZO-1. All hotspots were identified in three independent protein painting experiments.

Two hotspots of ZO-1 (isoform a, NP_003248.3), in complex with YAP2 (YAP 1-2 gamma, NP_001123617.1) were identified, shown in FIG. 7. Both identified hotspot peptides are highly conserved in evolution. The first hotspot, R42, was found within the first PDZ-domain of ZO-1, the canonical YAP recognition site. While the first PDZ domain of ZO-1 has not been crystalized with the C-terminal binding domain of YAP, structures of the first PDZ domain of ZO-1 in complex with other C-terminal peptides are available. In addition to this hotspot in the known binding domain, one additional hotspot at K592 right between the SH3 domain and guanylate kinase-like domain of ZO-1 was identified, within the documented calmodulin binding site. Due to the large number of binding partners of tight junction proteins, it is conceivable that multiple binding partners of ZO proteins could have overlapping binding sites, such that binding of two partners to ZO proteins is mutually exclusive. Based on early protein painting data, it is possible that YAP binding and calmodulin binding to ZO-1 are mutually exclusive; additional research into these regulatory questions is ongoing.

Figure 8:
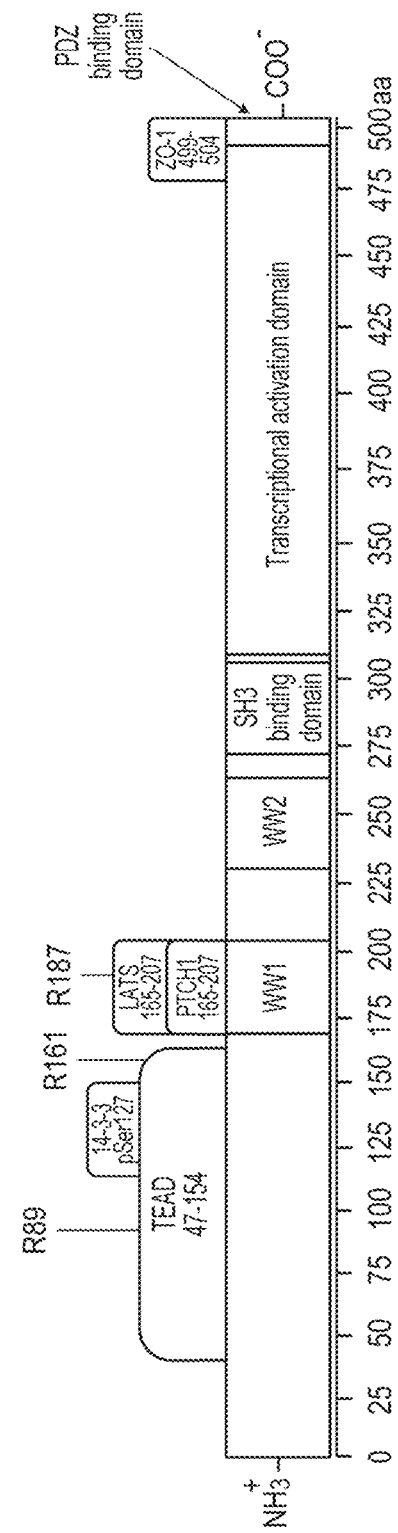
FIG. 8 depicts YAP2 hotspots in the ZO-1-YAP2 complex as identified by protein painting. YAP2 is shown with WW domains, SH3 domain, transcriptional activation domain, and PDZ binding domain. A selection of known binding partners are shown as tabs above the structure with their binding regions given as amino acid positions in YAP2. All hotspots were identified in three independent protein painting experiments.

In conjunction with the two hotspots identified on ZO-1, three hotspots were identified on YAP2, as shown in FIG. 8. Sequence coverage of the C-terminal region of YAP via mass spectrometry was suboptimal; no coverage was obtained from residues 441-504, the region of the protein containing the canonical ZO-1 binding domain, due to lack of tryptic cleavage sites. Interestingly, the three hotspots obtained, R89, R161, and R187, were not in highly evolutionarily conserved regions. The first two hotspots were found in the relatively unconserved, proline rich N-terminal region of the protein known to bind TEAD. R187 is found in the first WW domain of the protein known to bind LATS as well as Patched. It is tempting to suppose that the K592 hotspot identified near the SH3-domain of ZO-1 and the R89 hotspot identified in YAP (hotspot peptide KLPDSFFKP-PEPK) could indicate some interaction between the SH3 domain and its recognition motif P-x-x-P in the R89 peptide, although the presence of a glutamic acid residue within the P-x-x-P motif is unusual as the SH3 binding cavity is fairly hydrophobic. Regardless, the presence of multiple hotspots within the N-terminal region of YAP is intriguing and suggests there may be more to this region of the protein than previously supposed based on the limited conservation.

Example 7

Painting of the PD-1/PD-L1 Complex

In addition to the case study of the Hippo pathway, we also demonstrate the utility of protein painting in the case study of PD-1/PD-L1, two proteins involved in the development of immune checkpoint inhibitors. One of the newest, most successful approaches in cancer drug discovery is the development of immune checkpoint inhibitors as cancer therapeutics. Keytruda® (pembrolizumab, anti-PD-1 antibody developed by Merck) and Opdivo® (nivolumab, anti-PD-1 antibody developed by Bristol-Meyers Squibb) are mAb therapeutics and recent checkpoint inhibitors to hit the market. Since their introduction, both Keytruda and Opdivo have received considerable attention due to their efficacy; President Jimmy Carter credited Keytruda for halting the progression of advanced melanoma which had spread to his brain. Despite the success of these immune checkpoint inhibitors, there are several problems to consider. First, the large size of mAb therapeutics leads to poor tissue penetration; second, mAb therapeutics cannot be dosed orally; third, difficulty in manufacturing/validation make mAbs harder to produce than small molecules; and fourth, side effects can include detrimental immune responses.

There have been very few reports of small molecule inhibitors targeting the PD-1/PD-L1 interface; reports of Bristol Meyers Squibb compounds targeting the interface showed high cytotoxicity and poor efficacy and were not evaluated in the clinic. We used protein painting to determine the interface region of PD-1/PD-L1 and used the interface hotspot peptides to design 8 unique peptides targeting the interface. We found one hotspot region of PD-1 centered around Lys 78. Shown in Table 4, four inhibitors were designed around the Lys 78 hotspot region on PD-1, two around the predicted binding region on PD-L1, and two as a combination of amino acids from both PD-1 and PD-L1. For each peptide, sequences were compared in both linear and cyclized conformations; cyclized peptides were prepared by adding cysteine residues to the N and C terminus of the parent sequence and subsequently cyclizing via disulfide bond formation. These cyclized peptides may be more stable in solution.

TABLE 1

Sequence and Design of 8 peptide inhibitors of the PD-1/PD-L1 interface.

| # | Sequence/Design | Solubility (to 1 mM) |
|---|---|---|
| 1 | YRCMISYGGADYKRITV<br>PD-L1: Residues 112-128 | 60% $CH_3COOH$,<br>14% $CH_3CN$ |
| 2 | CYRAMISYGGADYKRITC<br>Inhibitor 1 cyclized via<br>Cys-Cys bond | 40% $CH_3COOH$ |
| 3 | LKYDAPAFTVT<br>PD-L1: L15, K124-A121,<br>P24, A18-T22 | 14% $CH_3CN$ |
| 4 | CLKYDAPAFTVTC<br>Inhibitor 3 cyclized via<br>Cys-Cys bond | 14% $CH_3CN$ |
| 5 | LNWYRMSPSNQTDKLAA<br>PD-1: Residues 65-81 | 10% $CH_3COOH$ |
| 7 | CLNWYRMSPSNQTDKLAAC<br>Inhibitor 5 cyclized via<br>Cys-Cys bond | 10% $CH_3COOH$ |
| 8 | AISLAPKAQIK<br>PD-1: Residues 125-135 | 10% $CH_3COOH$ |
| 9 | CAISLAPKAQIKC<br>Inhibitor 7 cyclized via<br>Cys-Cys bond | 10% $CH_3COOH$ |

Figure 9:
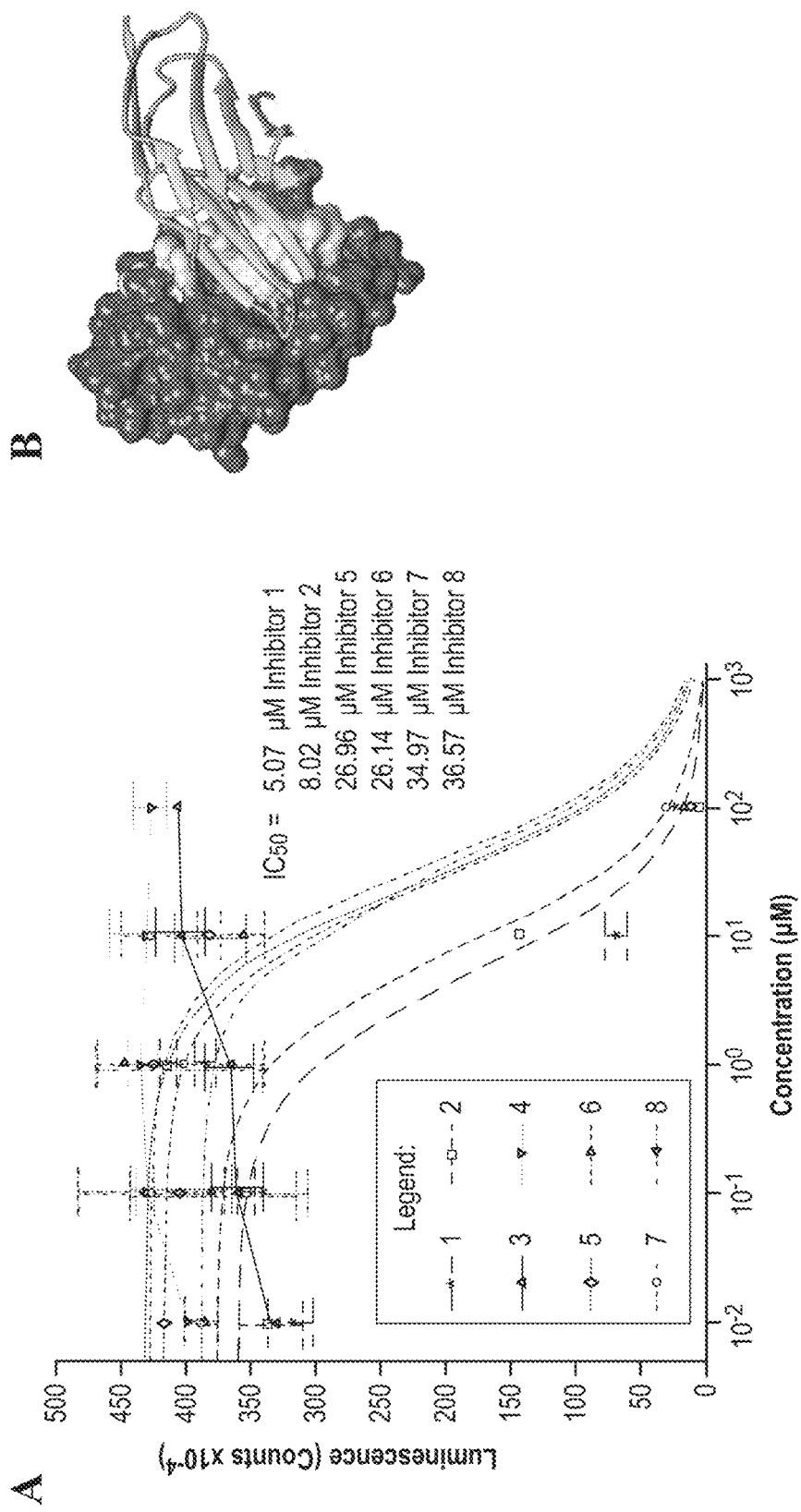
FIGS. 9A-9B depict graph and crystal structure, respectively, for peptide inhibitors of PD-1/PD-L1 designed using protein painting results. A) Peptides 1-8 were tested over a concentration range of 10 nM-100 µM for inhibition of protein-protein interactions between PD-1 and PD-L1. The most effective inhibitors were 1 and 2, designed to mimic PD-L1, and had IC50 values less than 10 µM. All data points were collected in duplicate, and data was fit to a sigmoidal dose response curve with the following constraints: baseline ≥0. B) Crystal structure of human PD-1/PD-L1 complex, PDB 4ZQK, where PD-L1 is shown using a space filling model, and PD-1 is shown using a ribbon model. The residues of PD-L1 comprising Inhibitor 1 are shown, and are found at the interface of the two proteins.

To test each of these peptide inhibitors, concentrations up to 100 μM were tested in a PD-1/PD-L1 interaction kit available from BPS Biosciences. As shown in FIG. 9A, the inhibitors designed as combination of sequences from PD-1 and PD-L1 were not effective. However, all remaining inhibitors were effective at 100 μM, and Inhibitors 1 and 2 had IC50 values under 10 μM. Using the crystal structure of PD-1/PD-L1 complex, FIG. 9B shows the residues of PD-L1 comprising Inhibitor 1, and how inhibitors mimicking this region positioned in the protein-protein interface can effectively disrupt complex formation. These compounds demonstrate the utility of the protein painting method in leading from a mass spectrometry hit directly to a molecule that disrupts protein complex formation.

We claim:

1. A peptide comprising the amino acid sequence set forth as:

CYRAMISYGGADYKRITC (SEQ ID NO:2);

CLKYDAPAFTVTC (SEQ ID NO:4); or

CLNWYRMSPSNQTDKLAAC (SEQ ID NO:7).

2. A method for preventing or disrupting an interaction between a programmed death 1 (PD-1) and a programmed death ligand 1 (PD-L1), the method comprising contacting PD-1 or PD-L1 with the peptide of claim 1 before, concomitant with, or after the interaction between PD-1 and PD-L1.

3. A peptide comprising the amino acid sequence set forth as: CYRAMISYGGADYKRITC (SEQ ID NO:2).

4. A peptide comprising the amino acid sequence set forth as: CLKYDAPAFTVTC (SEQ ID NO:4).

5. A peptide comprising the amino acid sequence set forth as: CLNWYRMSPSNQTDKLAAC (SEQ ID NO: 7).

* * * * *